US00RE37035E

(19) United States

(12) Reissued Patent

Grell et al.

(10) Patent Number: US RE37,035 E

(45) Date of Reissued Patent: Jan. 30, 2001

(54) PHENYLACETIC ACID BENZYLAMIDES

(75) Inventors: Wolfgang Grell; Rudolf Hurnaus, both of Biberach; Gerhart Griss, deceased, late of Biberach, by Elisabeth Griss, executrix; Robert Sauter, Laupheim; Manfred Reiffen, Biberach, all of (DE); Eckhard Rupprecht, Guntramsdorf (AT)

(73) Assignee: Boehringer Ingelheim KG, Ingelheim (DE)

( * ) Notice: This patent is subject to a terminal disclaimer.

(21) Appl. No.: 08/946,602

(22) Filed: Oct. 7, 1997

Related U.S. Patent Documents

Reissue of:

(64) Patent No.: 5,216,167
Issued: Jun. 1, 1993
Appl. No.: 07/495,820
Filed: Mar. 19, 1990

U.S. Applications:

(63) Continuation of application No. 07/302,022, filed on Jan. 25, 1989, now abandoned, which is a continuation-in-part of application No. 06/872,706, filed on Jun. 10, 1986, now abandoned, which is a continuation-in-part of application No. 06/684,054, filed on Dec. 20, 1984, now abandoned, and a continuation-in-part of application No. 06/878,921, filed on Jun. 26, 1986, now abandoned.

(30) Foreign Application Priority Data

| | | |
|---|---|---|
| Dec. 30, 1983 | (DE) | 3347565 |
| Jun. 25, 1985 | (DE) | 3522604 |
| Jul. 1, 1985 | (DE) | 3523466 |

(51) Int. Cl.[7] ..... A61K 31/40; A61K 31/445; C07D 207/08; C07D 211/32

(52) U.S. Cl. ..... 514/234; 514/212.01; 514/326; 514/331; 514/422; 514/429; 514/450; 514/461; 514/522; 514/619; 540/611; 546/214; 548/568; 549/414; 549/415; 549/426; 549/427; 549/473; 549/496; 558/414; 564/168

(58) Field of Search ..... 546/234, 214; 548/517, 568; 564/168; 514/331

(56) References Cited

U.S. PATENT DOCUMENTS

| | | | |
|---|---|---|---|
| 3,647,804 | 3/1972 | Rynbrandt et al. . | |
| 3,674,944 | 7/1972 | Iemura et al. . | |
| 3,678,094 | 7/1972 | Shen et al. . | |
| 3,692,821 | 9/1972 | Sarett et al. . | |
| 4,158,063 | 6/1979 | Hitzel et al. . | |
| 4,385,066 | 5/1983 | Ainsworth et al. . | |
| 4,542,127 | 9/1985 | Hiztel et al. | 546/194 |
| 4,735,959 | 4/1988 | Grell et al. . | |
| 4,863,724 | 9/1989 | Schepky et al. | 424/80 |
| 4,873,080 | 10/1989 | Brickl et al. | 424/80 |

FOREIGN PATENT DOCUMENTS

| | | |
|---|---|---|
| 0147830 | 10/1985 | (EP) . |
| 2090834A | 7/1982 | (GB) . |
| 2091729A | 8/1982 | (GB) . |
| 2100261 | 12/1982 | (GB) . |
| 2124220 | 2/1984 | (GB) . |

OTHER PUBLICATIONS

Frahm & Knapp, Tetrahedron Letters, vol. 22, 28, pp. 2633–2636 (1981).

Demailly and Solladie, Tetrahedron Letters, vol. 29, pp 1472 (1975).

*Primary Examiner*—Richard L. Raymond

(74) *Attorney, Agent, or Firm*—R. P. Raymond; A. R. Stempel; M-E M. Devlin

(57) ABSTRACT

Phenylacetic acid benzylamides having the following general structure wherein the substituents are defined herein, are disclosed, which compounds are hypoglcemic agents.

15 Claims, 12 Drawing Sheets

FIG. 1 (PART 1)
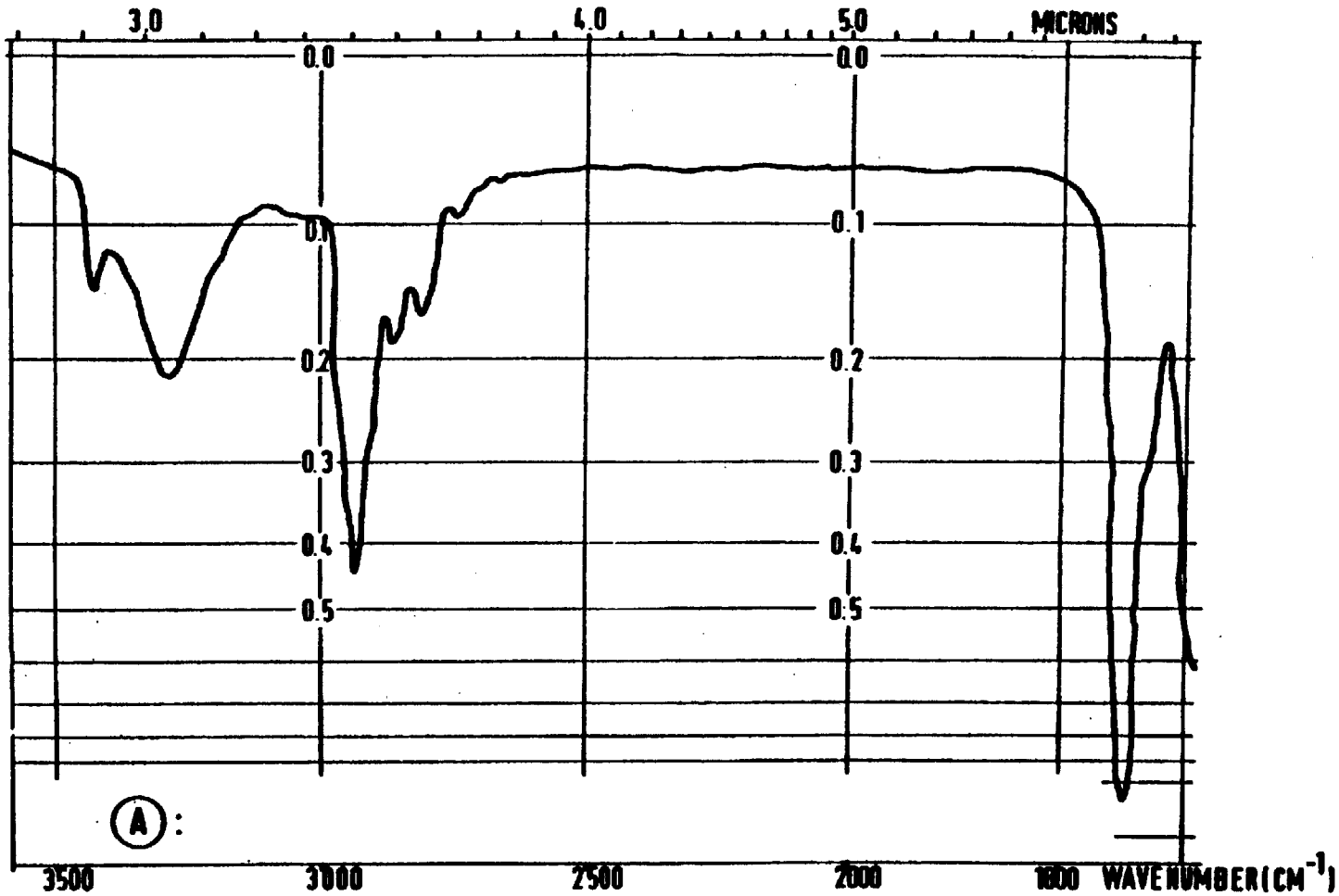

FIG. 1 (PART 2)
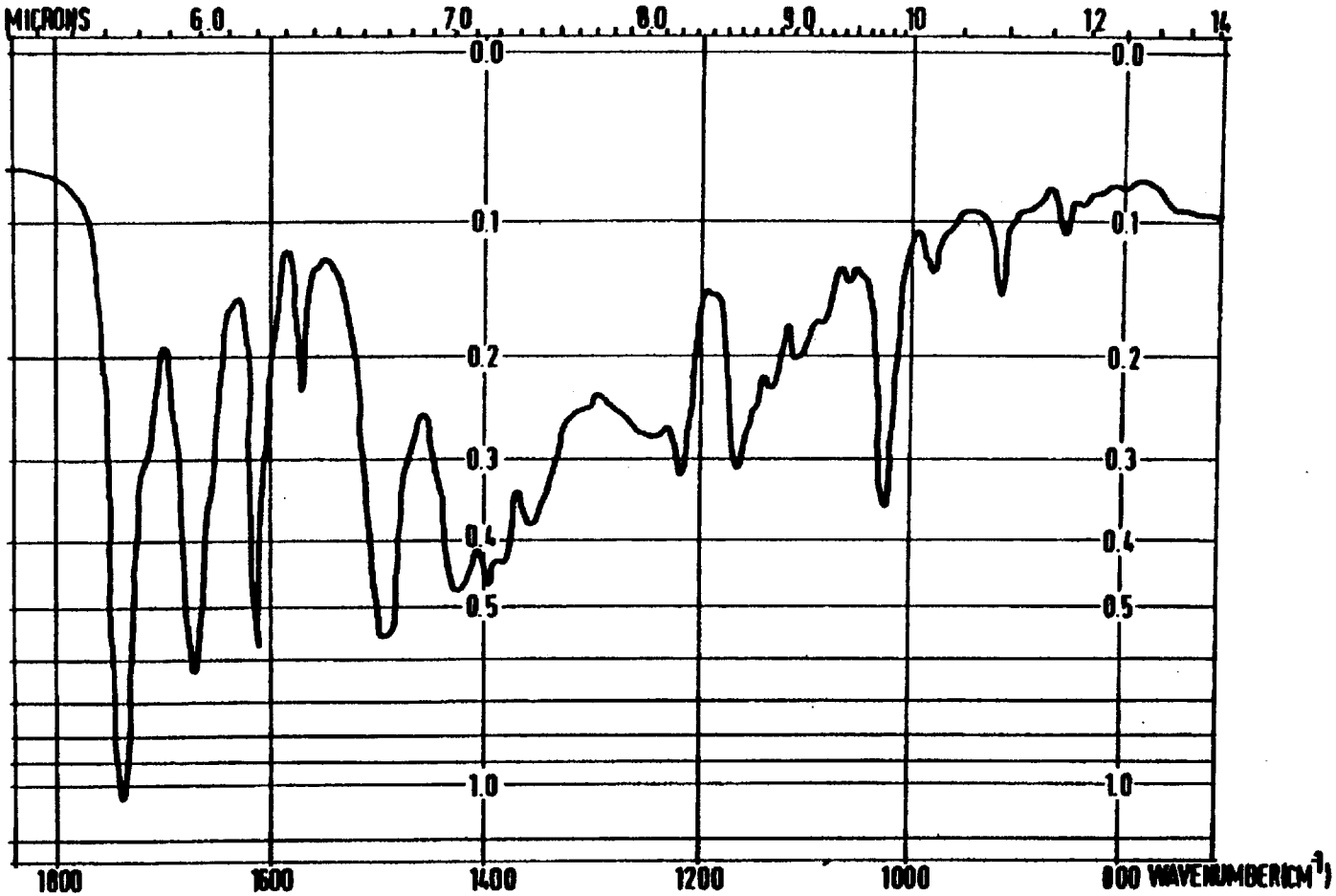

FIG. 2 (PART 1)
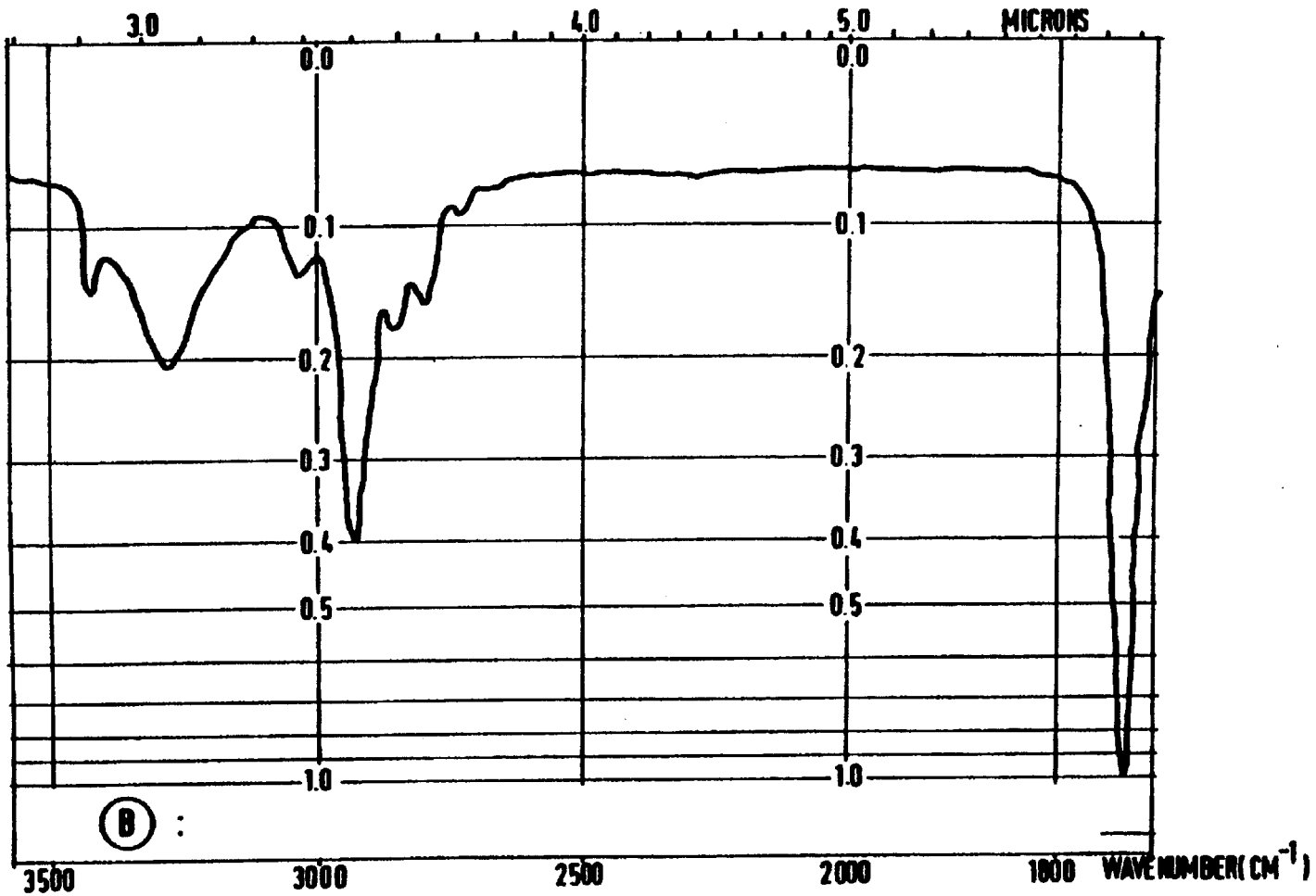

FIG. 2 (PART 2)
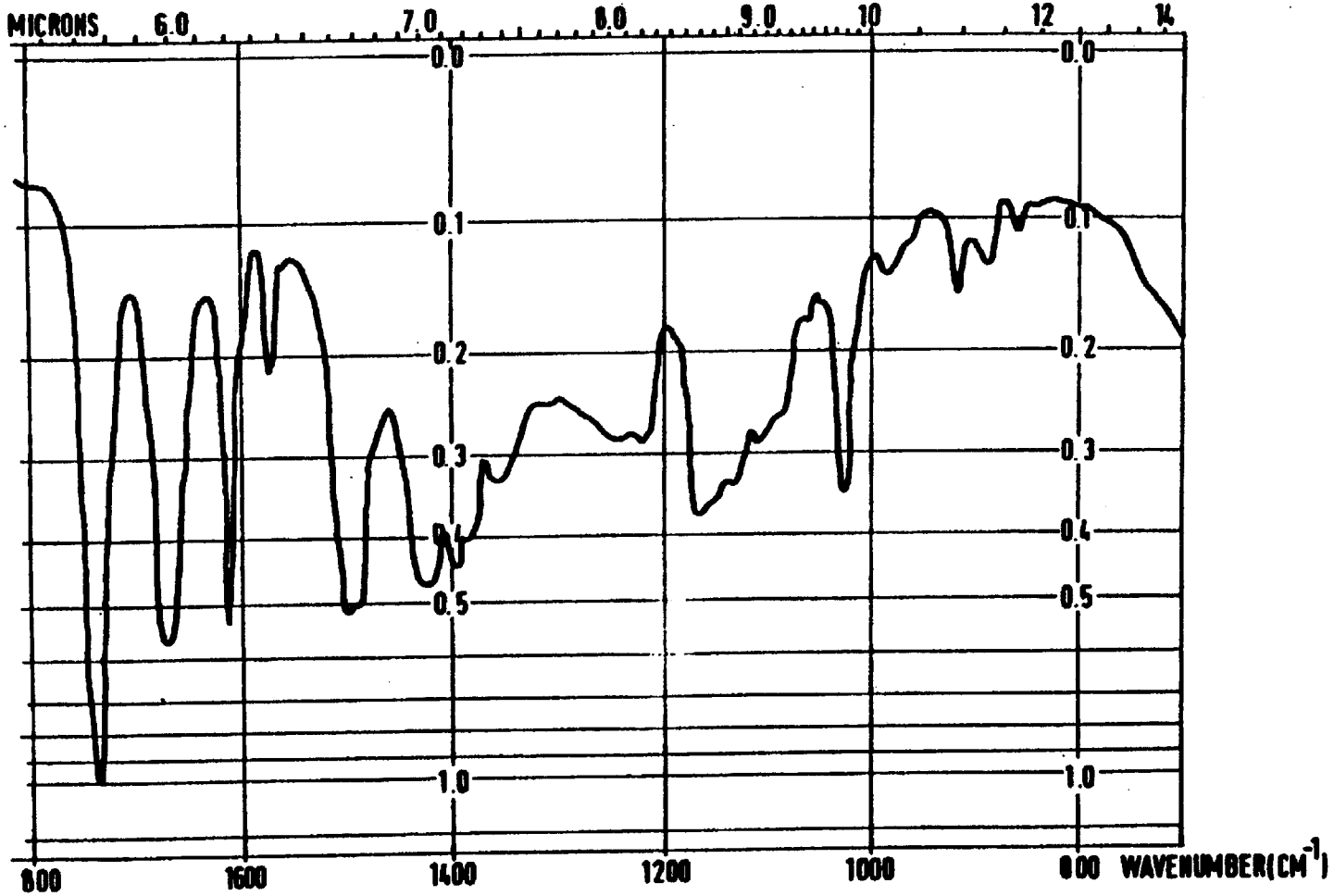

FIG. 3 (PART 1)
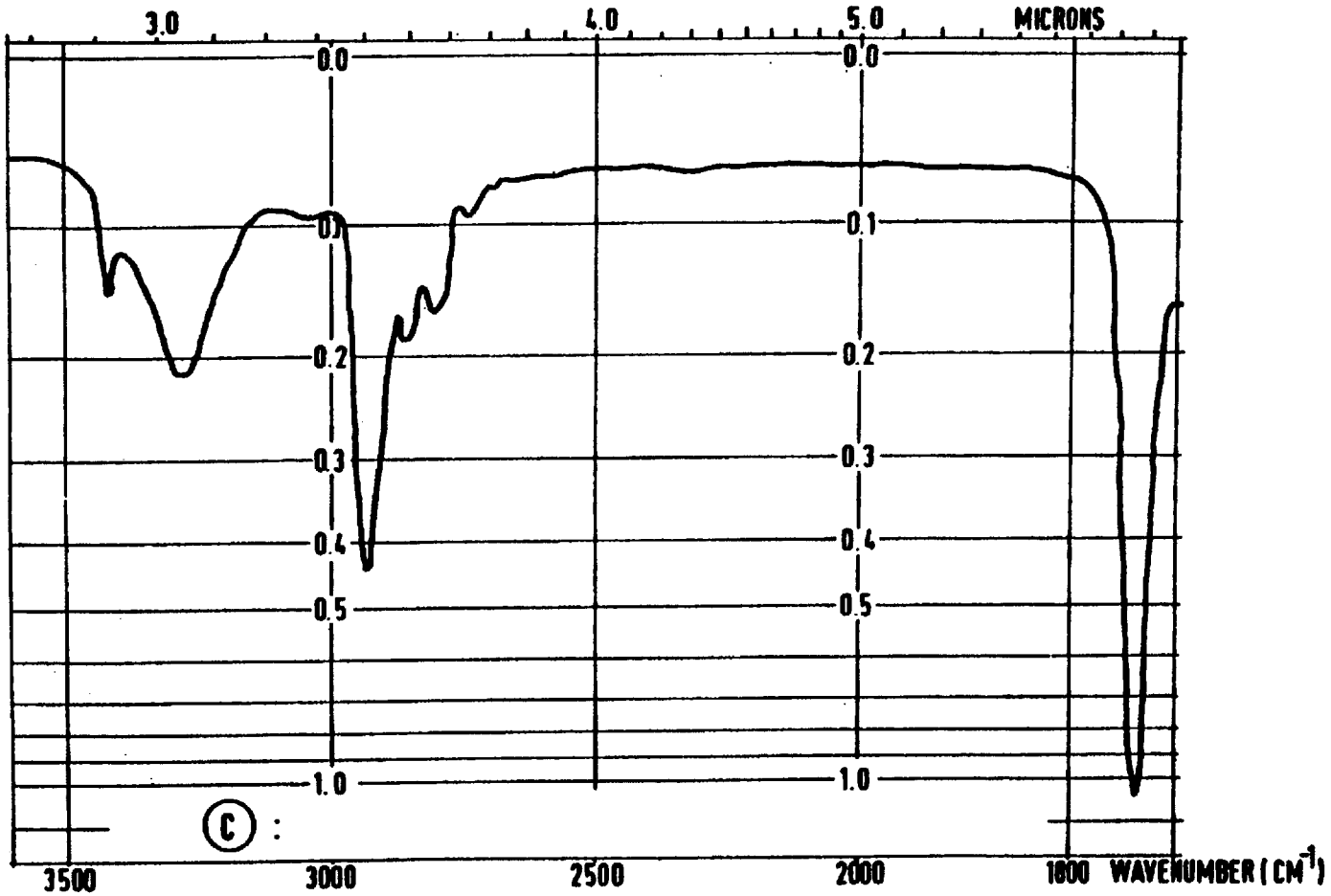

FIG. 3 (PART 2)
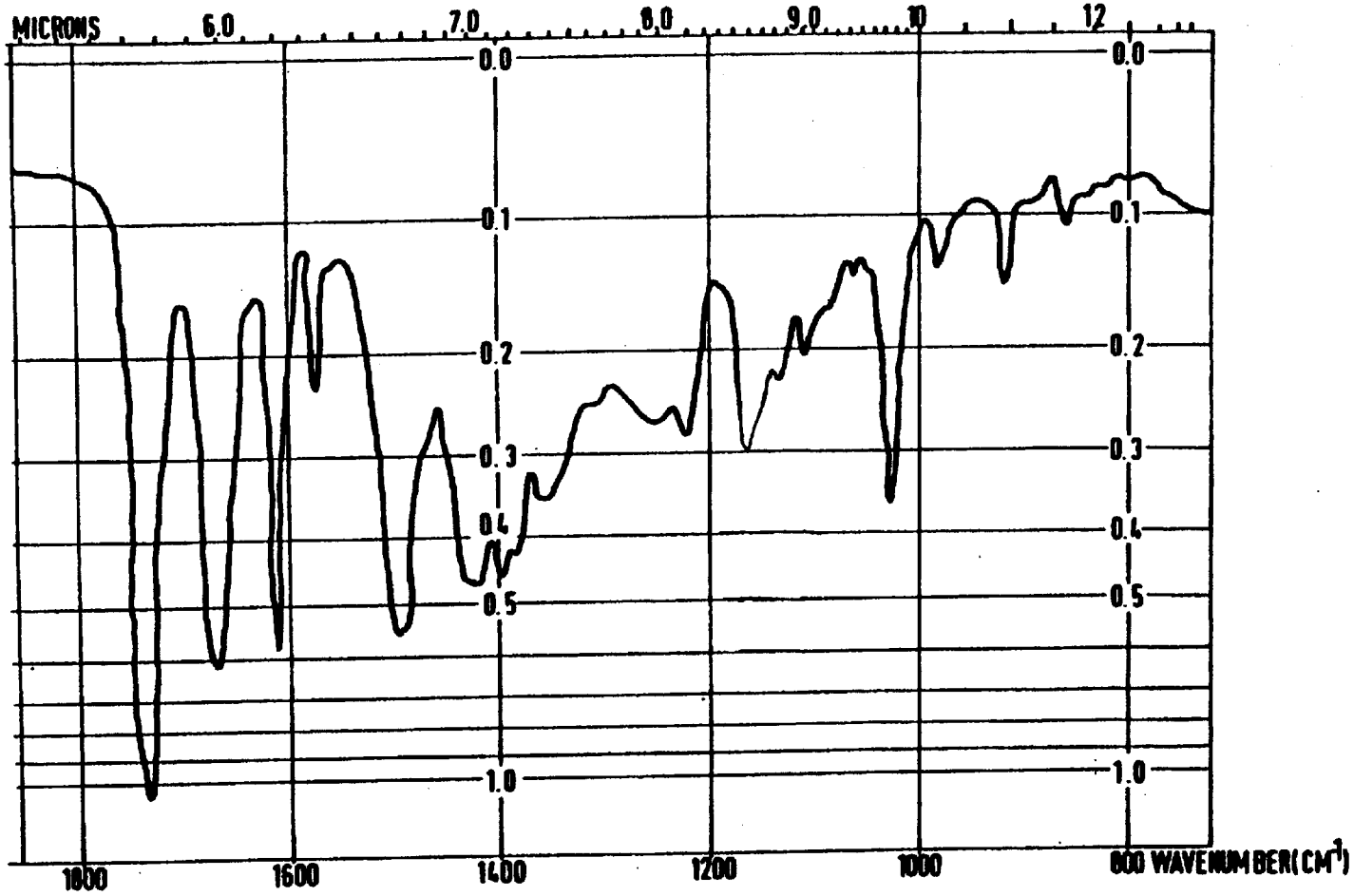

FIG. 4 (PART 1)
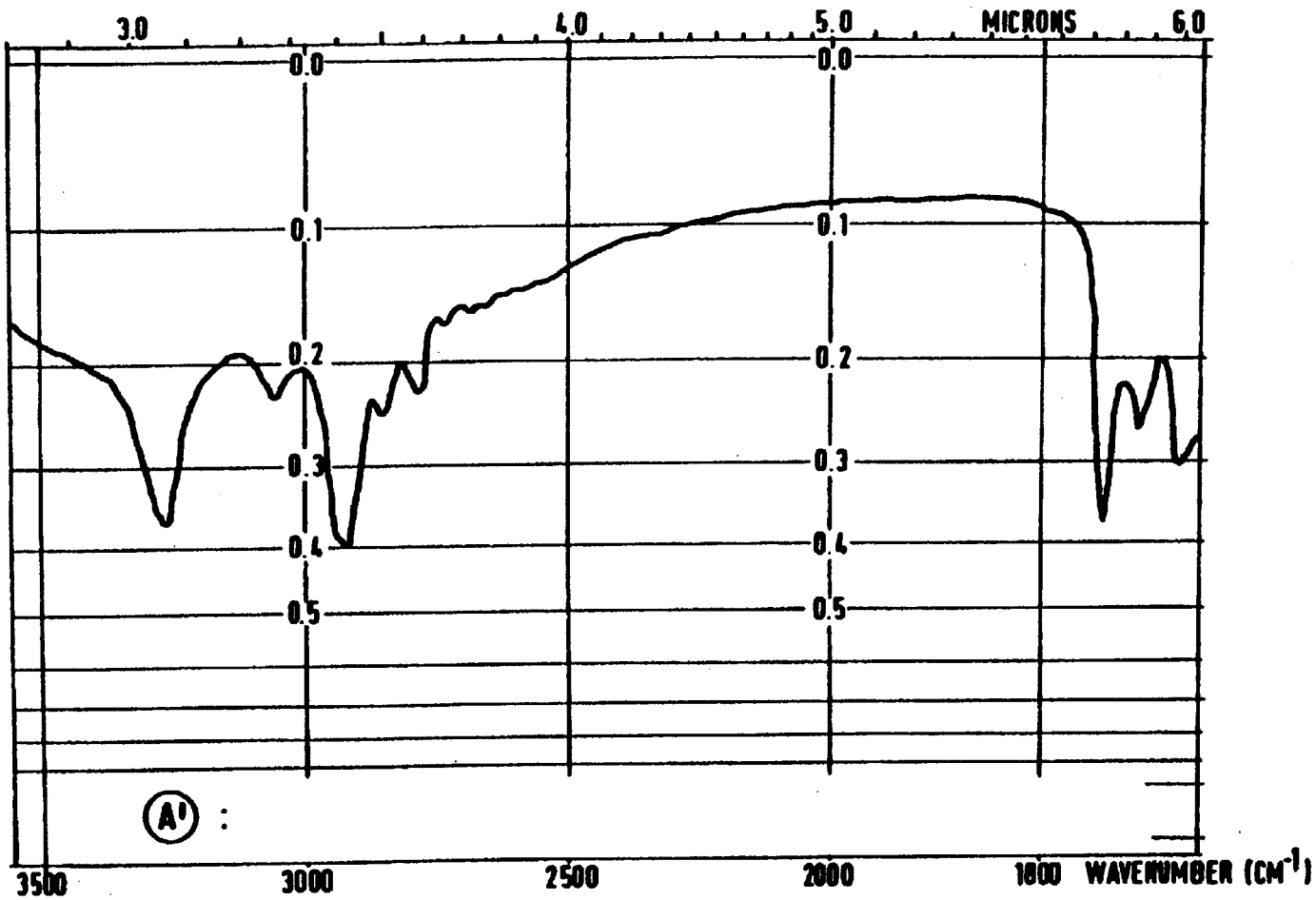

FIG. 4 (PART 2)
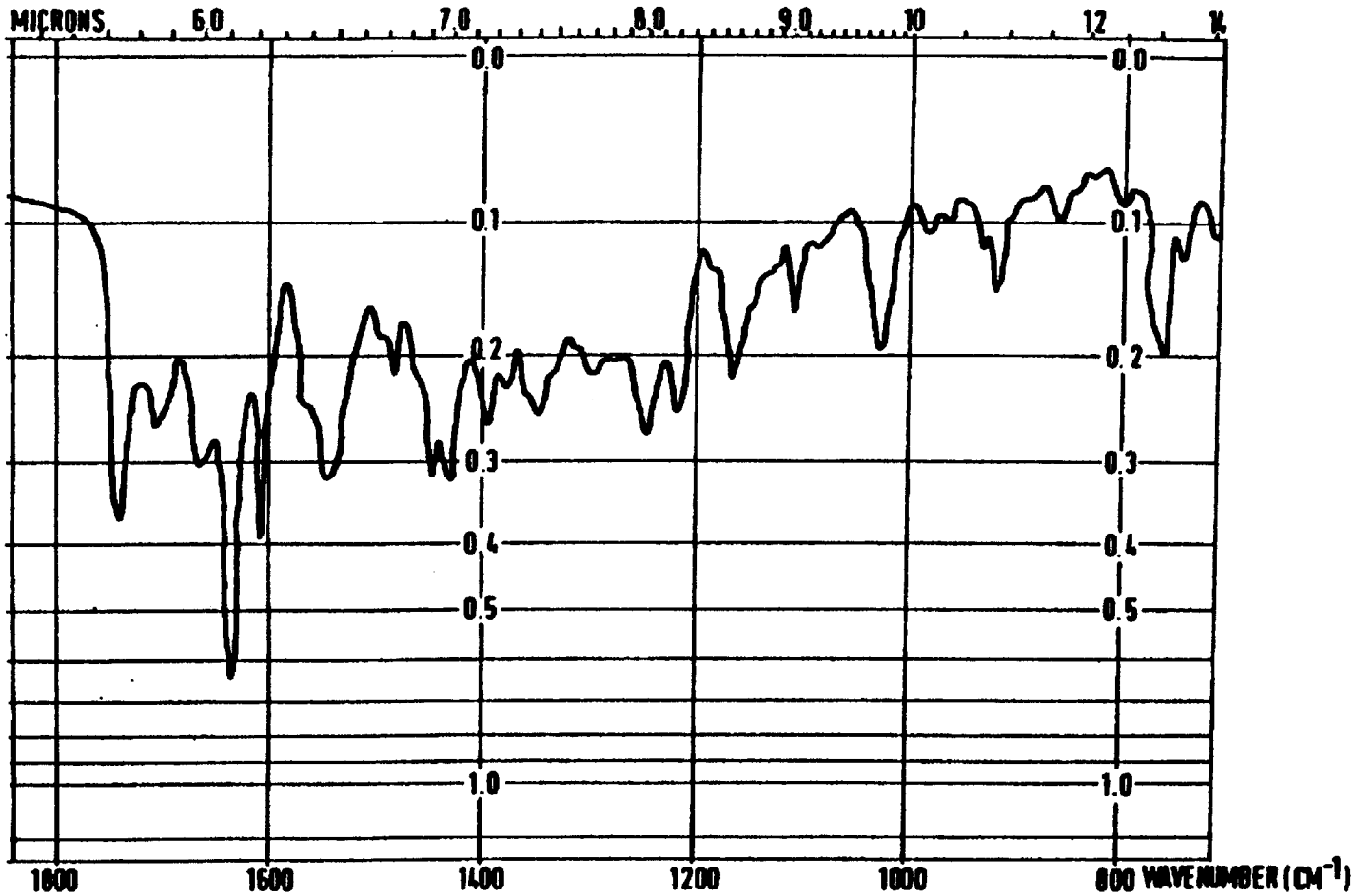

FIG. 5 (PART 1)
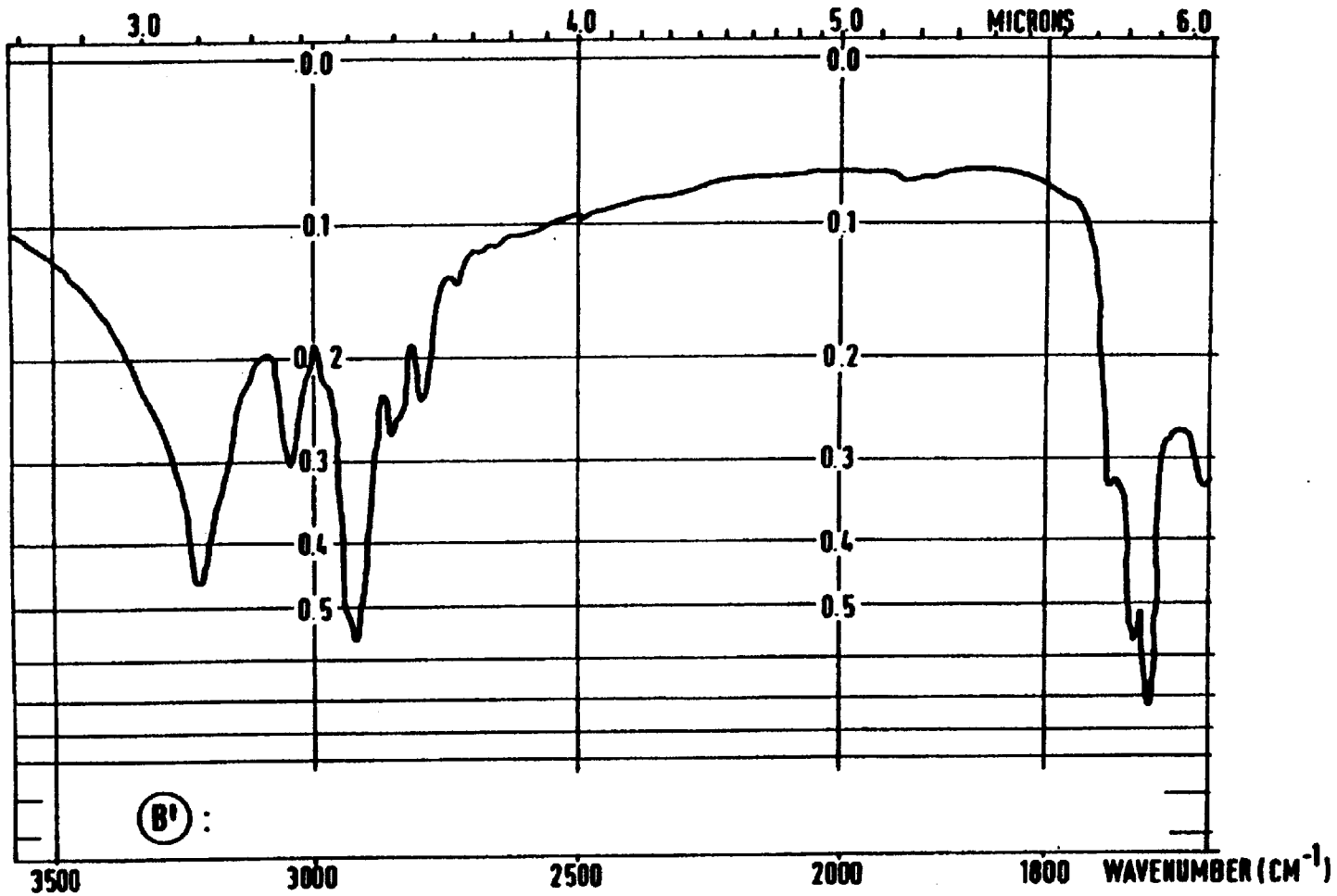

FIG. 5 (PART 2)
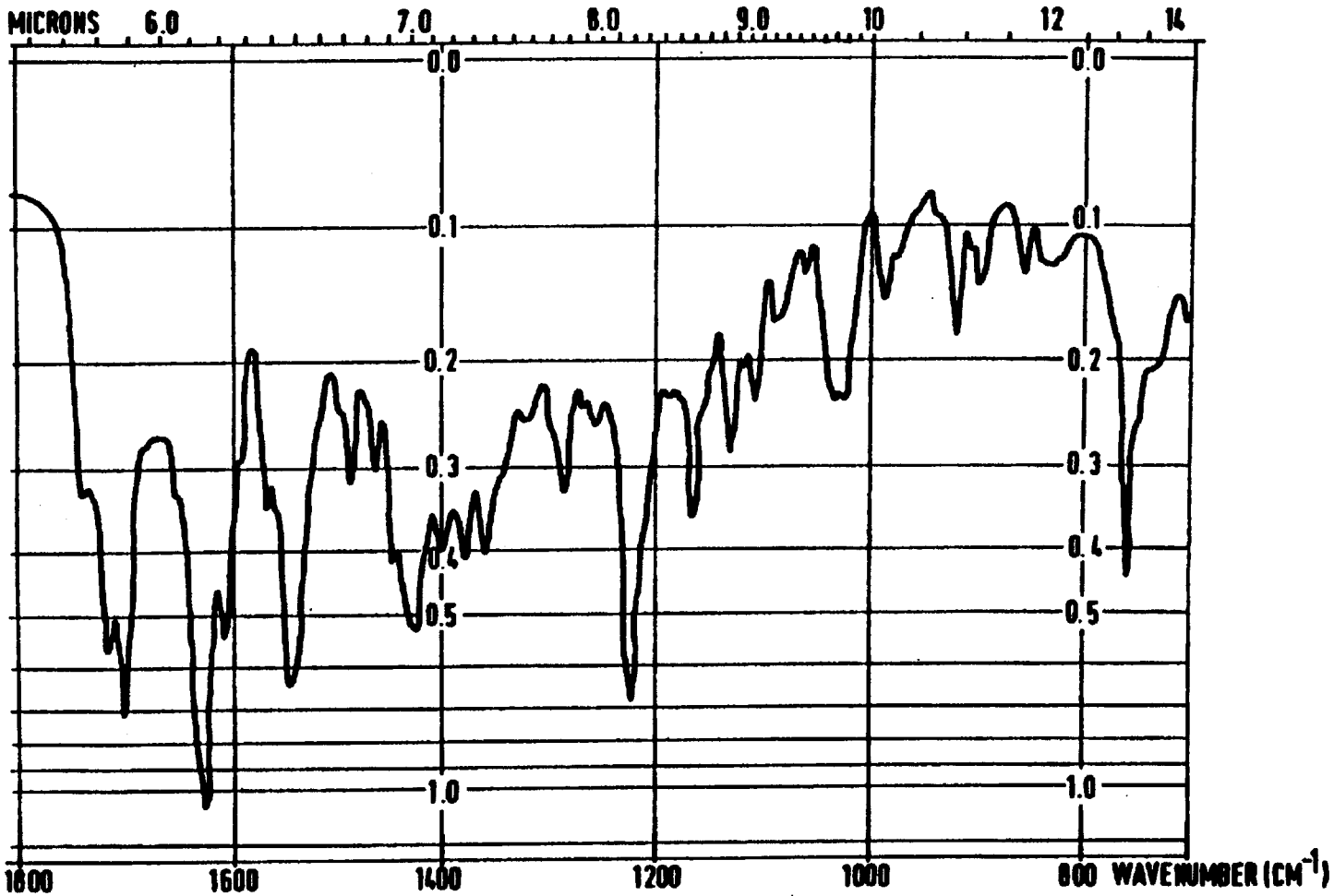

FIG. 6 (PART 1)
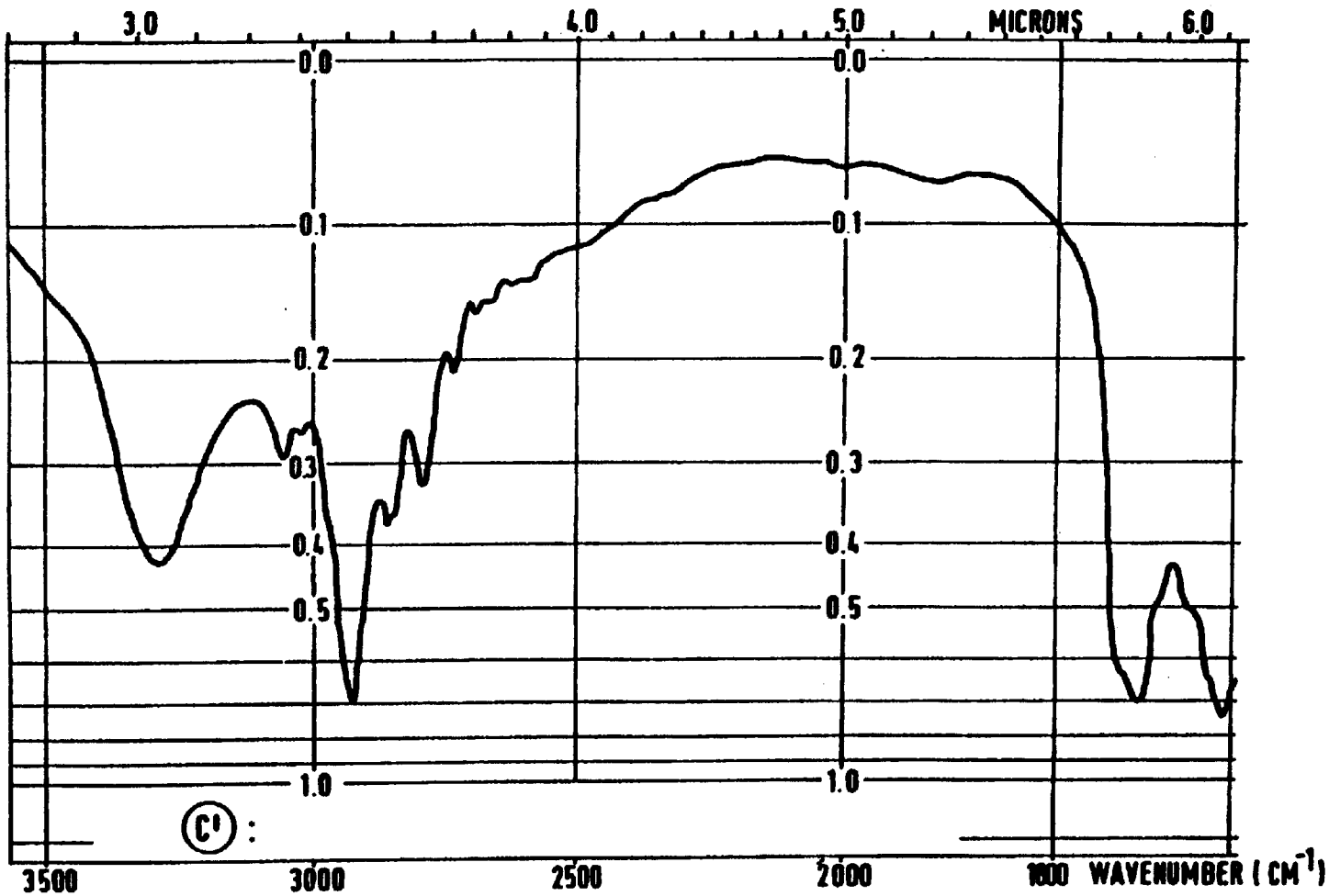

FIG. 6 (PART 2)
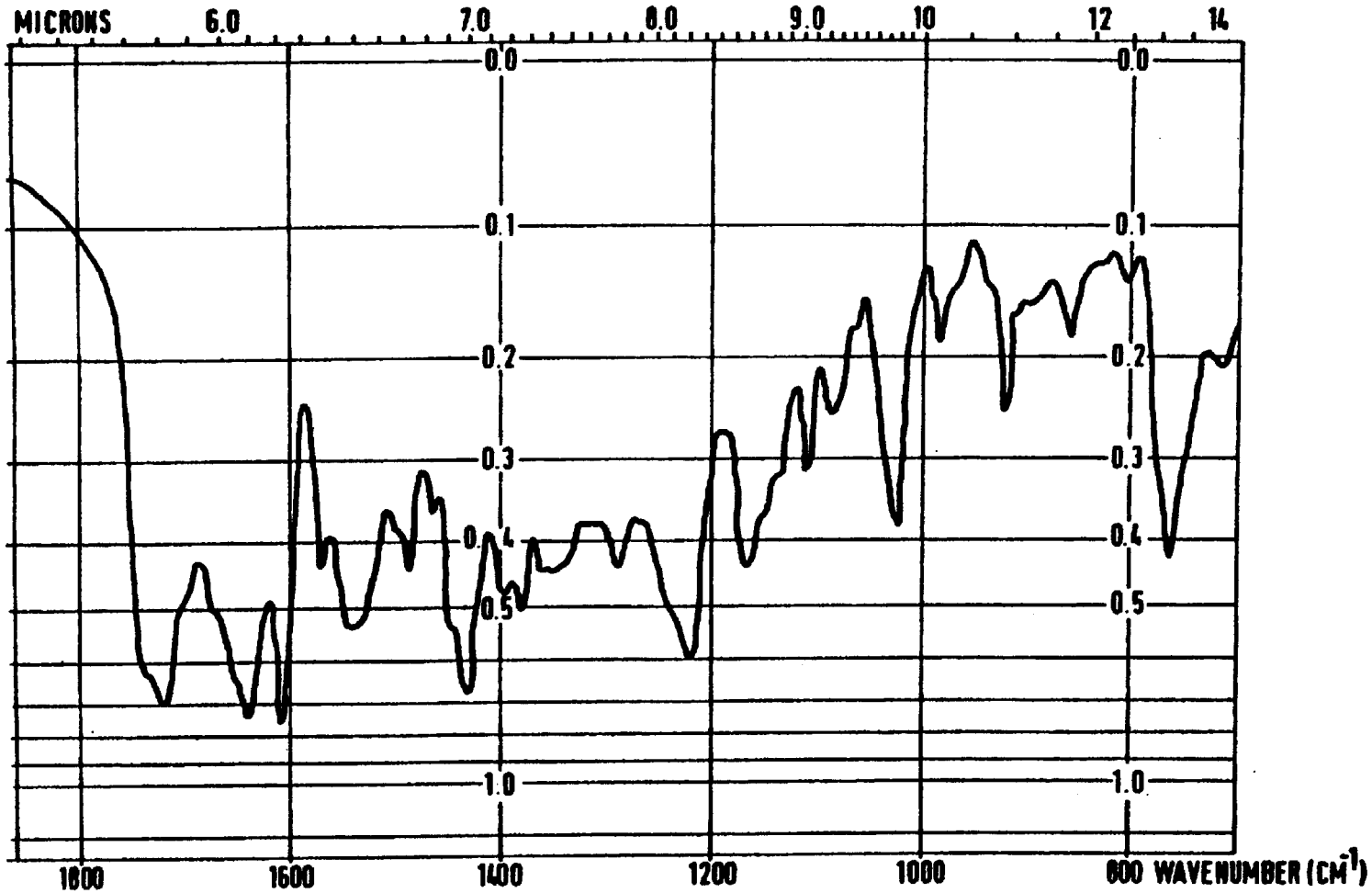

PHENYLACETIC ACID BENZYLAMIDES

Matter enclosed in heavy brackets [ ] appears in the original patent but forms no part of this reissue specification; matter printed in italics indicates the additions made by reissue.

This application is a reissue of Ser. No. 07/495,820 filed Mar. 19, 1990 now U.S. Pat. No. 5,216,167 which is a continuation of application Ser. No. 302,022, filed Jan. 25, 1989 (abandoned), which is a continuation-in-part of co-pending application Ser. No. 872,706 filed Jun. 10, 1986, (abandoned) which is a continuation-in-part of application Ser. No. 684,054 filed Dec. 20, 1984, now abandoned; and a continuation-in-part of co-pending application Ser. No. 878,921 filed Jun. 26, 1986 (abandoned).

This invention relates to novel phenylacetic acid benzylamides and their non-toxic salts, to methods of preparing these compounds, to pharmaceutical compositions containing them as active ingredients, and to a method of using them as hypoglycemics.

More particularly, the present invention relates to a novel class of compounds represented by the formula (I)

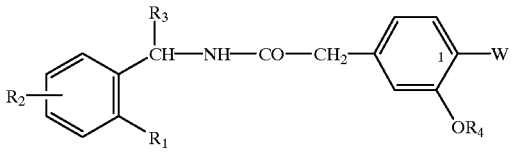

wherein:

$R_1$ represents an unbranched alkyleneimino group with 4 to 6 carbon atoms optionally mono- or di(allyl of 1 to 3 carbon atoms)-substituted;

$R_2$ represents a hydrogen or halogen atom or a methyl or methoxy group;

$R_3$ represents a hydrogen atom, an allyl group with 1 to 7 carbon atoms, a phenyl group optionally substituted by a halogen atom or a methyl or methoxy group, an alkyl group with 1 to 2 carbon atoms substituted by a hydroxy, alkoxy, alkanoyloxy, tetrahydrofuranyl, tetrahydropyranyl, cycloalkyl or phenyl group, in which the alkoxy part can contain from 1 to 3 carbon atoms, the alkanoyloxy part can contain 2 to 3 carbon atoms and the cycloalkyl part can obtain 3 to 7 carbon atoms, an alkenyl group with 3 to 6 carbon atoms, an alkynyl group with 3 to 5 carbon atoms, a carboxy group or an alkoxycarbonyl group with a total of 2 to 5 carbon atoms;

$R_4$ represents a hydrogen atom, a methyl, ethyl or allyl group; and

W represents a methyl, hydroxymethyl, formyl, carboxyl, alkoxycarbonyl, cyanomethyl, 2-cyanoethyl, 2-cyano-ethenyl, carboxymethyl, 2-carboxyethyl, 2-carboxyethenyl, alkoxycarbonylmethyl, 2-alkoxycarbonyl-ethyl or 2-alkoxycarbonylethenyl group, in which each alkoxy part can contain from 1 to 4 carbon atoms and can be substituted by a phenyl group; and when $R_3$ is other than hydrogen and/or the radical $R_1$ contains an optically active carbon atoms, the enantiomeres and the diastereomeres thereof or their mixtures; when W is carboxyl, a non-toxic salt thereof formed with an inorganic or organic base; or a non-toxic acid addition salt thereof formed by an inorganic or organic acid with the amino function in the $R_1$-position.

Specific embodiments of substituents $R_1$, $R_2$, $R_3$, $R_4$ and W are the following:

$R_1$: Pyrrolidino, piperidino, hexamethyleneimino, methyl-pyrrolidino, dimethyl-pyrrolidino, ethyl-pyrrolidino, 2-methyl-piperidino, 3-methyl-piperidino, 4-methyl-piperidino, 3,3-dimethyl-piperidino, cis-3,5-dimethyl-piperidino, trans-3,5-dimethyl-piperidino, ethyl-piperidino, diethyl-piperidino, methyl-ethyl-piperidino, propyl-piperidino, methyl-propyl-piperidino or isopropyl-piperidino.

$R_2$: Hydrogen, fluorine, chlorine, bromine, methyl or methoxy.

$R_3$: Hydrogen, methyl, ethyl, n-propyl, isopropyl, n-butyl, isobutyl, sec.butyl, tert.butyl, n-pentyl, 2-methyl-n-butyl, 3-methyl-n-butyl, 2,2-dimethyl-propyl-n-hexyl, 4-methyl-n-pentyl, n-heptyl, phenyl, fluorophenyl, chlorophenyl, bromophenyl, methylphenyl, methoxyphenol, 1-propen-1-yl, 2-methyl-1-propen-1-yl, 3-methyl-3-buten-2-yl, 2-propen-1-yl, 2-methyl-2-propen-1-yl, 2-buten-1-yl, 2-methyl-2-buten-1-yl, 3-methyl-2-buten-1-yl, 2-buten-1-yl, 2-methyl-3-buten-1-yl, 3-methyl-3-buten-1-yl, 2-hexen-1-yl, 1-propyn-1-yl, 2-propyn-1-yl, 2-butyn-1-yl, 2-pentyn-1-yl, hydroxymethyl, 1-hydroxy-ethyl, 2-hydroxy-ethyl, methoxymethyl, ethoxymethyl, n-propoxymethyl, isopropoxymethyl, 1-methoxy-ethyl, 2-methoxy-ethyl, 1-ethoxy-ethyl, 2-ethoxy-ethyl, 2-n-propoxy-ethyl, 2-isopropoxy-ethyl, acetoxymethyl, propionyloxymethyl, 1-acetoxy-ethyl, 2-acetoxy-ethyl, 1-propionyloxy-ethyl, 2-propionyloxy ethyl, tetrahydrofuran-2-yl-methyl, 2-(tetrahydrofuran-2-yl)-ethyl, tetrahydrofuran-3-yl-methyl, tetrahydropyran-2-yl-methyl, 2-(tetrahydropyran-2-yl)-ethyl, tetrahydropyran-3-yl-methyl, cyclopropyl-methyl, cyclobutyl-methyl, cyclopentylmethyl), cyclohexylmethyl, cycloheptylmethyl, 2-cyclopropylethyl, 2-cyclobutyl-ethyl, 2-cyclopenyl-ethyl, 2-cyclohexyl-ethyl, 2-cycloheptyl-ethyl, benzyl, 1-phenyl-ethyl, 2-phenyl-ethyl, carboxy, methoxycarbonyl, ethoxycarbonyl, n-propoxycarbonyl isopropoxycarbonyl, n-butoxycarbonyl, sec.butoxycarbonyl, isobutoxycarbonyl or tert.butoxy-carbonyl.

$R_4$: Hydrogen, methyl, ethyl, n-propyl, isopropyl, allyl.

W: Methyl, hydroxymethyl, formyl, carboxy, methoxycarbonyl, ethoxycarbonyl, n-propoxycarbonyl, isopropoxycarbonyl, n-butoxycarbonyl, sec.butoxycarbonyl, isobutoxycarbonyl, tert.butoxycarbonyl, benzyloxycarbonyl, 1-phenylethoxycarbonyl, 2-phenylethoxycarbonyl, 3-phenylpropoxycarbonyl, cyanomethyl, 2-cyano-ethyl, 2-cyano-ethenyl, carboxy-methyl, methoxycarbonylmethyl, ethoxycarbonyl-methyl, n-propoxycarbonylmethyl, n-butoxycarbonyl-methyl, tert.butoxycarbonylmethyl, 2-methoxycarbonyl-ethyl, 2-ethoxycarbonyl-ethyl, 2-n-propoxycarbonyl-ethyl, 2-isopropoxycarbonyl-ethyl, 2-n-butoxycarbonyl-ethyl, 2-tert.butoxycarbonyl-ethyl, 2-methoxycarbonyl-ethenyl, 2-ethoxycarbonyl-ethenyl, 2-n-propoxy-ethenyl or 2-tert.butoxycarbonylethenyl.

One subgeneric aspect is constituted by those compounds of the formula I wherein $R_1$ represents a pyrrolidino, piperidino, 4-methyl-piperidino, 3-methyl-piperidino, 3,3-dimethyl-piperidino, 3,5-dimethyl-piperidino or hexamethylene-imino group;

$R_2$ represents a hydrogen, fluorine or chlorine atom;

$R_3$ represents a hydrogen atom, an alkyl group with 1 to 6 carbon atoms, a phenyl, methyl-phenyl, chloro-phenyl, methoxy-phenyl, cyclopropylmethyl, cyclobutylmethyl, cyclopentylmethyl, cyclohexylmethyl, tetrahydrofuran-2-yl-methyl, tetrahydropyran-2-yl-methyl, propargyl, hydroxymethyl, ethoxymethyl, acetoxymethyl, propionyloxymethyl, carboxy, methoxycarbonyl, ethoxycargonyl or propoxycarbonyl group or a branched or unbranched alkenyl group with 3 or 4 carbon atoms;

$R_4$ represents a methyl, ethyl or allyl group; and

W represents a methyl hydroxymethyl, formyl, carboxyl, benzyloxycarbonyl, carboxymethyl, methoxycarbonylmethyl, ethoxycarbonylmethyl, cyanomethyl, 2-carboxy-ethyl, 2-ethoxycarbonyl-ethyl, 2-cyano-ethyl, 2-carboxy-ethenyl, 2-ethoxycarbonyl-ethenyl or 2-cyano-ethenyl group or an alkoxycarbonyl group with 1 to 4 carbon atoms in the alkoxy part; and when $R_3$ is other than hydrogen and/or $R_1$ represents the 3-methyl-piperidino group, the enantiomeres and the diastereomeres thereof or their mixtures; when W is carboxyl, a non-toxic salt thereof formed with an inorganic or organic base; or a non-toxic acid addition salt thereof formed by an inorganic or organic acid with the amino function in the $R_1$-position.

A preferred sugenus is constituted by those compounds of the formula I wherein $R_1$ represents a piperidino group;

$R_2$ represents a hydrogen atom;

$R_3$ represents an alkyl group with 1 to 6 carbon atoms, an alkenyl group with 3 to 4 carbon atoms, a phenyl, tetrahydropyran-2-yl-methyl, cyclopropylmethyl or cyclohexylmethyl group;

$R_4$ represents a methyl ethyl or allyl group; and

W represents a carboxyl, methoxycarbonyl, ethoxycarbonyl or cyanomethyl group; and the enantiomeres thereof or their mixtures; when W is carboxyl, a non-toxic salt thereof formed with an inorganic or organic base; or a non-toxic acid addition salt thereof formed by an inorganic or organic acid with the piperidino function.

An especially preferred subgenus is constituted by those compounds of the formula I wherein $R_1$ represents a piperidino group;

$R_2$ represents a hydrogen atom;

$R_3$ represents an alkyl group with 3 to 6 carbon atoms, an alkenyl group with 3 to 4 carbon atoms, a phenyl, cyclopropylmethyl or cyclohexylmethyl group;

$R_4$ represents a methyl or ethyl group; and

W represents a carboxyl group;

especially those compounds of the before mentioned preferred subgenus, wherein $R_3$ represents an alkyl group with 3 to 6 carbon atoms, a 2-methyl-1-propen-1-yl, cyclomethylpropyl or cyclohexylmethyl group; and the enantiomeres thereof or their mixtures; when W is carboxyl, a non-toxic salt thereof formed with an inorganic or organic base; or a non-toxic acid addition salt thereof formed by an inorganic or organic acid with the piperidino function.

A preferred subgenus of the before mentioned compounds are those, wherein $R_3$ represents a n-propyl, n-butyl, isobutyl, sec.butyl, n-pentyl, 2-methyl-1-propen-1-yl, cyclomethylpropyl or cyclohexylmethyl group, especially when $R_3$ represents a n-propyl, n-butyl, isobutyl, sec.butyl or n-pentyl group; and the enantiomeres thereof or their mixtures; when W is carboxyl, a non-toxic salt thereof formed with an inorganic or organic base; or a non-toxic acid addition salt thereof formed by an inorganic or organic acid with the piperidino function.

According to the invention, the new compounds are obtained by the following methods:

a) reacting an amine of formula (II)

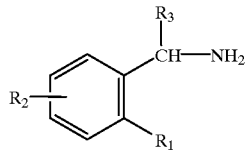

wherein $R_1$ to $R_3$ are defined as hereinbefore, with a carboxylic acid of formula (III)

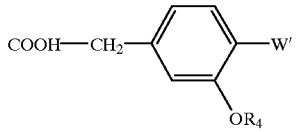

wherein $R_4$ is defined as hereinbefore and

W' has the meanings given for W hereinbefore, in which any carboxy group contained in the group W can be protected by a protecting group, or with the reactive derivatives thereof optionally prepared in the reaction mixture, if necessary with subsequent splitting off of any protecting group used.

Examples of reactive derivatives of a compound of formula III which can be used include the esters thereof, such as the methyl, ethyl or benzyl esters, the thioesters such as the methylthio or ethylthioesters, the halides such as the acid chloride, the anhydride or imidazolides thereof.

The reaction is appropriately carried out in a solvent such as methylene chloride, chloroform, carbon tetrachloride, ether, tetrahydrofuran, dioxan, benzene, toluene, acetonitrile or dimethyl formamide, optionally in the presence of an acid-activating agent or a dehydrating agent, e.g., in the presence of ethyl chloroformate, thionyl chloride, phosphorus trichloride, phosphorus pentoxide, N,N'-dicyclohexylcarbodiimide. N,N'-dicyclohexylcarbodiimide/N-hydroxysuccinimide, N,N'-carbonyldiimidazole or N,N'-thionyldiimidazole or triphenylphosphine/carbon tetrachloride, or an agent which activates the amino group, e.g. phosphorus trichloride, and optionally in the presence of an inorganic base such as sodium carbonate or a tertiary organic base such as triethylamine, or pyridine, which can simultaneously be used as solvent, at temperatures of between −25° C. and 250° C., but preferably at temperatures of between −10° C. and the boiling temperature of the solvent used. The reaction can also be carried out without a solvent and furthermore any water formed during the reaction can be removed by azeotropic distillation, e.g. by heating with toluene using a water separator, or by adding a drying agent such as magnesium sulphate or a molecular sieve.

If necessary, the subsequent splitting off of a protecting group is preferably carried out by hydrolysis, conveniently either in the presence of an acid such as hydrochloric, sulphuric, phosphoric or trichloroacetic acid or in the presence of a base such as sodium hydroxide or potassium hydroxide in a suitable solvent such as water, methanol, methanol/water, ethanol, ethanol/water, water/isopropanol or water/dioxan at temperatures of between −10° and 120° C., e.g. at temperatures of between ambient temperature and the boiling temperature of the reaction mixture.

A tert.butyl group used as protecting group can also be split off thermally, optionally in an inert solvent such as methylene chloride, chloroform, benzene, toluene, tetrahydrofuran or dioxan and preferably in the presence of a catalytic quantity of an acid such as p-toluenesulphonic acid, sulphuric, phosphoric or polyphosphoric acid.

Furthermore, a benzyl group used as protecting group can also be split off hydrogenolytically in the presence of a hydrogenation catalyst such as palladium/charcoal in a suitable solvent such as methanol, ethanol, ethanol/water, glacial acetic acid, ethyl acetate, dioxan or dimethylformamide.

b) In order to prepare compounds of formula I wherein $R_3$ represents a carboxy or alkoxycarbonyl group and W has the meanings given hereinbefore or W represents a carboxy, carboxymethyl, 2-carboxy-ethyl, 2-carboxy-ethenyl, alkoxycarbonyl, alkoxycarbonylmethyl, 2-alkoxycarbonyl-ethyl or 2-alkoxycarbonyl-ethenyl group and $R_3$ has the meanings given hereinbefore:

Hydrolysis, thermolysis, hydrogenolysis or alcoholysis of a compound of formula (IV)

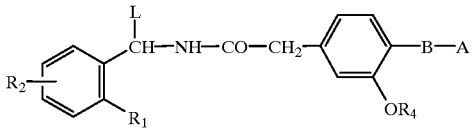

wherein $R_1$, $R_2$ and $R_4$ are as hereinbefore defined,

B represents a bond, a methylene, ethylene or ethylene group,

A and L each represent a nitrile group or a group which can be converted into a carboxy group by hydrolysis, thermolysis or hydrogenolysis and L additionally has the meanings given for $R_3$ hereinbefore.

Examples of hydrolysable groups include functional derivatives of the carboxy group and the unsubstituted or substituted amides, esters, thioesters, ortho esters, iminoethers, amidines or anhydrides thereof, the nitrile group, the tetrazolyl group, an optionally substituted 1,3-oxazol-2-yl or 1,3-oxazolin-2-yl group, examples of thermolytically cleavable groups include esters with tertiary alcohols, e.g., the tert.butyl ester, examples of hydrogenolytically cleavable groups include aralkyl groups, e.g. the benzyl group, and examples of alcoholytically cleavable groups include the cyano group.

The hydolysis is conveniently carried out either in the presence of an acid such as hydrochloric sulphuric, phosphoric or trichloroacetic acid or in the presence of a base such as sodium hydroxide or potassium hydroxide in a suitable solvent such as water, water/methanol, ethanol, water/ethanol, water/isopropanol or water/dioxan at temperatures of between −10 and 120° C., e.g. at temperatures of between ambient temperature and the boiling temperature of the reaction mixture, and the alcoholysis of a cyano group is preferably effected in an excess of the corresponding alcohol such as methanol, ethanol or propanol and in the presence of an acid such as hydrochloric acid at elevated temperatures, e.g. at the boiling temperature of the reaction mixture.

If A and/or L in a compound of formula IV represents a nitrile or aminocarbonyl group, these groups can be converted into a corresponding carboxy compound by means of 100% phosphoric acid at temperatures of between 100 and 180° C., preferably at temperatures of between 120 and 160° C., or with a nitrite, e.g., sodium nitrite, in the presence of an acid such as sulphuric acid, the latter conveniently being used as solvent as well, at temperature of between 0° and 50° C.

If A and/or L in a compound of formula IV represents the tert butyloxycarbonyl group for example, the tert.butyl group can also be split off thermally, optionally in an inert solvent such as methylene chloride, chloroform, benzene, toluene, tetrahydrofuran or dioxan and preferably in the presence of a catalytic quantity of an acid such as p-toluenesulphonic, sulphuric, phosphoric or polyphosphoric acid, preferably at the boiling temperature of the solvent used, e.g. at temperatures of between 40 and 100° C. If A and/or L in a compound of formula IV represents the benzyloxycarbonyl group for example, the benzyl group can also be split off hydrogenolytically in the presence of a hydrogenation catalyst such as palladium/charcoal in a suitable solvent such as methanol, ethanol, methanol/water, ethanol/water, glacial acetic acid, ethyl acetate, dioxan or dimethylformamide, preferably at temperatures of between 0 and 50° C., e.g. at ambient temperature and under a hydrogen pressure of from 1 to 5 bar. During hydrogenolysis, a compound containing halogen can simultaneously be dehalogenated, any double or triple bonds present can be hydrogenated and any benzyloxycarbonyl group present can be converted into a carboxy group.

c) In order to prepare compounds of formula I wherein $R_4$ represents a hydrogen atom:

Splitting off a protecting group from a compound of formula (V)

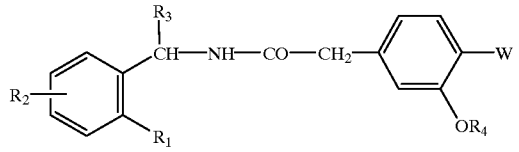

wherein $R_1$ to $R_3$ and W are as hereinbefore defined and $R_5$ represents a protecting group for a hydroxy group.

Examples of protecting groups for $R_5$ include, for example, an alkyl, aralkyl, aralkyl or trialkylsilyl group, e.g. the methyl, ethyl, propyl, allyl, benzyl or trimethylsilyl group.

Depending on the protecting group used, the protecting groups mentioned above can be split off either by hydrolysis or by hydrogenolysis, optionally in a suitable solvent, at temperatures of between −78 and 250° C.

For example, ether splitting is carried out in the presence of an acid such as hydrochloric, hydrobromic or sulphuric acid, boron tribromide, aluminium trichloride or pyridine hydrochloride, conveniently in a suitable solvent such as methylene chloride, glacial acetic acid or water or in mixtures thereof at temperatures of between −78° and 250° C. The ether splitting is carried out in the presence of a proton acid conveniently at temperatures of between 0° and 150° C., preferably at temperatures of between 50° and 150° C. or with a lewis acid preferably in a solvent such as methylene chloride at temperatures of between −78° and 20° C.

For example, any protecting group used such as a benzyl group can be split off hydrogenolytically with hydrogen in the presence of a hydrogenation catalyst such as palladium/charcoal in a suitable solvent such as methanol, ethanol, ethanol/water, glacial acetic acid, ethyl acetate, dioxin or dimethylformamide, preferably at ambient temperature, for example, and under a hydrogen pressure of from 1 to 5 bar.

d) In order to prepare compounds of formula I wherein $R_4$ represents methyl, ethyl or allyl group:

Reacting a compound of formula (VI)

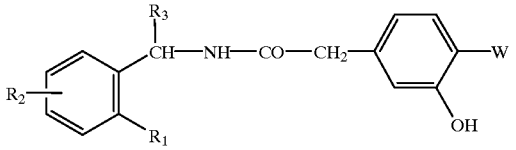

wherein $R_1$ to $R_3$ and W are as hereinbefore defined, with a compound of formula $$X—R_6 \quad \text{(VII)}$$

wherein $R_6$ represents methyl, ethyl or allyl group

X represents a nucleophilically exchangeable group such as a halogen atom, a sulphonyloxy group or, together with the adjacent hydrogen atom, a diazo group, if $R_6$ represents an alkyl group with 1 to 3 carbon atoms, if necessary with subsequent hydrolysis.

The reaction is conveniently carried out with a corresponding halide, sulphonic acid ester, sulphuric acid diester or diazoalkane, e.g. with methyl iodide, dimethyl sulphate, ethyl bromide, diethyl sulphate, allyl bromide, ethyl p-toluenesulphonate, or diazomethane, optionally in the presence of a base such as sodium hydride, potassium carbonate, sodium hydroxide, potassium tert.butoxide or triethylamine in a suitable solvent such as acetone, diethylether, tetrahydrofuran, dioxan or dimethylformamide at temperatures of between 0° and 100° C., preferably at temperatures of between 20° and 50° C. If in a compound of formula VI $R_3$ represents a carboxy group and/or W represents a carboxy, carboxymethyl, 2-carboxy-ethyl or 2-carboxy-ethenyl group, this compound can simultaneously be converted into the corresponding ester compound. A compound thus obtained is, if necessary by cleaving the ester group, converted into the desired compound of formula I.

The cleaving of the ester group is carried out hydrolytically, conveniently either in the presence of an acid such as hydrochloric, sulphuric, phosphoric or trichloroacetic acid or in the presence of a base such as sodium hydroxide or potassium hydroxide in a suitable solvent such as water, methanol, methanol/water, ethanol, ethanol/water, water/isopropanol or water/dioxan at temperatures of between −10° and 120° C., e.g. at temperatures of between ambient temperature and the boiling point of the reaction mixture.

e) In order to prepare compounds of formula I wherein W represents a cyanomethyl or 2-cyano-ethyl group:

Reacting a compound of formula (VIII)

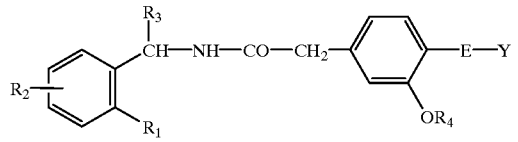

wherein $R_1$ to $R_4$ are as hereinbefore defined,

E represents a methylene or ethylene group and

Y represents a nucleophilically exchangeable group such as a halogen atom or a sulphonyloxy group, e.g. a chlorine, bromine or iodine atom or a methanesulphonyloxy or p-toluenesulphonyloxy group, with an alkali metal cyanide such as sodium or potassium cyanide.

The reaction is conveniently carried out in a suitable solvent such as dimethylsulphoxide or dimethylformamide at temperatures of between 0° and 100° C., preferably at temperatures of between 20° and 50° C., or in a two-phase system such as methylene chloride/water in the presence of a phase transfer catalyst such as benzyl-tributyl-ammonium chloride at temperatures of between 10° and 100° C., preferably at temperatures of between 20° and 50° C.

f) In order to prepare compounds of formula I wherein W represents a cyanomethyl, 2-cyano-ethyl or 2-cyano-ethenyl group:

Dehydration of a compound of formula (IX)

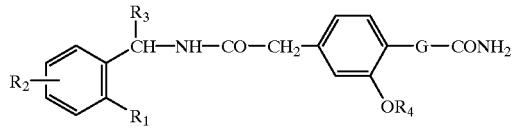

wherein $R_1$ to $R_4$ are as hereinbefore defined and

G represents a methylene, ethylene or ethylene group.

The dehydration is carried out with a water-cleaving agent such as phosphorus pentoxide, phosphorus oxychloride, triphenylphosphine/carbon tetrachloride or p-toluenesulphonic acid chloride, optionally in a solvent such as methylene chloride, acetonitrile or pyridine at temperatures of between 0° and 100° C., preferably at temperatures of between 20° C. and 180° C.

g) In order to prepare compounds of formula I wherein W represents a 2-cyano-ethenyl, 2-carboxy-ethenyl or 2-alkoxycarbonyl-ethenyl group:

Reacting a compound of formula (X)

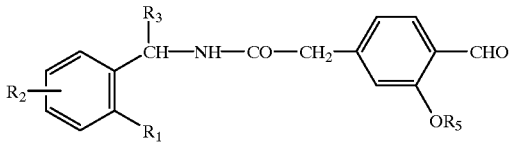

wherein $R_1$ to $R_4$ are as hereinbefore defined, with a corresponding acetic acid derivative of formula $$Z—CH_2—Q \quad (XI)$$

wherein Q represents a carboxy, alkoxycarbonyl or cyano group and

Z represents a hydrogen atom, an alkoxycarbonyl, dialkylphosphono or triphenylphosphonium halide group, optionally with subsequent hydrolysis and/or decarboxylation.

The reaction is conveniently carried out in a solvent such as diethylether, tetrahydrofuran, 1,2-dimethoxyethane, dioxan, dimethylformamide, toluene or pyridine in the presence of a base as condensation agent such as sodium carbonate, sodium hydride, potassium tert.butoxide or piperidine at temperatures of between 0° and 100° C., preferably at temperatures of between 20° and 80° C.

The subsequent hydrolysis and/or decarboxylation is conveniently carried out either in the presence of an acid such as hydrochloric, sulphuric, phosphoric or trichloroacetic acid or in the presence of a base such as sodium hydroxide or potassium hydroxide in a suitable solvent such as water, water/methanol, ethanol, water/ethanol, water/isopropanol or water/dioxan at temperatures of between −10° C. and 120° C., e.g. at temperatures of between ambient temperature and the boiling temperature of the reaction mixture.

h) In order to prepare compounds of formula I wherein W represents a 2-carboxy-ethyl, 2-alkoxycarbonyl-ethyl or 2-cyano-ethyl group:

Reduction of a compound of formula (XII)

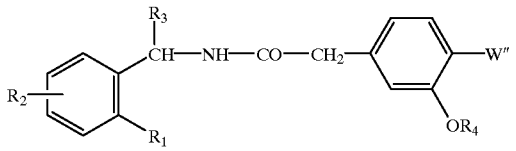

wherein $R_1$ to $R_4$ are as hereinbefore defined and

W" represents a 2-carboxy-ethenyl, 2-alkoxycarbonyl-ethenyl or 2-cyano-ethenyl group.

The reduction is preferably carried out in a suitable solvent such as methanol, ethanol, isopropanol, ethyl acetate, dioxan, tetrahydrofuran, dimethylformamide, benzene or benzene/ethanol with hydrogen in the presence of a suitable hydrogenation catalyst such as palladium/charcoal, Raney nickel or tris-#[triphenylphosphine#*-rhodium(I) chloride at temperatures of between 0° and 100° C., under a hydrogen pressure of from 1 to 5 bar or, if W" contains a cyano group, with nascent hydrogen, e.g. with magnesium/methanol, or with a copper hydride complex, e.g. with the complex prepared from copper bromide, sodium bis(2-methoxyethoxy)-aluminium hydride and sec.butanol, at temperatures of between −78° and 50° C. Other groups can be reduced at the same time, e.g. a benzyloxy group can be reduced to the hydroxy group, an alkenyl or alkynyl group can be reduced to the corresponding alkyl group or a formyl group can be reduced to the hydroxymethyl group, or they can be replaced by hydrogen atoms, e.g. a halogen atom can be replaced by a hydrogen atom.

i) In order to prepare compounds of formula I wherein $R_3$ represents an alkyl group with 1 or 2 carbon atoms substituted by an alkoxy or alkanoyloxy group:

Reacting a compound of formula (XIII)

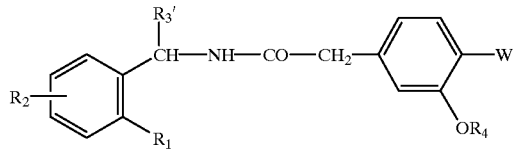

wherein $R_1$, $R_2$, $R_4$ and W are as hereinbefore defined and $R_3'$ represents an alkyl group with 1 or 2 carbon atoms substituted by a hydroxy group, with a compound of formula $$U—R_7 \quad (XIV)$$

wherein $R_7$ represents an alkyl group with 1 to 3 carbon atoms or an acetyl or propionyl group and U represents a nucleophilically exchangeable group such as a halogen atom, a sulphonyloxy group, an acetoxy or propionyloxy group or, together with the adjacent hydrogen atom, represents a diazo group if $R_7$ represents an alkyl group with 1 to 3 carbon atoms, optionally with subsequent hydrolysis.

The reaction is conveniently carried out with a corresponding halide, anhydride, sulphonic acid ester, sulphuric acid diester or diazoalkane, e.g. with methyl iodide, dimethyl sulphate, ethyl iodide, diethyl sulphate, n-propyl iodide, isopropyl bromide, acetyl chloride, acetic hydride, propionic acid chloride propionic acid anhydride, ethyl p-toluenesulphonate or isopropylmethanesulphonate, optionally in the presence of a base such as sodium hydride, potassium carbonate, sodium hydroxide, potassium tert.butoxide or triethylamine, or with diazomethane, optionally in the presence of a Lewis acid, e.g. boron trifluoride, preferably in a suitable solvent such as acetone, diethylether, tetrahydrofuran, dioxan, pyridine or dimethylformamide at temperatures of between 0° and 100° C., preferably at temperatures of between 20° and 50° C., in which an anhydride used as the acylating agent can simultaneously also be used as solvent.

If in a compound of formula XIII W represents a carboxy, carboxymethyl, 2-carboxy-ethyl or 2-carboxyethenyl group and/or $R_4$ represents a hydrogen atom, this can simultaneously be converted into the corresponding ester and/or ether compound.

k) In order to prepare compounds of formula I wherein $R_3$ represents an alkoxycarbonyl group:

Reacting a compound of formula (XV)

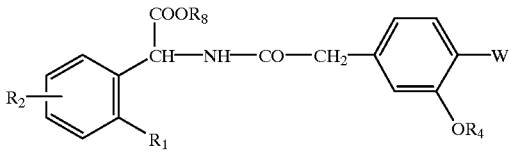

wherein $R_1$, $R_2$, $R_4$ and W are as hereinbefore defined and $R_8$ represents a hydrogen atom or alkali metal atom, or the reactive derivatives thereof optionally prepared in the reaction mixture, with a compound of formula $$T—R_9 \quad (XVI)$$

wherein $R_9$ represents an alkyl group with 1 to 4 carbon atoms and

T represents a hydroxy group or a nucleophilically exhangeable group such as a halogen atom or a sulphonyloxy group, or together with the adjacent hydrogen atom of the group $R_9$ represents a diazo group, optionally followed by hydrogenolysis if W contains a benzyloxycarbonyl group.

An example of a reactive derivative of a compound of formula XV is the imidazolide thereof.

The reaction is conveniently carried out in the corresponding alcohol as solvent or in a suitable solvent such as methylene chloride, chloroform, ether, tetrahydrofuran, dioxan, dimethylformamide, benzene or toluene, optionally in the presence of an acid-activating agent or a dehydrating agent, e.g. in the presence of hydrogen chloride, sulphuric acid, ethyl chloroformate, thionylchloride, carbon tetrachloride/triphenylphosphine, carbonyldiimidazole or N,N'-dicyclohexylcarbodiimide or the isourea ethers thereof, optionally in the presence of a reaction accelerator such as copper chloride and optionally in the presence of an inorganic base such as potassium carbonate or a tertiary organic base such as triethylamine, 1,8-diazabicyclo[5,4,0]-undec-7-ene or pyridine, or by transesterification, e.g. with a corresponding carbonic acid diester, at temperatures of between −20° C. and 100° C., but preferably at temperatures of between −10° C. and the boiling temperature of the solvent used.

The optional subsequent hydrogenolysis is carried out in the presence of a hydrogenation catalyst such as palladium/charcoal in a suitable solvent such as methanol, ethanol, ethanol/water, glacial acetic acid, ethyl acetate, dioxan or dimethylformamide.

If W in a compound of formula XV contains a carboxy group, this can be converted during the reaction into the corresponding alkoxycarbonyl group.

l) In order to prepare compounds of formula I wherein $R_4$ represents a hydrogen atom, methyl, ethyl or allyl group and W represents a methyl, formyl, carboxy, carboxymethyl, 2-carboxy-ethyl, alkoxycarbonyl, alkoxycarbonylmethyl or 2-alkoxycarbonylethyl group, in which the alkoxy part can contain from 1 to 4 carbon atoms.

Reacting a compound of formula (XVII)

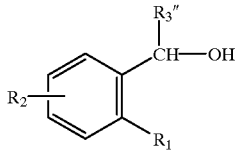

wherein $R_1$ and $R_2$ are as hereinbefore defined and $R_3''$ represents a hydrogen atom, an alkyl group with 1 to 7 carbon atoms, a phenyl group optionally substituted by a halogen atom or by a methyl or methoxy group, an alkyl group with 1 or 2 carbon atoms substituted by an alkoxy, alkanoyloxy, tetrahydrofuranyl, tetrahydropyranyl, cycloalkyl or phenyl group, wherein the alkoxy part can contain 1 to 3 carbon atoms, the alkanoyloxy part can contain 2 or 3 carbon atoms and the cycloalkyl part can contain 3 to 7 carbon atoms, an alkenyl group with 3 to 6 carbon atoms, an alkynyl group with 3 to 5 carbon atoms, a carboxy group or an alkoxycarbonyl group with a total of 2 to 5 carbon atoms, with a compound of formula (XVIII)

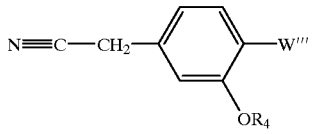

wherein $R_4$ is as hereinbefore defined and

W''' represents a methyl, formyl, carboxy, carboxymethyl, 2-carboxy-ethyl, alkoxycarbonyl, alkoxycarbonylmethyl or 2-alkoxy-carbonyl-ethyl group, in which each alkoxy part can contain from 1 to 4 carbon atoms.

The reaction is carried out in the presence of a strong acid which can simultaneously serve as solvent, preferably in concentrated sulfuric acid, at temperatures of between 0° and 150° C., preferably at temperatures of between 20° and 100° C.

If in a compound of formula XVIII $R_4$ represents an allyl group, this is split off during the reaction or after the reaction by the addition of water.

m) In order to prepare compounds of formula I wherein $R_4$ represents a hydrogen atom, a methyl or ethyl group, $R_3$ represents an alkyl group with 1 to 7 carbon atoms, a phenyl group optionally substituted by a methyl or methoxy group, an alkyl group with 1 or 2 carbon atoms substituted by an alkoxy, tetrahydrofuranyl, tetrahydropyranyl, cycloalkyl or phenyl group in which the alkoxy part can contain 1 to 3 carbon atoms and the cycloalkyl part can contain 5 to 7 carbon atoms, and W represents a methyl, hydroxymethyl, carboxy, cyanomethyl, 2-cyano-ethyl, carboxymethyl, 2-carboxy-ethyl, alkoxycarbonyl, alkoxycarbonylmethyl or 2-alkoxycarbonyl-ethyl group in which the alkoxy part can contain from 1 to 4 carbon atoms.

Reduction of a compound of formula (XIX)

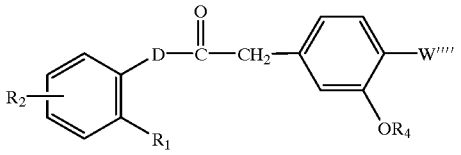

wherein $R_1$, $R_2$ and $R_4$ are as hereinbefore defined and

D represents a group of formula

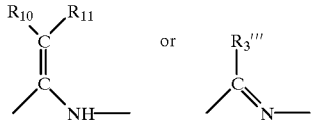

in which $R_3'''$ represents a phenyl group optionally substituted by a halogen atom or by a methyl or methoxy group.

$R_{10}$ and $R_{11}$ together with the carbon atom between them represent an alkylidene group with 1 to 7 carbon atoms, an alkylidene group with 1 or 2 carbon atoms substituted by an alkoxy, tetrahydrofuranyl, tetrahydropyranyl, cycloalkyl or phenyl group, in which the alkoxy part can contain 1 to 3 carbon atoms and the cycloalkyl part can contain 5 to 7 carbon atoms, and W'''' represents a methyl, hydroxymethyl, formyl, carboxy, cyanomethyl, 2-cyano-ethyl, 2-cyano-ethyl, carboxymethyl, 2-carboxy-ethyl, 2-carboxyethenyl, alkoxycarbonyl, alkoxycarbonylmethyl, 2-alkoxycarbonyl-ethyl or 2-alkoxycarbonylethenyl group, in which the alkoxy part can contain from 1 to 4 carbon atoms and can be substituted by a phenyl group.

The reduction is preferably carried out with hydrogen in the presence of a hydrogenation catalyst such as palladium/charcoal or Raney-nickel in a suitable solvent such as methanol, ethanol, isopropanol, ethyl acetate, dioxan, tetrahydrofuran, dimethylformamide, benzene or benzene/ethanol at temperatures of between 0° and 100° C., preferably at temperatures of between 20° and 50° C., and under a hydrogen pressure of from 1 to 5 bar. When a suitable chiral hydrogenation catalyst is used, such as a metal ligand complex e.g. [(2S), (4S)-1-tert.butoxycarbonyl-4-diphenylphosphino-2-diphenylphosphinomethyl-pyrrolidine-rhodium-cyclooctadiene(1,5)]-perchlorate, the addition of hydrogen occurs enantioselectively. Moreover, in the catalytic hydrogenation, other groups can also be reduced, e.g. a benzyloxy group can be reduced to the hydroxy group or a formyl group can be reduced to the hydroxy methyl group, or they can be replaced by hydrogen atoms, e.g. a halogen atom can be replaced by a hydrogen atom.

If a compound of the formula I is obtained wherein $R_2$ is halogen and/or $R_3$ is halophenyl and/or W is hydroxymethyl which has been converted into halomethyl, it may, if desired, be converted by d-halogenation into a corresponding compound of the formula I wherein $R_2$ is hydrogen and/or $R_3$ is phenyl and/or W is methyl.

If a compound of the formula I is obtained wherein W is carboxyl, this compound may, if desired, be converted by esterification into a corresponding compound of the formula I wherein W is alkoxycarbonyl or phenylalkoxycarbonyl.

If a compound of the formula I is obtained wherein W is carboxyl, alkoxycarbonyl or phenylalkoxycarbonyl, this compound may be converted by reduction into a corresponding compound of the formula I wherein W is formyl or hydroxymethyl.

If a compound of the formula I is obtained wherein W is hydroxymethyl, this compound may be converted by oxidation into a corresponding compound of the formula I wherein W is formyl or carboxyl.

If a compound of the formula I is obtained wherein W is carboxyl, this compound may be converted, via a sulfonic acid hydrazide and subsequent disproportionation, into a corresponding compound of the formula I wherein W is formyl.

The subsequent dehalogenation is advantageously carried out by catalytic hydrogenation, for example with palladium-on-charcoal, in a suitable solvent such as methanol, ethanol, tetrahydrofuran, dioxane, dimethylformamide or ethyl acetate, optionally in the presence of a base such as triethylamine, and at temperatures between 20° and 100° C., preferably at 20° to 50° C.

The subsequent esterification is advantageously carried out in a suitable solvent, for instance in a corresponding alcohol, pyridine, toluene, methylene chloride, tetrahydrofuran or dioxane, in the presence of an acid-activating and/or dehydrating agent such as thionyl chloride, ethyl chloroformate, carbonyldiimidazole or N,N'-dicyclohexylcarbodiimide or the isourea ethers thereof, optionally in the presence of a reaction accelerator such as copper chloride, or by trans-esterification, for instance with a corresponding carbonic acid diester, at temperatures between 0° and 100° C., but preferably at temperatures between 20° and the boiling point of the solvent which is used.

The subsequent reduction is preferably carried out with a metal hydride, for example with a complex metal hydride such as lithium aluminum hydride, lithium borohydride or lithium borohydride/trimethylborate, in a suitable solvent such as diethyl ether, tetrahydrofuran, dioxane or 1,2-dimethoxyethane at temperatures between 0° and 100° C., but preferably at temperatures between 20° C. and 60° C.

The subsequent oxidation of an alcohol is preferably carried out with an oxidizing agent, for instance with pyridinium chlorochromate or manganese dioxide, in a suitable solvent such an chloroform or methylene chloride at temperatures between as chloroform or methylene chloride at temperatures between −10° and 50° C., but preferably at temperatures between 0° and 20° C.

The subsequent disproportionation of a sulfonic acid hydrazide, obtained by reacting a corresponding hydrazine with a suitable reactive carboxylic acid derivative, is carried out in the presence of a base such as sodium carbonate in a solvent such as ethylene glycol at temperatures between 100° C. and 200° C., but preferably at 160°–170° C.

If according to the invention a racemic compound of formula I is obtained wherein $R_3$ has the meanings given hereinbefore with the exception of the hydrogen atom, this compound can be resolved into the enantiomers thereof via the diastereomeric adducts, complexes, salts or derivatives thereof.

The subsequent racemate splitting is preferably carried out by column or HPL chromatography by forming diastereomeric adducts or complexes in a chiral phase.

The compounds of formula I obtained according to the invention can also be converted into the salts thereof and, for pharmaceutical use, into the nontoxic, pharmaceutically acceptable salts thereof with inorganic or organic acids or bases. Suitable acids include, for example, hydrochloric, hydrobromic, sulfuric, phosphoric, lactic, citric, tartaric, succinic, maleic, fumaric, aspartic or glutamic acid and suitable bases include sodium hydroxide, potassium hydroxide, calcium hydroxide, cyclohexylamine, ethanolamine, diethanolamine, triethanolamine, ethylenediamine, lysine or arginine.

The compounds of formulae II to XIX used as starting materials are known from the literature in some cases or can be obtained by methods known per se.

Thus, for example, a compound of formula II is obtained by reducing a corresponding nitrile with lithium aluminium hydride or with catalytically activated hydrogen, by reacting a corresponding nitrile with a corresponding grignard or lithium compound and subsequent lithium-aluminium hydride reduction or subsequent hydrolysis to form the ketimine which is subsequently reduced with catalytically activated hydrogen, with a complex metal hydride or with nascent hydrogen, by hydrolysis or by hydrazinolysis of a corresponding phthalimido compound, by reacting a corresponding ketone with ammonium formate and subsequent hydrolysis or with an ammonium salt in the presence of sodium cyanoborohydride, by reduction of a corresponding oxime with lithium aluminium hydride, with catalytically activated or nascent hydrogen, by reduction of a corresponding N-benzyl or N-1-phenylethyl Schiff's base e.g. with a complex metal hydride in either or tetrahydrofuran at temperatures of between −78° C. and the boiling temperature of the solvent used with subsequent splitting off of the benzyl or 1-phenylethyl group by catalytic hydrogenation, by lithiation of a corresponding benzylideneimino-benzyl compound, e.g. by means of lithium-diisopropylamide at temperatures of between −78° and 20° C., subsequent reaction with a corresponding halogen compound, e.g. with a corresponding bromoalkyl, bromoalkenyl or bromoalkinyl compound, and subsequent hydrolysis, by Ritter reaction of a corresponding alcohol with potassium cyanide in sulfuric acid, by Hofmann, Curtius, Lossen or Schmidt degradation of a corresponding compound or by converting a corresponding benzaldehyde into a corresponding glycine derivative, e.g. using sodium cyanide/ammonium carbonate in ethanol/water into a corresponding hydantoin derivative, hydrolysis thereof, and, if necessary, subsequent esterification and, if necessary, subsequent reduction, e.g. with a complex metal hydride in ether or tetrahydrofuran.

An amine of formula II thus obtained having a chiral centre can be resolved into its enantiomers by racemate splitting, e.g. by fractional crystallization of the diastereomeric salts with optically active acids and subsequent decomposition of the salts or by column of HPL chromatography, optionally in the form of the acyl derivative thereof, or by forming diasteromeric compounds, separating them and subsequently splitting them.

Moreover, an optically active amine of formula II can also be prepared by enantioselective reduction of a corresponding ketimine using complex boron or aluminium hydrides in which some of the hydride hydrogen atoms have been replaced by optically active alkoxide groups, or by means of hydrogen in the presence of a suitable chiral hydrogenation catalyst or analogously starting from a corresponding N-benzyl or N-(1-phenethyl)-ketimine or from a corresponding N-acyl-ketimine or enimide and optionally subsequently splitting off the benzyl, 1-phenethyl or acyl group.

Furthermore, an optically active amine of formula II can also be prepared by diastereoselective reduction of a corresponding ketimine or hydrazone substituted at the nitrogen atom with a chiral group, using a complex or non-complex boron or aluminium hydride in which some of the hydride hydrogens can optionally be replaced by corresponding alkoxide, phenoxide or alkyl groups or using hydrogen in the presence of a suitable hydrogenation catalyst optionally with subsequent splitting off of the chiral auxiliary group by catalytic hydrogenolysis or hydrolysis.

Moreover, an optically active amine of formula II can also be prepared by diastereo-selective addition of a corresponding organometallic compound, preferably a grignard or lithium compound, to a corresponding aldimine substituted with a chiral group at the nitrogen atom, by subsequent hydrolysis and optionally subsequent splitting off of the chiral auxiliary group by catalytic hydrogenolysis or hydrolysis.

The compounds of formulae IV, V, VI, VIII, IX, X, XII, XIII and XV used as starting materials are obtained by reacting a corresponding amine with a suitable carboxylic acid or a reactive derivative thereof and, if necessary, subsequently splitting off any protecting group used.

A compound of formula XVII used as starting material is obtained by reducing a corresponding carbonyl compound by reacting a corresponding carbonyl compound with a corresponding grignard or lithium reagent or by hydrolysis or alcoholysis of a corresponding cyanohydrin and, if necessary, subsequent esterification.

A compound of formula XIX used as starting material is obtained by acylating a corresponding ketimine or the organometallic complex thereof with a corresponding carboxylic acid or reactive derivatives thereof, optionally with tautomerization.

The following examples illustrate the present invention and will enable others skilled in the art to understand it more completely. It should be understood, however, that the invention is not limited solely to the particular examples given below.

EXAMPLE 1

Ethyl 2-ethoxy-4-[N-{1-(2-piperidino-phenyl)-1-butyl}aminocarbonylmethyl]-benzoate 2 g (7.9 mmols) of 3-ethoxy-4-ethoxycarbonylphenylacetic acid, 2.46 g (9.38 mmols) of triphenylphosphine, 1.7 ml (12.3 mmols) of triethylamine and 0.76 ml (7.9 mmols) of carbon tetrachloride were added to a solution of 1.84 g (7.9 mmols) of 1-(2-piperidinophenyl)-1-butylamine in 19 ml of acetonitrile, and the mixture was stirred for two days at room temperature. It was then evaporated in vacuo, and the residue was taken up in a mixture of ethyl acetate and water. The organic phase was dried, filtered and evaporated in vacuo. The evaporation residue was purified by column chromatography on silica gel (toluene/acetone=5/1).

Yield: 3 g (81% of theory).

M.p. 113°–115° C. (petroleum ether).

Calculated: C—72.07%; H—8.21%; N—6.00%. Found: C—72.18%; H—8.27%; N—6.16%.

The following compounds were prepared by a procedure analogous to that described in Example 1:

(a) Methyl 2-methoxy-4-[N-{1-(2-piperidino-phenyl)-1-ethyl}aminocarbonylmethyl]-benzoate Prepared from 1-(2-piperidino-phenyl)-1-ethylamine and 3-methoxy-4-methoxycarbonyl-phenylacetic acid.

Yield: 78% of theory.

M.p. 82°–85° C.

Calculated: C—70.22%; H—7.37%; N—6.82%. Found: C—70.54%; H—7.49%; N—6.75%.

(b) Ethyl 2-ethoxy-4-[N-{α-phenyl-2-piperidino-benzyl) aminocarbonylmethyl}-benzoate Prepared from α-phenyl-2-piperidino-benzylamine and 3-ethoxy-4-ethoxycarbonyl-phenylacetic acid.

Yield: 77% of theory.

M.p. 149°–151° C.

Calculated: C—7.437%; H—7.25%; N—5.60%. Found: C—74.69%; H—6.44%; N—5.59%.

(c) Methyl 2-methoxy-4-[N-(α-phenyl-2-piperidino-benzyl)aminocarbonylmethyl]-benzoate Prepared from α-phenyl-2-piperidino-benzylamine and 3-methoxy-4-methoxycarbonyl-phenylacetic acid.

Yield: 65% of theory.

M.p. 189°–190° C.

Calculated: C—73.70%; H—6.83%; N—5.93%. Found: C—73.51%; H—6.75%; N—5.86%.

(d) Ethyl 2-ethoxy-4-[N-1-{2-piperidino-phenyl}-1-ethyl)aminocarbonylmethyl]-benzoate Prepared from 1-(2-piperidino-phenyl)-1-ethylamine and 3-ethoxy-4-ethoxycarbonyl-phenylacetic acid.

Yield: 69% of theory.

M.p. 92°–93° C.

Calculated: C—71.21%; H—7.81%; N—6.39%. Found: C—71.29%; H—8.03%; N—6.58%.

(e) Ethyl 2-ethoxy-4-[N-{1-(5-chloro-2-piperidino-phenyl)-1-propyl}-aminocarbonylmethyl]-benzoate Prepared from 1-(5-chloro-2-piperidino-phenyl)-1-propylamine and 3-ethoxy-4-ethoxycarbonyl-phenylacetic acid.

Yield: 80% of theory.

M.p. 110°–112° C.

Calculated: C—66.58%; H—7.24%; N—5.75%; Cl—7.28. Found: C—66.61%; H—7.34%; N—5.86%; Cl—7.35%.

(F) Ethyl 2-ethoxy-4-[N-{1-(2-piperidino-phenyl)-1-pentyl}-aminocarbonylmethyl]-benzoate Prepared from 1-(2-piperidino-phenyl)-1-pentylamine and 3-ethoxy-4-ethoxycarbonyl-phenylacetic acid.

Yield: 63% of theory.

M.p. 113°–115° C.

Calculated: C—72.47%; H—8.39%; N—5.83%. Found: C—72.66%; H—8.26%; N—5.99%.

(g) Ethyl 2-ethoxy-4-[N-{1-(2-pyrrolidino-phenyl)-1-butyl}-aminocarbonylmethyl]-benzoate Prepared from 1-(2-pyrrolidino-phenyl)-1-butylamine and 3-ethoxy-4-ethoxycarbonyl-phenylacetic acid.

Yield: 50% of theory.

M.p. 85°–87° C.

Calculated: C—71.65%; H—8.02%; N—6.19%. Found: C—71.90%; H—8.37%; N—6.34%.

(h) Ethyl 2-ethoxy-4-[N-{1-(2-methyl-piperidino)-phenyl)-1-butyl}-aminocarbonylmethyl]-benzoate Prepared from 1-[2-(4-methyl-piperidino)-phenyl]-1-butylamine and 3-ethoxy-4-ethoxycarbonyl-phenylacetic acid.

Yield: 44% of theory.

M.p. 127°–128° C.

Calculated: C—72.47%; H—8.39%; N—5.83%. Found: C—72.20%; H—8.23%; N—5.69%.

(i) Ethyl 2-ethoxy-4-[N-{1-(2-hexamethyleneimino-phenyl)-1-butyl}-aminocarbonylmethyl]-benzoate Prepared from 1-(2-hexamethyleneimino-phenyl)-1-butylamine and 3-ethoxy-4-ethoxycarbonyl-phenylacetic acid.

Yield: 44% of theory.

M.p. 97°–100° C.

Calculated: C—72.47%; H—8.39%; N—5.83%. Found: C—72.41%; H—8.50%; N—5.66%.

(k) Ethyl 2-ethoxy-4-[N-{1-(4-methyl-2-piperidino-phenyl)-1-butyl}-aminocarbonylmethyl]-benzoate Prepared from 1-(4-methyl-2-piperidino-phenyl)-1-butylamine and 3-ethoxy-4-ethoxycarbonyl-phenylacetic acid.

Yield: 68% of theory.

M.p. 113°–114° C.

Calculated: C—72.47%; H—8.39%; N—5.83%. Found: C—72.36%; H—8.31%; N—5.91%.

(l) Ethyl 2-ethoxy-4-[N-{1-(6-methyl-2-piperidino-phenyl)-1-butyl}-aminocarbonylmethyl]-benzoate Prepared from 1-(6-methyl-2-piperidino-phenyl)-1-butylamine and 3-ethoxy-4-ethoxycarbonyl-phenylacetic acid.

Yield: 62% of theory.

M.p. <20° C.

Calculated: C—72.47%; H—8.39%; N—5.83%. Found: C—72.30%; H—8.50%; N—5.72%.

(m) Ethyl 2-ethoxy-4-[N-{1-(6-chloro-2-piperidino-phenyl)-1-butyl}-aminocarbonylmethyl]-benzoate Prepared from 1-(6-chloro-2-piperidino-phenyl)-1-butylamine and 3-ethoxy-4-ethoxycarbonyl-phenylacetic acid.

Yield: 85% of theory.

M.p. <20° C.

Calculated: C—67.12%; H—7.44%; N—5.50%; Cl—7.08%. Found: C—67.60%; H—7.77%; N—5.92%; Cl—7.24%.

(n) Ethyl 2-ethoxy-4-[N-{1-(4-methoxy-2-piperidino-phenyl)-1-butyl}-aminocarbonylmethyl]-benzoate Prepared from 1-(4-methoxy-2-piperidino-phenyl)-1-butylamine and 3-ethoxy-4-ethoxycarbonyl-phenylacetic acid.

Yield: 65% of theory.

M.p. 109°–110° C.

Calculated: Mol peak m/e=496 Found: Mol. peak m/e=496.

(o) Ethyl 2-ethoxy-4-[N-{1-(5-methoxy-2-piperidino-phenyl)-1-butyl}-aminocarbonylmethyl]-benzoate Prepared from 1-(5-methoxy-2-piperidino-phenyl)-1-butylamine and 3-ethoxy-4-ethoxycarbonyl-phenylacetic acid.

Yield: 31% of theory.

M.p. 117°–120° C.

Calculated: Mol. peak m/e=496 Found: Mol. peak m/e=496.

(p) Ethyl 2-hydroxy-4-[N-{1-(2-piperidino-phenyl)-1-butyl}-aminocarbonylmethyl]-benzoate Prepared from 1-(2-piperidino-phenyl)-1-butylamine and 4-ethoxycarbonyl-3-hydroxy-phenylacetic acid.

Yield: 46% of theory.

M.p. 133°–134° C.

Calculated: C—71.21%; H—7.81%; N—6.39%. Found: C—71.08%; H—7.91%; N—6.45%.

(q) Methyl 2-methoxy-4-[N-{1-(2-piperidino-phenyl)-1-butyl}-aminocarbonylmethyl]-benzoate Prepared from 1-(2-piperidino-phenyl)-1-butylamine and 3-methoxy-4-methoxycarbonyl-phenylacetic acid.

Yield: 67% of theory.

M.p. 128°–131° C.

Calculated: C—71.21%; H—7.81%; N—6.39%. Found: C—71.46%; H—7.80%; N—6.06%.

(r) n-Propyl 2-n-propoxy-4-[N-{1-(2-piperidino-phenyl)-1-butyl}-aminocarbonylmethyl]-benzoate Prepared from 1-(2-piperidino-phenyl)-1-butylamine and 3-n-propoxy-4-n-propoxycarbonyl-phenylacetic acid.

Yield: 56% of theory.

M.p. 88°–89° C.

Calculated: C—72.84%; H—8.56%; N—5.55%. Found: C—72.80%; H—8.78%; N—5.78%.

(s) Ethyl 2-ethoxy-4-[N-(5-chloro-2-piperidino-benzyl) aminocarbonylmethyl]-benzoate Prepared from 5-chloro-2-piperidino-benzylamine and 3-ethoxy-4-ethoxycarbonyl-phenylacetic acid.

Yield: 65% of theory.

M.p. 106°–108° C.

Calculated: C—65.41%; H—6.81%; N—6.10%; Cl-7.73%. Found: C—65.81%; H—6.89%; N—6.11%; Cl—7.62%.

(t) Ethyl (−)-2-ethoxy-4-[N-(α-phenyl-2-piperidino-benzyl)aminocarbonylmethyl]-benzoate Prepared from (−)-α-phenyl-2-piperidino-benzylamine and 3-ethoxy-4-ethoxycarbonyl-phenylacetic acid.

Yield: 87% of theory.

M.p. 110°–111° C.

Calculated: mol peak m/e=500 Found: mol peak m/e=500.

Specific rotation $[\alpha]_D^{20}$=−6.3° (c=1, methanol).

(u) Ethyl 2-ethoxy-4-[N-(6-methyl-α-phenyl-2-piperidinobenzyl)-aminocarbonylmethyl]-benzoate Prepared from 6-methyl-α-phenyl-2-piperidino-benzylamine and 3-ethoxy-4-ethoxycarbonyl-phenylacetic acid.

Yield: 39% of theory.

M.p. <20° C.

Calculated: C—74.68%; H—7.44%; N—5.44%. Found: C—74.81%; H—7.56%; N—5.32%.

(v) Ethyl 2-ethoxy-4-[N-{α-(4-methyl-phenyl)-2-piperidinobenzyl}-aminocarbonylmethyl]-benzoate Prepared from α-(4-methyl-phenyl)-2-piperidino-benzylamine and 3-ethoxy-4-ethoxycarbonyl-phenylacetic acid.

Yield: 34% of theory.

M.p. 150°–152° C.

Calculated: C—74.68%; H—7.44%; N—5.44%. Found: C—74.71%; H—7.51%; N—5.29%.

(w) Ethyl 2-ethoxy-4-[N-(α-phenyl-2-pyrrolidino-benzyl)aminocarbonylmethyl]-benzoate Prepared from α-phenyl-2-pyrrolidino-benzylamine and 3-ethoxy-4-ethoxycarbonyl-phenylacetic acid.

Yield: 45% of theory.

M.p. 85°–87° C.

Calculated: C—74.05%; H—7.04%; N—5.76%. Found: C—73.95%; H—7.07%; N—5.70%.

(x) Methyl 2-methoxy-4-[N-(2-hexamethyleneimino-α-phenylbenzyl)aminocarbonylmethyl]-benzoate Prepared from 2-hexamethyleneimino-α-phenyl-benzylamine and 3-methoxy-4-methoxycarbonyl-phenylacetic acid.

Yield: 45% of theory.

M.p. 181°–182° C.

Calculated: C—74.05%; H—7.04%; N—5.74%. Found: C—74.09%; H—6.62%; N—5.74%.

(y) Ethyl 2-ethoxy-4-[N-(2-hexamethyleneimino-α-phenyl-benzyl)aminocarbonylmethyl]-benzoate Prepared from 2-hexamethyleneiminoα-phenyl-benzylamine and 3-ethoxy-4-ethoxycarbonyl-phenylacetic acid.

Yield: 41% of theory.

M.p. 140°–141° C.

Calculated: C—74.68%; H—7.44%; N—5.44%. Found: C—74.46%; H—7.62%; N—5.45%.

(z) 2-Ethoxy-4-[N-{1-(2-piperidino-phenyl)-1-butyl}aminocarbonylmethyl]-toluene

Prepared from 1-(2-piperidino-phenyl)-1-butylamine and 3-ethoxy-4-methyl-phenylacetic acid.

Yield: 55% of theory.

M.p. 107°–108° C.

Calculated: C—76.43%; H—8.88%; N—6.86%. Found: C—76.38%; H—8.99%; N—6.97%.

(aa) Ethyl 2-ethoxy-4-[N-{1-(2-piperidino-phenyl)-1-heptyl}aminocarbonylmethyl]-benzoate Prepared from 1-(2-piperidino-phenyl)-1-heptylamine and 3-ethoxy-4-ethoxycarbonyl-phenylacetic acid.

Yield: 79% of theory.

M.P. 101°–104° C.

Calculated: C—73.19%; H—8.72%; N—5.51%. Found: C—73.00%; H—8.90%; N—5.28%.

EXAMPLE 2

Ethyl (+)-2-ethoxy-4-[N-{1-(2-piperidino-phenyl)-1-butyl}aminocarbonylmethyl]-benzoate 0.90 g (3.57 mmol) of 3-ethoxy-4-ethoxycarbonylphenylacetic acid and 0.61 g (3.73 mmol) of N,N'-carbonyldiimidazole are refluxed for 5 hours in 9 ml of absolute tetrahydrofuran. Then a solution of 0.85 g (3.67 mmol) of (+)-1-(2-piperidino-phenyl)-1-butylamine (ee=94.2) in 9 ml of absolute tetrahydrofuran is added and the mixture is refluxed for 3 hours. It is concentrated in vacuo and the evaporation residue is distributed between chloroform and water. The organic phase is dried, filtered and evaporated in vacuo. The evaporated extract is purified by column chromatography on silica gel (toluene/acetone=10.1).

Yield: 0.85 g (51.2% of theory).

M.p. 118°–119° C. (petroleum ether/toluene=50/2).

Calculated: C—72.07%; H—8.21%; N—6.00%. Found: C—72.43%; H—8.34%; N—6.00%.

Specific rotation: $[\alpha]_D^{20}$=+7.1° (c=1.06 in methanol).

The following compounds were obtained analogously to Example 2:

(a) Methyl 3-methoxy-4-[N-{1-(2-piperidino-phenyl)-1-butyl}-aminocarbonylmethyl]-benzoate Prepared from 1-(2-piperidino-phenyl)-1-butylamine and 2-methoxy-4-methoxycarbonyl-phenylacetic acid.

Yield: 89% of theory.

M.p. 102°–105° C.

Calculated: C—71.20%; H—7.81%; N—6.39%. Found: C—71.20%; H—8.02%; N—6.27%.

(b) Ethyl 3-ethoxy-4-[N-{1-(2-piperidino-phenyl)-1-butyl}-aminocarbonylmethyl]-benzoate Prepared from 1-(2-piperidino-phenyl)-1-butylamine and 2-ethoxy-4-ethoxycarbonyl-phenylacetic acid.

Yield: 73% of theory.

M.p. 136°–138° C.

Calculated: C—72.07%; H—8.21%; N—6.00%. Found: C—72.50%; H—8.33%; N—5.95%.

(c) Ethyl 3-ethoxy-4-[N-{1-(4-methyl-2-piperidino-phenyl)-1-butyl}-aminocarbonylmethyl]-benzoate Prepared from 1-(4-methyl-2-piperidino-phenyl)-1-butylamine and 2-ethoxy-4-ethoxycarbonyl-phenylacetic acid.

Yield: 61% of theory.

M.p. 108°–110° C.

Calculated: C—72.46%; H—8.39%; N—5.83%. Found: C—72.50%; H—8.46%; N—5.92%.

(d) Ethyl 3-ethoxy-4-[N-{1-(6-methyl-2-piperidino-phenyl)-1-butyl}-aminocarbonylmethyl]-benzoate Prepared from 1-(6-methyl-2-piperidino-phenyl)-1-butylamine and 2-ethoxy-4-ethoxycarbonyl-phenylacetic acid.

Yield: 90% of theory.

M.p. <20° C.

Calculated: C—72.46%; H—8.39%; N—5.83%. Found: C—72.86%; H—8.20%; N—5.50%.

(e) Methyl 3-methoxy-4-[N-(α-phenyl-2-piperidino-benzyl)-aminocarbonylmethyl]-benzoate Prepared from α-phenyl-2-piperidino-benzylamine and 2-methoxy-4-methoxycarbonyl-phenylacetic acid.

Yield: 86% of theory.

M.p. 144°–148° C.

Calculated: C—73.70%; H—6.83%; N—5.93%. Found: C—73.70%; H—6.85%; N—5.84%.

(f) Ethyl 3-ethoxy-4-[N-(α-phenyl-2-piperidino-benzyl)-aminocarbonylmethyl]-benzoate Prepared from α-phenyl-2-piperidino-benzylamine and 2-ethoxy-4-ethoxycarbonyl-phenylacetic acid.

Yield: 77% of theory.

M.p. 112°–115° C.

Calculated: C—74.37%; H—7.25%; N—5.60%. Found: C—74.69%; H—7.29%; N—5.75%.

EXAMPLE 3

Ethyl 2-ethoxy-4-[N-(α-phenyl-2-piperidino-benzyl)-aminocarbonylmethyl]-benzoate A solution of 4.7 g (20 mmol) of ethyl 2-ethoxy-4-eyanomethyl-benzoate and 5.3 g (20 mmol) of α-phenyl-2-piperidino-benzyl alcohol in 30 ml of O-dichlorobenzene was added dropwise at 23°–25° C. to a mixture of 30 ml of concentrated sulfuric acid and 30 ml of o-dichlorobenzene. The mixture was stirred for 2 hours at room temperature. Then the o-dichlorobenzene phase was separated, and the residue was added to ice. After the aqueous mixture had been made alkaline with a soda solution, it was extracted with chloroform. The extracts were dried over magnesium sulfate and concentrated by evaporation. The residue was triturated with petroleum ether (30°–60°), filtered off and purified on silica gel (toluene/ethylacetate=5:1) by column chromatography.

Yield: 5.6 g (56% of theory).

M.p. 150°–151° C.

Calculated: C—74.37%; H—7.25%; N—5.60%. Found: C—74.59%; H—7.41%; N—5.45%.

The following compounds were obtained by a procedure analogous to that described in Example 3:

(a) Methyl 2-methoxy-4-[N-(α-phenyl-2-piperidino-benzyl)-aminocarbonylmethyl]-benzoate Prepared from α-phenyl-2-piperidino-benzyl alcohol and methyl 4-cyanomethyl-2-methoxy-benzoate.

Yield: 34% of theory.

M.P. 189°–191° C.

Calculated: C—73.70%; H—6.83%; N—5.93%. Found: C—73.63%; H—7.05%; N—5.95%.

(b) 2-Ethoxy-4-[N-(α-phenyl-2-piperidino-benzyl)-aminocarbonylmethyl]-benzoic acid Prepared from α-phenyl-2-piperidino-benzyl alcohol and 2-ethoxy-4-cyanomethyl-benzoic acid.

Extraction at pH 5.

Yield: 47% of theory.

M.p. 154°–155° C.

Calculated: C—74.70%; H—6.83%; N—5.93%. Found: C—73.61%; H—6.72%; N—5.65%.

(c) 2-Methoxy-4-[N-(α-phenyl-2-piperidino-benzyl)-aminocarbonylmethyl]-benzoic acid.

Prepared from α-phenyl-2-piperidino-benzyl alcohol and 4-cyanomethyl-2-methoxy-benzoic acid.

Extraction at ph 5.

Yield: 30% of theory.

M.p. 202°–204° C.

Calculated: C—73.34%; H—6.59%; N—6.11%. Found: C—73.17%; H—6.41%; N—6.05%.

(d) Ethyl 2-ethoxy-4-[N-{1-(2-piperidino-phenyl)-1-butyl}-aminocarbonylmethyl]-benzoate Prepared from 1-(2-piperidino-phenyl)-1-butanol and ethyl-2-ethoxy-4-cyanomethyl benzoate.

Yield: 5% of theory.

M.p. 112°–114° C.

Calculated: C—72.07%; H—8.21%; N—6.00%. Found: C—72.29%; H—8.46%; N—6.31%.

(e) Methyl 2-methoxy-4-[N-{1-(2-piperidino-phenyl)-1-ethyl}-aminocarbonylmethyl]-benzoate Prepared from 1-(2-piperidino-phenyl)-1-ethanol and methyl 4-cyanomethyl-2-methoxy-benzoate.

Yield: 18% of theory.

M.p. 83°–85° C.

Calculated: C—70.22%; H—7.37%; N—6.82%. Found: C—70.60%; H—7.29%; N—6.97%.

(f) 2-Methoxy-4-[N-{1-(2-piperidino-phenyl)-1-ethyl}-aminocarbonylmethyl]-benzoic acid Prepared from 1-(2-piperidino-phenyl)-1-ethanol and 4-cyanomethyl-2-methoxy-benzoic acid.

Extraction at pH 5.5.

Yield: 21% of theory.

M.p. 118°–120° C.

Calculated: m/e=396 Found: m/e=386.

(g) Ethyl 2-ethoxy-4-[N-(4-methyl-α-phenyl-2-piperidinobenzyl)aminocarbonylmethyl]-benzoate Prepared from 4-methyl-α-phenyl-2-piperidino-benzyl alcohol and ethyl 2-ethoxy-4-cyanomethyl-benzoate.

Yield: 45% of theory.

M.p. 124°–125° C.

Calculated: C—74.68%; H—7.44%; N—5.44%. Found: C—74.81%; H—7.56%; N—5.32%.

(h) Methyl 2-methoxy-4-[N-{α-(4chloro-phenyl)-2-piperidinobenzyl)-aminocarbonylmethyl]-benzoate Prepared from α-(4-chlorophenyl)-2-piperidino-benzyl alcohol and methyl 2-methoxy-4-cyanomethyl-benzoate.

Yield: 47% of theory.

M.p. 176°–178° C.

Calculated: C—68.70%; H—6.17%; N—5.53%; Cl—6.99%. Found: C—69.05%; H—5.93%; N—5.76%; Cl—7.10%.

(i) Ethyl 2-hydroxy-4-[N-(α-phenyl-2-piperidino-benzyl)-aminocarbonylmethyl]-benzoate Prepared from α-phenyl-2-piperidino-benzyl alcohol and ethyl 4-cyanomethyl-2-hydroxy-benzoate.

Yield: 78% of theory.

M.p. 172°–174° C.

Calculated: C—73.70%; H—6.83%; N—5.93%. Found: C—73.80%; H—6.81%; N—5.83%.

(k) n-Propyl 2-n-propoxy-4-[N-(α-phenyl-2-piperidino-benzyl)-aminocarbonylmethyl]-benzoate Prepared from α-phenyl-2-piperidino-benzyl alcohol and n-propyl 4-cyanomethyl-2-n-propoxy benzoate.

Yield: 52% of theory.

M.p. 119°–120° C.

Calculated: C—74.97%; H—7.63%; N—5.30%. Found: C—74.91%; H—7.72%; N—5.25%.

EXAMPLE 4

2-Ethoxy-4-[N-{1-(2-piperidino-phenyl)-1-butyl}-aminocarbonylmethyl]-benzoic acid A mixture of 2 g (4.3 mmols) of ethyl 2-ethoxy-4-[N-{1-(2-piperidino-phenyl)-1-butyl}-aminocarbonylmethyl]-benzoate and 5.3 ml of 1N sodium hydroxide solution in 20 ml of ethanol was stirred for 3 hours at 60° C., then neutralized with 5.3 ml of 1N hydrochloric acid, and the ethanol was evaporated in vacuo. The residue was taken up in a mixture of ethyl acetate and water, and the organic phase was dried, filtered and evaporated in vacuo. The evaporation residue was crystallized from petroleum ether with the addition of ethanol.

Yield: 1.3 g (69% of theory).

M.p. 88°–90° C.

Calculated: C—71.21%; H—7.81%; N—6.39%. Found: C—71.62%; H—7.73%; N—6.54%.

The following compounds were obtained by a procedure analogous to that described in Example 4:

(a) 2-Methyl-4-[N-{1-(2-piperidino-phenyl)-1-ethyl}-aminocarbonylmethyl]-benzoic acid×0.67 $H_2O$ Prepared from methyl 2-methoxy-4-[N-{1-(2-piperidino-phenyl)-1-ethyl}-aminocarbonylmethyl]-benzoate.

Yield: 60% of theory.

M.p. 116°–120° C.

Calculated: C—67.62%; H—7.07%; N—6.85%. Found: C—67.60%; H—6.87%; N—6.55%.

(b) 2-Ethoxy-4-[N-(α-phenyl-2-piperidino-benzyl)-aminocarbonylmethyl]-benzoic acid Prepared from ethyl 2-ethoxy-4-[N-(α-phenyl-2-piperidinobenzyl)-aminocarbonylmethyl]-benzoate.

Yield: 89% of theory.

M.p. 155°–156° C.

Calculated: C—73.70%; H—6.83%; N—5.93%. Found: C—73.60%; H—6.96%; N—6.12%.

(c) 2-Methoxy-4-[N-(α-phenyl-2-piperidino-benzyl)-aminocarbonylmethyl)-benzoic acid Prepared from methyl 2-methoxy-4-[N-(α-phenyl-2-piperidino-benzyl)-aminocarbonylmethyl]-benzoate.

Yield: 68% of theory.

M.p. 202°–204° C.

Calculated: C—73.34%; H—6.59%; N—6.11%. Found: C—73.60%; H—6.77%; N—6.20%.

(d) 2-Ethoxy-4-[N-{1-(5-chloro-2-piperidino-phenyl)-1-propyl}-aminocarbonylmethyl]-benzoic acid Prepared from ethyl 2-ethoxy-4-[N-{1-(5-chloro-2-piperidino-phenyl)-1-propyl}-aminocarbonylmethyl]-benzoate.

Yield: 74% of theory.

M.p. 115°–118° C.

Calculated: C—65.42%; H—6.81%; N—6.10%; Cl—7.72%. Found: C—65.54%; H—6.94%; N—5.81%; Cl—7.89%.

(e) 2-Ethoxy-4-[N-{1-(2-piperidino-phenyl)-1-propyl}-aminocarbonylmethyl]-benzoic acid Prepared from ethyl 2-ethoxy-4-[N-{1-(2-piperidino-phenyl)-1-propyl)-aminocarbonylmethyl]-benzoate.

Yield: 73% of theory.

M.p. 81°–83° C.

Calculated: C—70.73%; H—7.60%; N—6.60%. Found: C—70.90%; H—7.47%; N—6.77%.

(f) 2-Ethoxy-4-[N-{1-(2-piperidino-phenyl)-1-pentyl}-aminocarbonylmethyl]-benzoic acid Prepared from ethyl 2-ethoxy-4-[N-{1-(2-piperidino-phenyl)-1-pentyl}-aminocarbonylmethyl]-benzoate.

Yield: 92% of theory.

M.p. 82°–85° C.

Calculated: C—71.65%; H—8.02%; N—6.19%. Found: C—71.45%; H—8.01%; N—6.13%.

(g) 2-Ethoxy-4-[N-{1-(2-pyrrolidino-phenyl)-1-butyl}-aminocarbonylmethyl]-benzoic acid Prepared from ethyl 2-ethoxy-4-[N-{1-(2-pyrrolidinophenyl)-1-butyl}-aminocarbonylmethyl]-benzoate.

Yield: 77% of theory.

M.p. 120°–123° C.

Calculated: C—70.73%; H—7.60%; N—6.60%; Found: C—70.71%; H—7.44%; N—6.33%.

(h) 2-Ethoxy-4-[N-{1-(2-(4-methyl-piperidino)-phenyl)-1-butyl}-aminocarbonylmethyl]-benzoic acid Prepared from ethyl 2-ethoxy-4-[N-{1-(2-(4-methyl-piperidino)-phenyl)-1-butyl}-aminocarbonylmethyl]-benzoate.

Yield: 71% of theory.

M.p. 83°–85° C.

Calculated: C—71.65%; H—8.02%; N—6.19%. Found: C—71.60%; H—7.94%; N—6.09%.

(i) 2-Ethoxy-4-[N-{1-(2-hexamethyleneimino-phenyl)-1-butyl}-aminocarbonylmethyl]-benzoic acid Prepared from ethyl 2-ethoxy-4-[N-{1-(2-hexamethyleneimino-phenyl)-1-butyl}-aminocarbonylmethyl]-benzoate.

Yield: 81% of theory.

M.p. 101°–105° C.

Calculated: C—71.65%; H—8.02%; N—6.19%. Found: C—71.31%; H—7.79%; N—6.18%.

(k) 2-Ethoxy-4-[N-{1-(6-chloro-2-piperidino-phenyl)-1-butyl}-aminocarbonylmethyl]-benzoic acid Prepared from ethyl 2-ethoxy-4-[N-{1-(6-chloro-2-piperidino-phenyl)-1-butyl}-aminocarbonylmethyl]-benzoate.

Yield: 82% of theory.

M.p. 133°–136° C.

Calculated: C—66.02%; H—7.03%; N—5.92%; Cl—7.50%. Found: C—66.48%; H—7.47%; N—5.98%.

(l) 2-Ethoxy-4-[N-{1-(4-methoxy-2-piperidino-phenyl)-1-butyl}-aminocarbonylmethyl]-benzoic acid Prepared from ethyl 2-ethoxy-4-[N-{1-(4-methoxy-2-piperidino-phenyl)-1-butyl}-aminocarbonylmethyl]-benzoate.

Yield: 81% of theory.

M.p. 98°–100° C.

Calculated: C—69.21%; H—7.74%; N—5.98%. Found: C—69.12%; H—7.62%; N—5.78%.

(m) 2-Ethoxy-4-[N-{1-(5-methoxy-2-piperidino-phenyl)-1-butyl}-aminocarbonylmethyl]-benzoic acid Prepared from ethyl 2-ethoxy-4-[N-{1-(5-methoxy-2-piperidino-phenyl)-1-butyl}-aminocarbonylmethyl]-benzoate.

Yield: 74% of theory.

M.p. 145°–148° C.

Calculated: C—69.21%; H—7.74%; N—5.98%. Found: C—69.00%; H—7.65%; N—5.89%.

(n) 2-Methoxy-4-[N-{1-(2-piperidino-phenyl-1-butyl}-aminocarbonylmethyl]-benzoic acid Prepared from methyl 2-methoxy-4-[N-{1-(2-piperidino-phenyl)-1-butyl}-aminocarbonylmethyl]-benzoate.

Yield: 86% of theory.

M.p. 140°–143° C.

Calculated: C—70.73%; H—7.60%; N—6.60%. Found: C—70.49%; H—7.58%; N—6.31%.

(o) 2-n-Propoxy-4-[N-{1-(2-piperidino-phenyl)-1-butyl}-aminocarbonyl]-benzoic acid Prepared from n-propyl 2-n-propoxy-4-[N-{1-(2-piperidinophenyl)-1-butyl}-aminocarbonylmethyl]-benzoate.

Yield: 89% of theory.

M.p. 128°–132° C.

Calculated: C—71.65%; H—8.02%; N—6.19%. Found: C—71.40%; H—7.90%; N—6.47%.

(p) 2-Ethoxy-4-[N-(5-chloro-2-piperidino-benzyl)-aminocarbonylmethyl]-benzoic acid×0.5 $H_2O$ Prepared from ethyl 2-ethoxy-4-[N-5-chloro-2-piperidinobenzyl)-aminocarbonyl-methyl]-benzoate.

Yield: 93% of theory.

M.p. 153°–155° C.

Calculated: C—62.79%; H—6.41%; N—6.36%; Cl—8.06%. Found: C—63.21%; H—6.34%; N—5.89%; Cl—8.46%.

(g) 2-Ethoxy-4-[N-(2-piperidino-benzyl)-aminocarbonylmethyl]-benzoic acid

Prepared from ethyl 2-ethoxy-4-[N-(2-piperidino-benzyl)-aminocarbonylmethyl]-benzoate.

Yield: 77% of theory.

M.p. 108°–109° C.

Calculated: C—69.68%; H—7.12%; N—7.07%. Found: C—70.00%; H—7.99%; N—7.31%.

(r) 2-Hydroxy-4-[N-{1-(2-piperidino-phenyl)-1-butyl}-aminocarbonylmethyl]-benzoic acid Prepared from ethyl 2-hydroxy-4-[N-{1-(2-piperidinophenyl)-1-butyl}-aminocarbonylmethyl]-benzoate.

Yield: 61% of theory.

M.p. 136°–138° C.

Calculated: C—70.22%; H—7.37%; N—6.82%. Found: C—70.40%; H—7.64%; N—6.60%.

(s) 2-Isopropoxy-4-[N-{1-(2-piperidino-phenyl)-1-butyl}-aminocarbonylmethyl]-benzoic acid Prepared from ethyl 2-isopropoxy-4-[N-{1-(2-piperidinophenyl)-1-butyl}-aminocarbonylmethyl]-benzoate.

Yield: 67% of theory.

M.p. 115°–118° C.

Calculated: C—71.65%; H—8.02%; N—6.19%. Found: C—71.94%; H—7.96%; N—6.04%.

(t) 2-Allyloxy-4-[N-{1-(2-piperidino-phenyl)-1-butyl}-aminocarbonylmethyl]-benzoic acid Prepared from ethyl 2-allyloxy-4-[N-{1-(2-piperidinophenyl)-1-butyl}-aminocarbonylmethyl]-benzoate.

Yield: 92% of theory.

M.p. 110°–112° C.

Calculated: C—71.97%; H—7.61%; N—6.22%. Found: C—71.90%; H—7.62%; N—6.21%.

(u) 2-Benzyloxy-4-[N-{1-(2-piperidino-phenyl)-1-butyl}-aminocarbonylmethyl]-benzoic acid Prepared from ethyl 2-benzyloxy-4-[N-{1-(2-piperidinophenyl)-1-butyl}-aminocarbonylmethyl]-benzoate.

Yield: 95% of theory.

M.p. 161°–163° C.

Calculated: C—74.37%; N—7.25%; N—5.60%. Found: C—74.40%; N—7.44%; N—5.64%.

(v) (+)-2-Ethoxy-4-[N-{1-(2-piperidino-phenyl)-1-butyl}-aminocarbonylmethyl]-benzoic acid Prepared from ethyl (+)-2-ethoxy-4-[N-{1-(2-piperidinophenyl)-1-butyl}-aminocarbonylmethyl] benzoate.

Yield: 81% of theory.

M.p. 122°–123° C.

Calculated: C—71.21%; H—7.81%; N—6.39%. Found: C—71.19%; H—7.77%; N—6.29%.

Specific rotation $[\alpha]_D^{20}$=4.75° (c=1.03 in methanol).

(w) 3-Methoxy-4-[N-{1-(2-piperidino-phenyl)-1-butyl}-aminocarbonylmethyl]-benzoic acid Prepared from methyl 3-methoxy-4-[N-{1-(2-piperidinophenyl)-1-butyl}-aminocarbonylmethyl]-benzoate.

Yield: 64% of theory.

M.p. 188°–191° C.

Calculated: C—70.73%; H—7.60%; N—6.60%. Found: C—70.88%; H—7.56%; N—6.59%.

(x) 3-Ethoxy-4-[N-{1-(2-piperidino-phenyl)-1-butyl}-aminocarbonylmethyl]-benzoic acid Prepared from ethyl 3-ethoxy-4-[N-{1-(2-piperidino-phenyl)-1-butyl}-aminocarbonylmethyl]-benzoate.

Yield: 79% of theory.

M.p. 155°–165° C.

Calculated: C—71.21%; H—7.81%; N—6.39%. Found: C—71.32%; H—7.62%; N—6.24%.

(y) 3-Ethoxy-4-[N-{1-(4-methyl-2-piperidino-phenyl)-1-butyl}-aminocarbonylmethyl]-benzoic acid Prepared from ethyl 3-ethoxy-4-[N-{1-(4-methyl-2-piperidino-phenyl)-1-butyl}-aminocarbonylmethyl]-benzoate.

Yield: 71% of theory.

M.p. 186°–188° C.

Calculated: C—71.65%; H—8.02%; N—6.19%. Found: C—71.70%; H—7.86%; N—6.26%.

(z) 3-Ethoxy-4-[N-{1-(6-methyl-2-piperidino-phenyl)-1-butyl}-aminocarbonylmethyl]-benzoic acid Prepared from ethyl 3-ethoxy-4-[N-{1-(6-methyl-2-piperidino-phenyl)-1-butyl}-aminocarbonylmethyl]-benzoate.

Yield: 65% of theory.

M.p. 174°–176° C.

Calculated: C—71.65%; H—8.02%; N—6.19%. Found: C—72.00%; H—8.10%; N—5.91%.

(aa) 2-Ethoxy-4-[N-(4-methyl-α-phenyl-2-piperidino-benzyl)aminocarbonylmethyl]-benzoic acid Prepared from ethyl 2-ethoxy-4-[N-(4-methyl-α-phenyl-2-piperidino-benzyl)-aminocarbonylmethyl]-benzoate.

Yield: 41% of theory.

M.p. 127°–129° C.

Calculated: C—74.05%; H—7.04%; N—5.76%. Found: C—73.80%; H—7.09%; N—5.74%.

(ab) 2-Ethoxy-4-[N(6-methyl-α-phenyl-2-piperidino-benzyl)aminocarbonylmethyl]-benzoic acid Prepared from ethyl 2-ethoxy-4-[N-(6-methyl-α-phenyl-2-piperidino-benzyl)-aminocarbonylmethyl]-benzoate.

Yield: 40% of theory.

M.p.: 118°–121° C.

Calculated: C—74.05%; H—7.04%; N—5.76%. Found: C—73.71%; H—6.92%; N—5.76%.

(ac) 2-Ethoxy-4-[N-{α-(4-methyl-phenyl)-2-piperidino-benzyl}aminocarbonylmethyl]-benzoic acid Prepared from ethyl 2-ethoxy-4-[N-{α-(4-methyl-phenyl)-2-piperidino-benzyl}-aminocarbonylmethyl]-benzoate.

Yield: 94% of theory.

M.p. 148°–151° C.

Calculated: C—74.05%; H—7.04%; N—5.76%. Found: C—74.20%; H—7.15%; N—5.81%.

(ad) 2-Methoxy-4-[N-(α-(4-chloro-phenyl)-2-piperidino-benzyl}aminocarbonylmethyl]-benzoic acid Prepared from methyl 2-methoxy-4-[N-{α-(4-chloro-phenyl)-2-piperidino-benzyl}-aminocarbonylmethyl]-benzoate.

Yield: 77% of theory.

m.p. 177°–180° C.

Calculated: C—68.21%; H—5.03%; N—5.68%; Cl—7.19%. Found: C—68.10%; H—5.78%; N—5.53%; Cl—7.43%.

(ae) 2-Ethoxy-4-[N-(α-phenyl-2-pyrrolidino-benzyl)-aminocarbonylmethyl]-benzoic acid Prepared from ethyl 2-ethoxy-4-[N-(α-phenyl-2-pyrrolidinobenzyl)-aminocarbonylmethyl]-benzoate.

Yield: 67% of theory.

M.p. 141°–143° C.

Calculated: C—73.34%; H—6.59%; N—6.11%. Found: C—73.33%; H—6.74%; N—6.021%.

(af) 2-methoxy-4-[N-(2-hexamethyleneimino-α-phenyl-benzyl)-aminocarbonylmethyl]-benzoic acid Prepared from methyl 2-methoxy-4-[N-(2-hexamethyleneimino-α-phenyl-benzyl)-aminocarbonylmethyl]-benzoate.

Yield: 90% of theory.

M.p. 154°–156° C.

Calculated: C—73.70%; H—6.83%; N—5.93%. Found: C—73.70%; H—7.00%; N—5.95%.

(ag) 2-Ethoxy-4-[N-(2-hexamethyleneimino-α-phenyl-benzyl)-aminocarbonylmethyl]-benzoic acid Prepared from ethyl 2-ethoxy-4-[N-(2-hexamethyleneimino-α-phenyl-benzyl)-aminocarbonylmethyl]-benzoate.

Yield: 75% of theory.

M.p. 139°–141° C.

Calculated: C—74.05%; H—7.04%; N—5.76%. Found: C—73.90%; H—7.14%; N—5.78%.

(ah) 2-Hydroxy-4-[N-(α-phenyl-2-piperidino-benzyl)-aminocarbonylmethyl]-benzoic acid Prepared from ethyl 2-hydroxy-4-[N-(α-phenyl-2-piperidinobenzyl)-aminocarbonylmethyl]-benzoate by hydrolysis with 4 equivalents of 1N sodium hydroxide in ethanol/dioxane.

Yield: 35% of theory.

M.p. 222°–224° C.

Calculated: C—72.95%; H—6.35%; N—6.30%. Found: C—73.00%; H—6.64%; N—6.28%.

(ai) 2-n-Propoxy-4-[N-(α-phenyl-2-piperidino-benzyl) aminocarbonylmethyl]-benzoic acid Prepared from n-propyl 2-n-propoxy-4-[N-(α-phenyl-2-piperidino-benzyl)-aminocarbonylmethyl]-benzoate.

Yield: 41% of theory.

M.p. 168°–170° C.

Calculated: C—74.05%; H—7.04%; N—5.76%. Found: C—74.20%; H—7.19%; N—5.57%.

(ak) 2-Allyloxy-4-[N-(α-phenyl-2-piperidino-benzyl) aminocarbonylmethyl]-benzoic acid Prepared from ethyl 2-allyloxy-4-[N-(α-phenyl-2-piperidino-benzyl)-aminocarbonylmethyl]-benzoate.

Yield: 69% of theory.

M.p. 172°–172° C.

Calculated: C—74.35%; H—6.66%; N—5.78%. Found: C—74.11%; H—6.50%; N—5.74%.

(al) 2-Benzyloxy-4-[N-(α-phenyl-2-piperidino-benzyl) aminocarbonylmethyl]-benzoic acid Prepared from ethyl 2-benzyloxy-4-[N-(α-phenyl-2-piperidino-benzyl)-aminocarbonylmethyl]-benzoate.

Yield: 72% of theory.

M.p. 214°–215° C.

Calculated: C—76.38%; H—6.41%; N—5.24%. Found: C—76.18%; H—6.39%; N—5.36%.

(am) (–)-2-Ethoxy-4-[N-(α-phenyl-2-piperidino-benzyl) aminocarbonylmethyl]-benzoic acid Prepared from ethyl (–)-2-ethoxy-4-[N-(α-phenyl-2-piperidino-benzyl)-aminocarbonylmethyl]-benzoate.

Yield: 89% of theory.

M.p. 90°–95° C.

Calculated: C—73.70%; H—6.83%; N—5.93%. Found: C—73.59%; H—6.81%; N—5.83%.

Specific rotation: $[\alpha]_D^{20}=-2.2°$ (c=1 in methanol).

(an) 3-Methoxy-4-[N-(α-phenyl-2-piperidino-benzyl)-aminocarbonylmethyl]-benzoic acid Prepared from methyl 3-methoxy-4-[N-(α-phenyl-2-piperidino-benzyl)-aminocarbonylmethyl]-benzoate.

Yield: 72% of theory.

M.p. 220°–221° C.

Calculated: C—73.34%; H—6.59%; N—6.11%. Found: C—73.36%; H—6.46%; N—5.86%.

(ao) 3-Ethoxy-4-[N-(α-phenyl-2-piperidino-benzyl) aminocarbonylmethyl]-benzoic acid Prepared from ethyl 3-ethoxy-4-[N-(α-phenyl-2-piperidinobenzyl)-aminocarbonylmethyl]-benzoate.

Yield: 70% of theory.

M.p. 199°–201° C.

Calculated: C—73.70%; H—6.83%; N—5.93%. Found: C—73.50%; H—6.74%; N—5.94%.

(ap) 2-Ethoxy-4-[N-{1-(2-piperidino-phenyl)-1-heptyl}-aminocarbonylmethyl]-benzoic acid Prepared from ethyl 2-ethoxy-4[N-{1-(2-piperidino-phenyl)-1-heptyl}-aminocarbonylmethyl]-benzoate.

Yield: 88% of theory.

M.p. 71°–73° C.

Calculated: C—72.47%; H—8.39%; N—5.83%. Found: C—72.28%; H—8.56%; N—5.82%.

EXAMPLE 5

Sodium salt of 2-ethoxy-4-[N-{1-(2-piperidino-phenyl)-1-ethyl}aminocarbonylmethyl]-benzoic acid×1.5 $H_2O$ Prepared from ethyl 2-ethoxy-4-[N-{1-(2-piperidino-phenyl)-1-ethyl}-aminocarbonylmethyl]-benzoate analogous to Example 4. After purification by column chromatography the evaporation residue was dissolved in ethanol and mixed with 1 equivalent of 1N sodium hydroxide. By evaporation in vacuo and trituration with acetone, the crystalline sodium salt was obtained.

Yield: 76% of theory.

M.p. 242°–244° C.

Calculated: C—62.73%; H—7.01%; N—6.01%. Found: C—62.74%; H—7.17%; N—6.05%.

The following compounds were obtained by a procedure analogous to that described in Example 5;

(a) Sodium salt of 2-ethoxy-4-[N-{1-(4-methyl-2-piperidinophenyl)-1-butyl}-aminocarbonylmethyl]-benzoic acid×0.5 $H_2O$ Prepared from ethyl 2-ethoxy-4-[N-{1-(4-methyl2-piperidino-phenyl)-1-butyl}-aminocarbonylmethyl]-benzoate.

Yield: 72% of theory.

M.p. 255°–260° C.

Calculated: C—67.06%; H—7.50%; N—5.79%. Found: C—66.94%; H—7.28%; N—5.50%.

(b) Sodium salt of 2-ethoxy-4[N-{1-(6-methyl-2-piperidinophenyl)-1-butyl)-aminocarbonylmethyl]-benzoic acid×2.5 $H_2O$ Prepared from ethyl 2-ethoxy-4-[N-{1-(6-methyl-2-piperidino-phenyl)-1-butyl}-aminocarbonylmethyl]-benzoate.

Yield: 81% of theory.

M.p. 232°–240° C.

Calculated: C—62.39%; H—7.75%; N—5.39%. Found: C—62.22%; H—7.46%; N—5.61%.

(c) Sodium salt of 2-ethoxy-4-[N-{1-(2-piperidino-phenyl)-1-butyl}-aminocarbonylmethyl]-benzoic acid Prepared from ethyl 2-ethoxy-4-[N-{1-(2-piperidino-phenyl)-1-butyl}-aminocarbonylmethyl]-benzoate.

Yield: 87% of theory.

M.p. 250°–258° C.

Calculated: C—67.79%; H—7.22%; N—6.08%. Found: C—67.60%; H—7.37%; N—6.04%.

(d) Sodium salt of 2-ethoxy-4-(α-phenyl-2-piperidino-benzyl)aminocarbonylmethyl]-benzoic acid Prepared from ethyl 2-ethoxy-4-[N-(α-phenyl-2-piperidinobenzyl)-aminocarbonylmethyl]-benzoate.

Yield: 89% of theory.

M.p. 233°–235° C.

Calculated: C—70.42%; H—6.32%; N—5.67%. Found: C—70.20%; H—6.41%; N—5.49%.

EXAMPLE 6

Ethyl 2-hydroxy-4-[N-(α-phenyl-2-piperidino-benzyl)-aminocarbonylmethyl]-benzoate 1 ml (10.4 mmols) of boron tribromide was added dropwise at –20° C. under anhydrous conditions to a stirred solution of 2 g (4 mmols) of ethyl 2-ethoxy-4-[N-(α-phenyl-2-piperidinobenzyl)-aminocarbonylmethyl]-benzoate in 20 ml of 1,2-dichloroethane. The mixture was allowed to reach room temperature and was then stirred for 17 hours. It was then poured into ethanol, evaporated in vacuo, ice was added, and the resulting mixture was taken up in a mixture of chloroform and water. The organic phase was dried, filtered and evaporated in vacuo. The evaporation residue was purified by column chromatography on silica gel (toluene/ethyl acetate=5/1).

Yield: 0.37 g (21% of theory).

M.p. 172°–173° C.

Calculated: C—73.70%; H—6.83%; N—5.93%. Found: C—73.95%; H—7.05%; N—6.12%.

The following compounds were obtained by a procedure analogous to that described in Example 6:

(a) 2-Hydroxy-4-[N-(α-phenyl-2-piperidino-benzyl) aminocarbonylmethyl]-benzoic acid Prepared from 2-ethoxy-4[N-(α-phenyl-2-piperidinobenzyl)-aminocarbonylmethyl]-benzoic acid.

Yield: 40% of theory.

M.p. 221°–223° C.

Calculated: C—72.95%; H—6.35%; N—6.30%. Found: C—72.68%; H—6.45%; N—6.49%.

(b) Ethyl 2-hydroxy-4-[N-{1-(2-piperidino-phenyl)-1-butyl}aminocarbonylmethyl]-benzoate Prepared from ethyl 2-ethoxy-4-[N-{1-(2-piperidino-phenyl)-1-butyl}-aminocarbonylmethyl]-benzoate.

Yield: 19% of theory.

M.P. 132°–134° C.

Calculated: C—71.21; H—7.81; N—6.39; Found: C—71.43; H—7.91; N—6.55;

(c) 2-Hydroxy-4-[N-(1-(2-piperidino-phenyl)-1-butyl) aminocarbonylmethyl]-benzoic acid Prepared from 2-ethoxy-4-[N-(1-(2-piperidino-phenyl)-1-butyl)-aminocarbonylmethyl]-benzoic acid Yield: 42% of theory.

M.P. 136°–137° C.

Calculated: C—70.22%; H—7.37%; N—6.82%. Found: C—70.19%; H—7.39%; N—6.99%.

EXAMPLE 7

Tert.butyl 2-ethoxy-4[N-{1-(2-piperidino-phenyl)-1-butyl}aminocarbonylmethyl]-benzoate A mixture of 1.9 g (9.6 mmols) of N,N'-dicyclohexylcarbodiimide, 1.06 ml (11.2 mmols) of absolute tert.butanol and 0.020 g (0.20 mmol) of copper(I) chloride was stirred for 60 hours at room temperature. Then, 6.6 ml of methylene chloride were added, and the resulting solution was added dropwise to a solution of 0.44 g (1 mmol) of 2-ethyoxy-4-[N-{1-(2-piperidinophenyl)-1-butyl}-aminocarbonylmethyl]-benzoic acid in 15 ml of methylene chloride. After 60 hours' stirring at 20° C., the precipitate which had formed was filtered off, washed with methylene chloride, and the methylene chloride solution was evaporated in vacuo. The evaporation residue was purified by column chromatography on silica gel (chloroform/ethyl acetate=9/1).

Yield: 0.30 g (60% of theory).

M.p. 74°–77° C. (from petroleum ether).

Calculated: C—72.84%; H—8.56%; N—5.66%. Found: C—73.00%; H—8.56%; N—5.79%.

EXAMPLE 8

Ethyl 2-benzyloxy-4-[N-(α-phenyl-2-piperidino-benzyl)-aminocarbonylmethyl]-benzoate 0.10 g (2.3 mmols) of sodium hydride (55% in oil) was added to a solution of 1.1 g (2.3 mmols) of ethyl 2-hydroxy-4-[N-(α-phenyl-2-piperidino-benzyl)-aminocarbonylmethyl]-benzoate in 10 ml of anhydrous dimethylformamide and the resulting mixture was stirred for half an hour at room temperature. Then, a solution of 0.27 ml (2.3 mmols) of benzyl bromide in 5 ml of anhydrous dimethylformamide was added dropwise, and the resulting mixture was stirred for 5 hours at room temperature. It was then evaporated in vacuo, the residue was taken up in a mixture of dilute sodium hydroxide and chloroform, and the organic phase was dried, filtered and evaporated in vacuo. The evaporation residue was recrystallized from acetonitrile.

Yield: 0.9 g (69.5% of theory).

M.p. 156°–157° C.

Calculated: C—76.84% H—6.81%; N—4.98%. Found: C—76.94%; H—6.95%; N—4.87%.

The following compounds were obtained by a procedure analogous to that described in Example 8:

(a) Ethyl 2-allyloxy-4[N-(α-phenyl-2-piperidino-benzyl) aminocarbonylmethyl]-benzoate Prepared from ethyl 2-hydroxy-4-[N-(α-phenyl-2-piperidinobenzyl)-aminocarbonylmethyl]-benzoate, using allyl bromide.

Yield: 46% of theory.

M.p. 117°–119° C.

Calculated: C—74.97%; H—7.08%; N—5.47%. Found: C—74.90%; H—7.14%; N—5.38%.

(b) Ethyl 2-isopropoxy-4-[N-{1-(2-piperidino-phenyl)-1-butyl}aminocarbonylmethyl]-benzoate Prepared from ethyl 2-hydroxy-4-[-{1-(2-piperidinophenyl)-1-butyl}-aminocarbonylmethyl]-benzoate, using 1.5 equivalents of isopropyl bromide at 150° C.

Yield: 56% of theory.

M.p. 98°–99° C.

Calculated: C—72.47%; H—8.39%; N—5.83%. Found: C—72.60%; H—8.60%; N—5.75%.

(c) Ethyl 2-allyloxy-4-[N-{1-(2-piperidino-phenyl)-1-butyl}aminocarbonylmethyl]-benzoate Prepared from ethyl 2-hydroxy-4-[N-{1-(2-piperidinophenyl)-1-butyl}-aminocarbonylmethyl]-benzoate, using allyl bromide.

Yield: 72% of theory.

M.p. 105°–106° C.

Calculated: C—72.77%; H—8.00%; N—5.85%. Found: C—72.90%; H—7.90%; N—5.87%.

(d) Ethyl 2-benzyloxy-4-[N-{1-(2-piperidino-phenyl)-1-butyl}-aminocarbonylmethyl]-benzoate Prepared from ethyl 2-hydroxy-4[N-{1-(2-piperidinophenyl)-1-butyl}-aminocarbonylmethyl]-benzoate, using benzyl bromide.

Yield: 80% of theory.

M.p. 135°–136° C.

Calculated: C—74.97%; H—7.63%; N—5.30%. Found: C—75.20%; H—7.78%; H—5.59%.

EXAMPLE 9

N-Propyl 2-n-propoxy-4-[N-(α-phenyl-2-piperidino-benzyl)-aminocarbonylmethyl]-benzoate Prepared from 2-hydroxy-4-(N-(α-phenyl-2-piperidinobenzyl)-aminocarbonylmethyl]-benzoate acid analogous to Example 8, using 2 equivalents of sodium hydride and 2 equivalents of n-propyl bromide.

Yield: 45% of theory.

M.p. 118°–120° C.

Calculated: C—74.97%; H—7.63%; N—5.30%. Found: C—75.20% H—7.80%; N—5.41%.

The following compound was obtained by a procedure analogous to that described in Example 9;

(a) n-Propyl 2-n-propoxy-4-[N-{1-(2-piperidino-phenyl)-1-butyl}-aminocarbonylmethyl]-benzoate Prepared from n-propyl 2-hydroxy-4-[N-{1-(2-piperidino-phenyl)-1-butyl}-aminocarbonylmethyl]-benzoate.

Yield: 39% of theory.

M.p. 89°–90° C.

Calculated: C—72.84%; H—8.56%; N—5.66%. Found: C—72.95%; H—8.77%; N—5.59%.

EXAMPLE 10

Ethyl 2-ethoxy-4-[N-(2-piperidino-benzyl)-aminocarbonylmethyl]-benzoate 1.0 g (2.18 mmols) of ethyl 2-ethoxy4-[N-(5-chloro-2-piperidino-benzyl)-aminocarbonylmethyl]-benzoate was hydrogenated in 20 ml of ethanol with 0.5 g of 10% palladium-on-charcoal at 50° C. under 1 bar of hydrogen for 45 minutes. The reaction mixture was filtered through diatomaceous earths, the filtrate was evaporated in vacuo, and the residue was purified by column chromatography on silica gel (chloroform/methanol—10/1).

Yield: 0.71 g (77% of theory).

M.p. 83°–84° C. (from petroleum ether).

Calculated: C—70.73%; H—7.60%; N—6.60%. Found: C—70.89%; H—7.66%; N—6.76%.

The following compound was obtained by a procedure analogous to that described in Example 10:

(a) Ethyl 2-ethoxy-4-[N-{1-(2-piperidino-phenyl)-1-propyl}-aminocarbonylmethyl]-benzoate Prepared from ethyl 2-ethoxy-4-[N-{1-(5-chloro-2-piperidino-phenyl)-1-propyl}-aminocarbonylmethyl]-benzoate.

Yield: 74% of theory.

M.p. 115°–117° C.

Calculated: C—71.65%; H—8.02%; N—6.19%. Found: C—71.47%; H—8.11%; N—6.25%.

EXAMPLE 11

2-Ethoxy-4-[N-{1-(2-piperidino-phenyl)-3-methyl-1-butyl}-aminocarbonylmethyl]-benzoic acid (form A)

(a) 2-Ethoxy-4-[N-{1-(2-piperidino-phenyl)-3-methyl-1-buten-1-yl}-aminocarbonylmethyl]-benzoic acid.

Prepared from ethyl 2-ethoxy-4-[N-{1-(2-piperidino-phenyl)-3-methyl-1-buten-1-yl}-aminocarbonylmethyl]-benzoate.

Yield: 85% of theory.

M.p. 110°–113° C.

Calculated: C—71.97%; H—7.61%; N—6.22%. Found: C—71.92%; H—7.80%; N—5.98%.

(b) 0.21 g (0.39 mmol) of 2-ethoxy-4-[N-{1-(2-piperidino-phenyl)-3-methyl-1-buten-1-yl}-aminocarbonylmethyl]-benzoic acid were hydrogenated in 10 ml of absolute ethanol with 0.10 g of 10 palladium-on-charcoal at 50° C. and a pressure of 1 bar of hydrogen for 7 hours. The reaction mixture was then filtered through diatomaceous earth, the reaction filtrate was evaporated in vacuo, and the residue was purified by column chromatography on silica gel (chloroform/methanol=10/1).

Yield: 0.10 g (47% of theory).

M.p. 90°–92° C. (recrystallized from acetone/petroleum ether).

Calculated: C—71.65% H—8.02%; N—6.19%. Found: C—71.50%; H—8.12%; N—6.45%.

2-Ethoxy-4-[N-{1-(2-piperidino-phenyl)-3-methyl-1-butyl}-aminocarbonylmethyl]-benzoic acid, is also obtained in other solid forms when it is crystallized from other solvents or mixtures of solvents. Form (B), which has a melting point of 140° to 142° C., is obtained by crystallization from an ethanol/water mixture. The foamy form (C), which has a melting point range from 75° to 85° C., is obtained from the 1:1 methanol adduct (melting point: 85° to 90° C.), which occurs upon crystallization from methanol, by heating at 60° C. in vacuo (5 Torr) over phosphorous pentoxide, whereby the methanol is removed.

In the dissolved state those forms are identical, as is evident from the corresponding solution spectra, for instance the IR-spectra in methylene chloride shown in FIGS. 1, 2 and 3 of the attached drawings. However, in the solid state, the three forms differ in their melting characteristics and their solid spectra, for instance as shown by the corresponding IR-KBr-spectra in FIGS. 4, 5 and 6 of the attached drawings.

In order to measure infra-red absorption, forms (A), (B) and (C) were dissolved in methylene chloride (40 mg of substance per ml of methylene chloride), or intimately triturated with potassium bromide and then compressed hydraulically to form a tablet (approx. 1 mg of substance/300 mg of KBr).

In the case of the solutions, the IR-spectra were measured with an IR-spectrometer (Perkin Elmer Type 299) in a cell of sodium chloride (layer thickness 0.2 mm) by comparison with a pure methylene chloride solution and, in the case of the potassium bromide tablets, with an IR-spectrometer (Perkin Elmer Type 298) by comparison with air.

The three solid forms can be conveyed into one another by suitable recrystallization and drying. Thus, the low-melting-point form (A) is obtained by recrystallizing the high-melting-point form (B) from acetone/petroleum ether and the high-melting-point form (B) is obtained by recrystallizing the low-melting-point form (A) from ethanol/water. By recrystallizing the high-melting-point form (B) from methanol, a 1:1 adduct with methanol is obtained, and from this the foamy form (C) is obtained by removing the methanol.

Irrespective of the particular process which is used to synthesize 2-Ethoxy-4-[N-}1-(2-piperidino-phenyl)-3-methyl-1-butyl}-aminocarbonylmethyl]-benzoic acid, therefore, the heat-melting-point or low-melting-point or foamy form can be obtained, as desired, by a suitable choice of solvent or mixture of solvents during crystallization and by suitable drying. This is important in the practical use of the solid forms, whether or not they are accompanied by galenic excipients in pharmaceutical compositions, particularly for lowering blood sugar in the treatment of Type II diabetes; this is because different solid forms may have different shelf lives and/or different absorption characteristics in vivo and may thus give a different pattern of biological activity.

2-Ethoxy-4-[N-{1-(2-piperidino-phenyl)-3-methyl-1-butyl}-aminocarbonylmethyl]-benzoic acid may be obtained by the methods described hereinabove, but preferably by reacting 3-methyl-1-(2-piperidino-phenyl)-1-butylamine with a compound of the formula (XI)

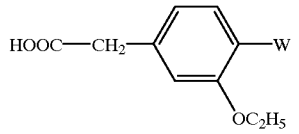

wherein W is carboxyl or carboxyl protected by a protective group or with a reactive derivative thereof, optionally prepared in the reaction mixture, followed, if necessary, by removal of the protective group, and the solid forms (B) and (C) are obtained by suitable subsequent crystallization, suitable final recrystallization and/or drying.

Examples of reactive derivatives of a compound of the formula XI include the esters such as the methyl, ethyl and benzyl esters thereof, the thioesters such as the methylthio and ethylthioesters, the halides such as the acid chloride, the anhydrides and imidazolides thereof.

The reaction is advantageously carried out in a solvent such as methylene chloride, chloroform, carbon tetrachloride, ether, tetrahydrofuran, dioxane, benzene, toluene, acetonitrile or dimethylformamide, optionally in the presence of an acid-activating agent or a dehydrating agent, for instance in the presence of ethyl chloroformate, thionyl chloride, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole, N,N'-thionyldiimidazole or triphenylphosphine/carbon tetrachloride, or in the presence of an amino group activating agent, such as phosphorus trichloride, and optionally in the presence of an inorganic base such as sodium carbonate or a teritary organic base such as triethylamine or pyridine, which may simultaneously serve as solvent, at temperatures between −25° and 250° C., but preferably at temperatures between −10° C. and the boiling point of the solvent which is used. The reaction may also be carried out without a solvent, and any water formed during the reaction may be removed by azeotropic distillation, for instance by heating with toluene, using a water trap, or by adding a drying agent such as magnesium sulfate or a molecular sieve.

The subsequent removal of the protective group is preferably carried out by hydrolysis, either in the presence of an acid such as hydrochloric, sulfuric, phosphoric or trichloroacetic acid, or in the presence of a base such as sodium hydroxide or potassium hydroxide, in a suitable solvent such as water, methanol, methanol/water, ethanol, ethanol/water, water/isopropanol or water/dioxane at temperatures between −10° and 120° C., for instance at temperatures between room temperature and the boiling point of the reaction mixture.

A tert.butyl protective group may also be removed thermally, optionally in an inert solvent such as methylene, chloride, chloroform, benzene, toluene, tetrahydrofuran or dioxane, and preferably in the presence of a catalytic quantity of an acid such as p-toluenesulfonic, sulfuric, phosphoric or polyphosphoric acid.

Moreover, a benzyl protective group may also be removed by hydrogenation in the presence of a hydrogenation catalyst such as palladium-on-charcoal in a suitable solvent such as methanol, ethanol, ethanol/water, glacial acetic acid, ethyl acetate, dioxane or dimethylformamide.

The subsequent crystallization is carried out in sutu from the reaction mixture containing ethanol/water or, as a final recrystallization, by dissolving the reaction product in a mixture of ethanol and water, optionally while heating, and cooling, optionally accompanied by trituration and/or seeding (form B), or by dissolving the reaction product in acetone and adding petroleum ether (form A), or by dissolving the reaction product, optionally while heating in methanol, subsequent cooling of the solution accompanied by trituration and/or seeding, and heating the isolated solid methanol adducts, preferably in vacuo, in the presence of a drying agent such as phosphorus pentoxide (form C).

Like the other compounds of the formula I, solid forms (A), (B) and (C) of 2-Ethoxy-4-[N-{1-(2-piperidino-phenyl)-3-methyl-1-butyl}-aminocarbonylmethyl]-benzoic acid may also be converted into their salts, particularly their non-toxic, pharmacologically acceptable table salts with inorganic or organic acids or bases. Suitable acids for this purpose are, for example, hydrochloric, hydrobromic, sulfuric, phosphoric, lactic citric, trataric, succinic, maleic or fumaric acid, and suitable bases are sodium hydroxide, potassium hydroxide, calcium hydroxide, cyclohexylamine, ethanolamine, diethanolamine, triethanolamine, ethylenediamine or lysine.

The melting points in Examples 12–16 were determined in an Electrothermal® melting point apparatus with visual observation of the sample of product in a capillary tube fused at one end.

EXAMPLE 12

Ethyl 2-ethoxy-4-[N-{1-(2-piperidino-phenyl)-3-methyl-1-butyl}-aminocarbonylmethyl]-benzoate 3 g (11.9 mmols) of 3-ethoxy-4-ethoxycarbonylphenylacetic acid, 3.7 g (14.3 mmols) of triphenylphosphine, 3.3 ml (23.8 mmols) of triethylamine and 1.15 ml (11.9 mmols) of carbon tetrachloride were added successively to a solution of 2.9 g (11.9 mmols) of 3-methyl-1-(2-piperidino-phenyl)-1-butylamine in 29 of acetonitrile. The mixture was then stirred for 15 hours at room temperature, the solvent was removed in vacuo, and the residue was taken up in a mixture of ethyl acetate and water. The organic phase was dried over sodium sulfate, filtered and concentrated by evaporation in vacuo. The evaporation residue was purified by column chromatography on silaca gel (toluene/acetone=10/1).

Yield: 4.9 g (85% of theory).

M.p. 143°–145° C. (petroleum ether).

Calculated: C-72.47%; H-8.39%; N-5.83%.

Found: C-72.37%; H-8.45%; N-6.07%.

EXAMPLE 13

High-melting-point form (B) of 2-ethoxy-4-[N-{1-(2-piperidinophenyl)-3-methyl-1-butyl}-aminocarbonylmethyl]-benzoic acid A mixture of 4.7 g (9.7 mmols) of ethyl 2-ethoxy-4-[N-{1-(2-piperidino-phenyl)-3-methyl-1-butyl}-aminocarbonylmethyl]-benzoate and 14.7 ml of 1N sodium hydroxide was stirred in 47 ml of ethanol for 2 hours at 60° C., then neutralized with 14.7 ml of 1N hydrochloric acid and cooled to 0° C. The mixture was filtered to remove the precipitated colorless crystals, and the crystals were washed with ice water and with a little ice cold ethanol and then dried at 100° C./1 Torr.

Yield: 3.9 g (88% of theory).

M.p. 140°–142° C.

Calculated: C-71.65%; H-8.02%; N-6.19%. Found: C-71.90%; H-8.08%; N-6.34%.

Upon further recrystallization from ethanol/water (2/1) the melting point remained constant.

EXAMPLE 14

Low-melting-point form (A) of 2-ethoxy-4-[N-{1-(2-piperidino-phenyl)-3-methyl-1-butyl}-aminocarbonylmethyl]-benzoic acid 1.0 g of the high-melting-point form (B) of 2-ethoxy-4-[N-{1-(2-piperidino-phenyl)-3-methyl-1-butyl}-aminocarbonyl-methyl]-benzoic acid was dissolved at room temperature in 5 ml of acetone, and 5 of petroleum ether (m.p. 60°–70° C.) were added. Upon trituration, crystallization gradually set in. The same quantity of petroleum ether was added again, and after crystallization had ended, the mixture was filtered. The crystals were washed with petroleum ether, and the almost colorless crystals were dried for 2 hours at 60° C./0.1 Torr.

Yield: 0.7 g.

M.p. 95°–98° C. (clear beginning at 135° C.).

Calculated: C-71.65%; H-8.02%; N-6.19%. Found: C-71.80%; H-8.04%; N-5.92%.

The IR-spectra for this form (see FIGS. 1 and 4) are identical to the IR-spectra for the form (A), melting point 90°–92° C., described in Example 11(b) above.

EXAMPLE 15

High-melting-point form (B) of 2-ethoxy-4[N-{1-2-piperidino-phenyl)-3-methyl-1-butyl}-aminocarbonylmethyl]-benzoic acid 1.0 g of the low-melting-point form (A) of 2-ethoxy-4-[N-{1-(2-piperidino-phenyl)-3-methyl-1-butyl}-amino-carbonylmethyl[-benzoic acid was dissolved in 10 ml of ethanol/water (2/1) while heating over a steam bath. The solution was then cooled to 0° C., whereupon crystallization began. The mixture was filtered, and the residue was washed with a little ice-cold ethanol and dried at 100° C./1 Torr.

Yield: 0.8 g.

M.p. 140°–142° C.

EXAMPLE 16

Foamy form (C) of 2-ethoxy-4-[N-{1-(2-piperidino-phenyl)-3-methyl-1-butyl}-aminocarbonylmethyl]-benzoic acid 1.5 g of the high-melting-point form (B) of 2-ethoxy-4-[N-{1-(2-piperidino-phenyl)-3-methyl-1-butyl}-aminocarbonyl-methyl]-benzoic acid was dissolved in 5 ml of methanol while heating. The solution was then cooled to 0° C. with trituration. The crystals precipitated thereby were separated by filtration, washed with a little cold methanol, and dried for 2 hours at 60° C./0.1 Torr.

Yield of adduct (with $1\times CH_3OH$): 1.2 g.

M.p. 85°–90° C.

Calculated: ($\times 1CH_3OH$): C-69.39%; H-8.32%; N-5.78%.

Found: C-69.20%; H-8.20%; N-5.92%.

The adduct was converted into the methanol-free foamy form (C) by heating for 24 hours at 60° C./5 Torr over phosphorus pentoxide.

Melting range: 75°–85° C.

Calculated: C-71.65%; H-8.02%; N-6.19%. Found: C-71.82%; H-8.06%; N-6.03%.

EXAMPLE 17

Ethyl 2-ethoxy-4-[N-{1-(2-piperidino-phenyl)-3-methyl-1-butyl}-aminocarbonylmethyl]-benzoate Prepared from ethyl 2-ethoxy-4-[N-{1-(2-piperidino-phenyl)-3-methyl-1-buten-1-yl}-aminocarbonylmethyl]-benzoate, melting point 125°–126° C., which in turn was prepared from (2-piperidino-phenyl)-isobutyl-ketimine and 3-ethoxy-4-ethoxy-carbonyl-phenol-acetic acid analogous to Example 1.

Yield: 51% of theory.

M.p. 139°–141° C.

Calculated: C-72.47%; H-8.39%; N-5.83%. Found: C-72.30%; H-8.20%; N-5.87%.

EXAMPLE 18

2-Ethoxy-4-[N-(α-phenyl-2-piperidino-benzyl)-aminocarbonyl-methyl]-benzyl alcohol A solution of 1.8 g (3.6 mmols) of ethyl 2-ethoxy-4-[N-(α-phenyl-2-piperidino-benzyl)-aminocarbonylmethyl]-benzoate in 20 ml of absolute tetrahydrofuran was added dropwise at −5° C. to a mixture of 0.28 g (7.4 mmols) of lithium aluminum hydride and 50 ml of absolute tetrahydrofuran, and the resulting mixture was stirred for 3 hours at 0° C. It was then diluted with absolute ether, and 4N sodium hydroxide was added. The mixture was filtered through diatomaceous earth, the filtrate was evaporated in vacuo, and the residue was purified by column chromatography on silica gel (toluene/ethyl acetate=2/1).

Yield: 0.51 g (31% of theory).

M.p. 133°–135° C.

Calculated: C-75.95%; H-7.47%; N-6.11%. Found: C-75.97%; H-7.55%; N-5.95%.

The following compound was obtained by a procedure analogous to that described in Example 18:

(a) 2-Ethoxy-4-[N-{1-(2-piperidino-phenyl)-1-butyl}-amino-carbonylmethyl]-benzyl alcohol Prepared from ethyl 2-ethoxy-4-[N-{1-(2-piperidino-phenyl)1-butyl}-aminocarbonylmethyl}-benzoate by reduction with lithium borohydride in boiling tetrahydrofuran in the presence of 10% of trimethyl borate.

Yield: 68% of theory.

M.p. 112°–115° C.

Calculated: C-73.55%; H-8.55%; N-6.60%. Found: C-73.60%; H-8.38%; N-6.69%.

EXAMPLE 19

2-Ethoxy-4-[N-(α-phenyl-2-piperidino-benzyl)-aminocarbonyl-methyl]-benzaldehyde

A solution of 0.4 g (0.87 mmol) of 2-ethoxy-4-[N-(α-phenyl-2-piperidino-benzyl)-aminocarbonylmethyl]-benzyl alcohol was added dropwise at room temperature to a stirred solution of 0.28 g (1.3 mmols) of pyridinium chlorochromate in 5 ml of chloroform. The reaction mixture was stirred overnight at room temperature, evaporated in vacuo, the residue was mixed with ether, the etheral mixture was filtered, the filtrate was evaporated in vacuo, and the residue was purified by column chromatography on silica gel (toluene/ethyl acetate=2/1).

Yield: 0.16 g (40% of theory).

M.p. 154°–156° C.

Calculated: C-76.29%; H-7.06%; N-6.14%. Found: C-76.30%; H-7.15%; N-6.10%.

The following compound was obtained by a procedure analogous to that described in Example 19:

(a) 2-Ethoxy-4-[N-{1-piperidino-phenyl)-1-butyl}-amino-carbonylmethyl]-benzaldehyde Prepared from ethyl 2-ethoxy-4-[N-{1-(2-piperidino-phenyl)-1-butyl}-aminocarbonylmethyl]-benzyl alcohol.

Yield: 47% of theory.

M.p. 109°–111° C.

Calculated: C-73.90%; H-8.11%; N-6.63%. Found: C-74.22%; H-8.14%; N-6.73%.

EXAMPLE 20

2-Ethoxy-4-[N-(α-phenyl-2-piperidino-benzyl)-aminocarbonyl-methyl]-benzaldehyde 0.67 g (5.6 mmols) of sodium carbonate was heated together with 6 ml of ethylene glycol on an oil bath at 170° C., and then, while rapidly stirring, 0.70 g (1.1 mmols) of $N^1$-[2-ethoxy-4-{N-(α-phenyl-2-piperidino-benzyl)-aminocarbonylmethyl}-benzoyl]-$N^2$-tosyl-hydrazine were added thereto within a minute; a violent evolution of gas was observed. Then, the mixture was heated for 2 minutes more at 170° C., and then poured immediately over ice. The aqueous mixture was extracted with ether, and the extract dried, filtered and evaporated in vacuo. The evaporation residue was purified by column chromatography on silica gel (toluene/ethyl acetate=2/1).

Yield: 0.25 g (50% of theory).

M.p. 153°–156° C.

Calculated: C-76.29%; H-7.06%; N-6.14%. Found: C-76.42%; H-7.33%; N-6.28%.

The following compound was obtained by a procedure analogous to that described in Example 20:

(a) 2-Ethoxy-4-[N-{1-(2-piperidino-phenyl)-1-butyl}-amino-carbonylmethyl]-benzaldehyde Prepared from $N^1$-[2-ethoxy-4-[N-{1-(2-piperidino-phenyl)-1-butyl}-aminocarbonylmethyl]-benzoyl]-$N^2$-tosyl-hydrazine.

Yield: 51% of theory.

M.p. 108°–111° C.

Calculated: C-73.90%; H-8.11%; N-6.63%. Found: C-73.79%; H-8.29%; N-6.75%.

EXAMPLE 21

Benzyl 2-ethoxy-4-[N-{1-(2-piperidino-phenyl)-1-butyl}-amino-carbonylmethyl]-benzoate 0.35 g (0.8 mmol) of 2-ethoxy-4-[N-{1-(2-piperidino-phenyl)-1-butyl}-aminocarbonylmethyl]-benzoic acid was refluxed together with 0.15 g (0.9 mmol) of N,N'-carbonyldiimidazole in 15 ml of absolute tetrahydrofuran for 2 hours. Then, 1.03 ml (10 mmols) of benzyl alcohol were added, and the mixture was refluxed for 3.5 hours. The reaction mixture was then evaporated in vacuo, and the residue was purified by column chromatography on silica gel (chloroform/acetone=9/1).

Yield: 0.10 g (23.6% of theory).

M.p. <20° C.

Calculated: Mol peak m/e=528. Found: Mol peak m/e=528.

EXAMPLE 22

Ethyl (±)-2-ethoxy-4-[N-{1-(2-piperidino-phenyl)-1-butyl}-aminocarbonylmethyl]-benzoate and

Ethyl (−)-2-ethoxy-4-[N-{1-(2-piperidino-phenyl)-1-butyl}-aminocarbonylmethyl]-benzoate 28 mg of ethyl (±)-2-ethoxy-4-N-{1-(2-piperidino-phenyl)-1-butyl}-aminocarbonylmethyl]-benzoate were added in 0.02 mg-portions to a chiral phase HPLC column made by the Baker Co., in which (R)-N-3,5-dinitrobenzoyl-phenylglycine was covalently bonded to aminopropyl-silica gel (5 μm particle size, spherical, pore size 60 Å; 4.6 mm internal diameter, 25 cm in length).

Flow agent: hexane/ethanol=100/5.

Flow rate: 0.75 ml/minute.

Temperature: 22° C.

The fractions eluted at 31.2 minutes and at 32.9 minutes (UV detection at 254 nm) were separately recovered, collected and evaporated in vacuo.

The following was obtained from the 31.2-minute eluate:

7.5 mg of ethyl (±)-2-ethoxy-4-[N-{1-(2-piperidino-phenyl)-1-butyl}-aminocarbonylmethyl]-benzoate.

M.p. 117°–119° C.

Specific rotation: $[\alpha]_D^{20}$=+7.0° (c=1.03 in methanol).

The following was obtained from the 32.9-minute eluate:

9.4 mg of ethyl (−)-2-ethoxy-4-N-{1-(2-piperidino-phenyl)-1-butyl}-aminocarbonylmethyl]-benzoate.

m.p. 115°–117° C.

Specific rotation: $[\alpha]_D^{20}$=−6.9° (c=1.02 in methanol).

Analogous to Example 22, (a) Ethyl (±)-2-ethoxy-4-[N-(α-phenyl-2-piperidino-benzyl)-aminocarbonylmethyl]-benzoate was separated into its (+) enantiomer and its (−) enantiomer.

EXAMPLE 23

Ethyl 2-acetoxy-4-[N-{1-(2-piperidino-phenyl)-1-butyl}-amino-carbonylmethyl]-benzoate A mixture of 0.20 g (0.46 mmol) of ethyl 2-hydroxy-4-[N-{1-(2-piperidino-phenyl)-1-butyl}-aminocarbonylmethyl]-benzoate, 0.34 ml (3.65 mmols) of acetic acid anhydride and 20 μl of concentrated sulfuric acid was stirred for 40 hours at 70° C. The mixture was then evaporated in vacuo, the residue was taken up in a mixture of water and ether, and neutralized with sodium carbonate. The etheral phase was separated, and the aqueous phase was extracted twice with ethyl acetate. The combined organic etacts were dried, filtered and evaporated in vacuo. The evaporation residue was purified by column chromatography on silica gel (toluene/acetone=19/1).

Yield: 50% of theory.

M.p. 133°–135° C. (from petroleum ether).

Calculated: C-69.98%; H-7.55%; N-5.83%. Found: C-69.75%; H-7.32%; N-5.74%.

The following compounds were obtained by a procedure analogous so that described in Example 23:

(a) 2-Acetoxy-4-[N-{1-(2-piperidino-phenyl)-1-butyl}-amino-carbonylmethyl]-benzoic acid Prepared from 2-hydroxy-4-[N-{1-(2-piperidino-phenyl)-butyl}-aminocarbonylmethyl]-benzoic acid.

Yield: 12% of theory.

M.p. 125°–127° C.

Calculated: Mol peak m/e=452. Found: Mol peak m/e=452.

(b) Ethyl 2-acetoxy-4-[N-(α-phenyl-2-piperidino-benzyl)-aminocarbonylmethyl]-benzoate Prepared from ethyl 2-hydroxy-4-[N-(α-phenyl-2-piperidino-benzyl)-aminocarbonylmethyl]-benzoate.

Yield: 23.5% of theory.

M.p. 163°–166° C.

Calculated: C-72.35%; H-6.66%; N-5.44%.

Found: C-72.41%; H-6.75%; N-5.31%.

(c) 2-Acetoxy-4-4-[N-(α-phenyl-2-piperidino-benzyl)-amino-carbonylmethyl]-benzoic acid Prepared from 2-hydroxy-4-[N-(α-phenyl-2-piperidino-benzyl)-aminocarbonylmethyl]-benzoic acid.

Yield: 17% of theory.

M.p. 126°–128° C.

Calculated: C-71.58%; H-6.21%; N-5.76%. Found: C-71.77%; H-6.57%; N-5.81%.

EXAMPLE 24

2-Ethoxy-4-[N-{1-(2-piperidino-phenyl)-1-butyl}-aminocarbonyl-methyl]-toluene A mixture of 0.54 g (1.2 mmols) of 2-ethoxy-4-[N-{1-(2-piperidino-phenyl)-1-butyl}-aminocarbonylmethyl]- benzyl chloride (melting point 114°–115° C., prepared from 2-ethoxy-4-[N-{1-(2-piperidino-phenyl)-1-butyl}-aminocarbonylmethyl-benzyl alcohol and thionyl chloride in chloroform) and 10 ml of absolute dioxane was hydrogenated for 3 hours at 20° C. and a pressure of 5 bar hydrogen. The reaction mixture was then evaporated in vacuo, and the residue was taken up in a mixture of ethyl acetate and aqueous sodium carbonate. The organic phase was dried, filtered and evaporated in vacuo. The evaporation residue was purified by column chromatography on silica gel (chloroform/acetone=19/1).

Yield: 0.23 g (47% of theory).

M.p. 107°–108° C.

Calculated: C-76.43%; H-8.88%; N-6.86%. Found: C-76.40%; H-8.88%; N-6.90%.

EXAMPLE 25

2-Ethoxy-4-[N-{1-(2-piperidino-phenyl)-1-butyl}-aminocarbonyl-methyl]-benzoic acid 100 mg (0.20 mmol) of tert.butyl 2-ethoxy-4-[N-{1-(2-piperidino-phenyl)-1-butyl}-aminocarbonyl]-benzoate were refluxed in 5 ml of benzene together with a few crystals of p-toluene-sulfonic acid hydrate for half a day. The desired product was obtained, as confirmed by thin-layer chromatography, by the $R_f$-value and mass spectrum.

M.p. 87°–89° C.

Calculated: m/e=438. Found: m/e=438.

EXAMPLE 26

2-Ethoxy-4-[N-{1-(2-piperidino-phenyl)-1-butyl}-aminocarbonyl-methyl]-benzoic acid 0.25 g (0.47 mmol) of benzyl 2-ethoxy-4-[N-{1-(2-piperidino-phenyl)-1-butyl}-aminocarbonylmethyl]-benzoate was hydrogenated in 10 ml of ethanol with 0.12 g of 10% palladium-on-charcoal at 50 and a pressure of 5 bar of hydrogen. After 5 hours the catalyst was filtered off through diatomaceous earth, and the filtrate was evaporated in vacuo. The evaporation residue was crystallized from petroleum ether/ethanol.

Yield: 01.4 g (70% of theory).

M.p. 87°–90° C.

Calculated: C-71.21%; H-7.81%; N-6.39%. Found: C-71.46%; H-7.95%; N-6.51%.

EXAMPLE 27

Ethyl 2-ethoxy-4-[N-{1-(2-piperidino-phenyl)-1-n-hexyl}-aminocarbonylmethyl]-benzoate Prepared from 1-(2-piperidino-phenyl)-1-n-hexylamine and 3-ethoxy-4-ethoxycarbonyl-phenylacetic acid analogous to Example 1.

Yield: 43% of theory.

M.p. 101°–105° C.

Calculated: C-72.84%; H-8.56%; N-5.66%. Found: C-72.72%; H-8.52%; N-5.63%.

EXAMPLE 28

2-Ethoxy-4-[N-{1-(2-piperidino-phenyl)-1-n-hexyl}-aminocarbonyl-methyl]-benzoic acid Prepared from ethyl 2-ethoxy-4-[N-{1-(2-piperidino-phenyl)-1-n-hexyl}-aminocarbonylmethyl]-benzoate analogous to Example 4.

Yield: 77% of theory.

M.p. 117°–120° C.

Calculated: C-72.07%; H-8.21%; N-6.00%. Found: C-72.00%; H-8.06%; N-5.90%.

EXAMPLE 29

[2-Ethoxy-4-[N-(1(2-piperidino-phenyl)-1-butyl)-amino-carbonylmethyl]-phenyl]-acetonitrile To a solution of 2-ethoxy-4-[N-(1-(2-piperidino-phenyl)-1-butyl)-aminocarbonylmethyl]-benzyl chloride (2 g; 4.5 mmol) [prepared from 2-ethoxy-4-[N-(1-(2-piperidino-phenyl)1-butyl)-aminocarbonylmethyl]-benzyl alcohol with thionyl chloride in chloroform], is added sodium cyanide (0.255 g, 5.2 mmol), dissolved in water (2.2 ml), and the phase transfer catalyst benzyl tributylammonium chloride (0.069 g, 0.22 mmol) and the mixture is stirred for 5 days at ambient temperature. Then, further phase transfer catalyst (0.069 g) is added, together with a few small grains of potassium iodide and sodium cyanide (0.2 g) in water (1 ml) and the mixture is stirred for a further 24 hours; then the same amounts of these three components are added again and the mixture is stirred for a further 12 hours. Methylene chloride (40 ml) is added and the mixture is extracted twice with water. The methylene chloride phase is dried over sodium sulphate/potassium carbonate, filtered and concentrated by evaporation in vacuo. The evaporation residue is purified by column chromatography on silica gel (toluene/ethyl acetate=5/1).

Yield: 1.53 g.

Melting point: 116°–118° C. (methylene chloride/ether)

Calculated: C 74.79; H 8.14; N 9.69. Found: C 74.86; H 8.19; N 9.42.

EXAMPLE 30

[2-Ethoxy-4-[N-(α-phenyl-2-piperidino-benzyl)-aminocarbonylmethyl]-phenyl]-acetonitrile A solution of 2-ethoxy-4-[N-(α-phenyl-2-piperidino-benzyl)-aminocarbonylmethyl]-benzyl chloride (2.6 g, 5.45 mmol) in dimethylsulphoxide (10 ml) is added dropwise at 50°–60° C. to sodium cyanide (0.32 g, 6.5 mmol) in dimethylsulphoxide (40 ml). The mixture is then stirred for 5 hours at 60° C., added to water and extracted with chloroform. The extract is concentrated by evaporation in vacuo. The residue is purified by column chromatography on silica gel (toluene/ethyl acetate=5/1).

Yield: 1.2 g.

Melting point: 145°–148° C.

Calculated: C 77.05; H 7.11; N 8.99. Found: C 76.92; H 7.05; N 8.78.

EXAMPLE 31

Ethyl [2-ethoxy-4-[N-(1-(2-piperidino-phenyl)-1-butyl)-aminocarbonylmethyl]-phenyl]-acetate Dry hydrogen chloride is introduced for 3 hours into a stirred and boiling solution of [2-ethoxy-4-[N-(1)2-piperidino-phenyl)-1-butyl)-aminocarbonylmethyl]-phenyl]-acetonitrile (1.3 g, 3 mmol) in absolute ethanol (30 ml). The mixture is then evaporated down in vacuo, water (25 ml) is added to the evaporation residue and this is stirred for 15 minutes at 50° C. The mixture is adjusted to a pH of 7 by the addition of solid sodium hydrogen carbonate and is extracted three times with ethyl acetate. The combined organic extracts are shaken once with water, then dried over sodium sulphate/potassium carbonate, filtered and concentrated by evaporation in vacuo. The evaporation residue is purified by column chromatography on silica gel (chloroform/ethyl acetate=9/1).

Yield: 1.0 g.

Melting point: 91°–93° C. (petroleum ether)

Calculated: C 72.47; H 8.39; N 5.83. Found: C 72.73; H 8.68; N 5.71.

EXAMPLE 32

Methyl [2-ethoxy-4-[N-(α-phenyl-2-piperidino-benzyl)-aminocarbonylmethyl]-phenyl]-acetate Dry hydrogen chloride is introduced for 4 hours into a stirred and refluxed solution of [2-ethoxy-4-(N-(α-phenyl-2-piperidino-benzyl)-aminocarbonylmethyl]-phenyl]-acetonitrile (1.2 g, 2.57 mmol) in methanol (20 ml). The mixture is then concentrated by evaporation, added to water and extracted with chloroform. The extract is dried and filtered and concentrated by evaporation in vacuo. The evaporation residue is purified by column chromatography on silica gel (toluene/ethyl acetate=4/1).

Yield: 340 mg.

Melting point: 136°–138° C. (acetonitrile/water).

Calculated: molecular peak m/e=500. Found: molecular peak m/e=500.

EXAMPLE 33

[2-Ethoxy-4-[N-(1-(2-piperidino-phenyl)-1-butyl-amino-carbonylmethyl]-phenyl]-acetic acid A 1N sodium hydroxide solution (2.8 ml) is added to ethyl [2-ethoxy-4-[N-(1-(2-piperidino-phenyl)-1-butyl-aminocarbonylmethyl]-phenyl]-acetate (0.67 g, 1.4 mmol) in ethanol (10 ml) and stirred for 4 hours at ambient temperature. Then the mixture is evaporated down in vacuo at 50° C. Water and a few drops of methanol are added to the evaporation residue which is then adjusted to pH 6 with 1N acetic acid. It is cooled in ice, whereupon a precipitate is formed. This is filtered off and recrystallized from ethanol.

Yield: 0.47 g.

Melting point: 158°–159° C. (ethanol)

Calculated: C 71.65; H 8.02; N 6.19. Found: C 71.35; H 8.30; N 6.21.

EXAMPLE 34

[2-Ethoxy-4-[N-(α-phenyl-2-piperidino-benzyl)-aminocarbonylmethyl]-phenyl]-acetic acid Prepared analogously to Example 33 by alkaline saponification of methyl [2-ethoxy-4-[N-(α-phenyl-2-piperidino-benzyl)-aminocarbonylmethyl]-phenyl]-acetate.

Melting point: 146°–148° C.

Calculated: C 74.05; H 7.04; N 5.76. Found: C 73.70; H 7.00; N 5.85.

EXAMPLE 35

Ethyl 2-ethoxy-4-[N-(1-(2-piperidino-phenyl)-1-butyl)-aminocarbonylmethyl]-cinnamate A solution of ethyl diethyl-phosphono-acetate (1.68 g, 7.5 mmol) in absolute dioxan (3 ml) is slowly added dropwise, with vigorous stirring, to a suspension of 55% sodium hydride (in oil) (0.327 g, 7.5 mmol) in absolute dioxan (4 ml). After the reaction has died down the mixture is heated to 80° C. for a further 45 minutes. It is then cooled to ambient temperature, a solution of 2-ethoxy-4-[N-(1-(2-piperidino-phenyl)-1-butyl)-aminocarbonyl-methyl]-benzaldehyde (2.11 g, 5 mmol) [prepared form the corresponding benzyl alcohol by oxidation with pyridinium chlorochromate in chloroform] in absolute dioxan (4 ml) is added dropwise thereto and the mixture is heated for 2 hours at 50° C. The reaction mixture is pured onto ice/water and extracted with chloroform. The organic extract is dried and filtered and evaporated down in vacuo. The evaporation residue is purified by column chromatography on silica gel (chloroform/ethyl acetate=19/1).

Yield: 1.64 g.

Melting point: 130°–131° C. (ether)

Calculated: C 73.14; H 8.18; N 5.69. Found: C 73.36; H 8.34; N 5.75.

EXAMPLE 36

2-Ethoxy-4-[N-(1-(2-piperidino-phenyl)-1-butyl)-amino-carbonylmethyl]-cinnamic acid nitrile Prepared analogously to Example 35 from 2-ethoxy-4-[N-(1-(2-piperidino-phenyl)-1-butyl)-amino-carbonylmethyl]-benzaldehyde with diethylphosphono-acetonitrile.

Melting point: 125°–128° C. (petroleum ether)

Calculated: C 75.47; H 7.92; N 9.43. Found: C 75.40; H 7.95; N 9.24.

EXAMPLE 37

2-ethoxy-4-[N-(α-phenyl-2-piperidino-benzyl)-aminocarbonylmethyl]-cinnamate

Under a nitrogen atmosphere, 50% sodium hydride (0.19 g, 8 mmol) is added to a stirred solution of ethyl diethylphosphono-acetate (1.8 g, 8 mmol) in absolute 1,2-dimethoxy-ethane (10 ml). Then a solution of 2-ethoxy-4-[N-(α-phenyl-2-piperidinobenzyl)-aminocarbonylmethyl]-benzaldehyde (2 g, 4.4 mmol) in absolute 1,2-dimethoxy-ethane (15 ml) is added and the mixture is stirred for 30 minutes at ambient temperature. It is concentrated by evaporation in vacuo and the evaporation residue is distributed between water and chloroform. The chloroform extract is dried and filtered and concentrated by evaporation in vacuo. The evaporation residue is purified by column chromatography on silica gel (toluene/ethyl acetate=5/1).

Yield: 0.37 g.

Melting point: 111°–113° C. (cyclohexane).

Calculated: C 75.26; H 7.27; N 5.32. Found: C 75.14; H 7.32; N 5.25.

EXAMPLE 38

2-Ethoxy-4-[N-(1-(2-piperidino-phenyl)-1-butyl)-amino-carbonylmethyl]-cinnamic acid A solution of ethyl 2-ethoxy-4-[N-(1-(2-piperidino-phenyl)-1-butyl)-aminocarbonyl-methyl]-cinnamate (0.49 g, 1 mmol) in ethanol (10 ml) is stirred together with 1N sodium hydroxide solution (2 ml) for 3 days at ambient temperature. The mixture is then concentrated by evaporation in vacuo, water and a few drops of methanol are added to the evaporation residue and this is then adjusted to pH 6 with 1N acetic acid. The precipitate is filtered off, dried and recrystallised from ethyl acetate.

Yield: 0.37 g.

Melting point: 175°–177° C. (decomp.).

Calculated: C 72.39; H 7.81; N 6.03. Found: 72.50; 7.88; 6.06.

EXAMPLE 39

2-Ethoxy-4-[N-(α-phenyl-2-piperidino-benzyl)-aminocarbonylmethyl]-cinnamic acid

Ethyl 2-ethoxy-4-[N-(α-phenyl-2-piperidino-benzyl)-aminocarbonylmethyl]-cinnamate (330 mg, 0.62 mmol) is dissolved in ethanol (10 ml) and, after the addition of 4N sodium hydroxide solution (4 ml), stirred for 3 hours at 50° C. Then the mixture is neutralized with 4N hydrochloric acid (4 ml), diluted with water and filtered off from the precipitate. It is then recrystallized from aqueous ethanol.

Yield: 210 mg.

Melting point: 181° C.

Calculated: C 74.67; H 6.87; N 5.62. Found: C 74.72; H 6.76; N 5.42.

EXAMPLE 40

Ethyl 3-[2-ethoxy-4-[N-(1-(2-piperidino-phenyl)-1-butyl)-aminocarbonylmethyl]-phenyl]-propionate A solution of ethyl 2-ethoxy-4-[N-(1-(2-piperidinophenyl)-1-butyl)-aminocarbonylmethyl]-cinnamate (0.54 g, 1.1 mmol) in ethanol (15 ml) is hydrogenated for 1 hour at ambient temperature and under 3 bars of hydrogen on 10% palladium/charcoal (0.1 g). The mixture is filtered, concentrated by evaporation in vacuo and the evaporation residue is crystallized from petroleum ether.

Yield: 0.30 g.

Melting point: 71°–73° C.

Calculated: C 72.84; H 8.56; N 5.66. Found: C 73.19; H 8.54; N 5.70.

EXAMPLE 41

Ethyl 3-[2-ethoxy-4-[N-(α-phenyl-2-piperidino-benzyl)-aminocarbonylmethyl]-phenyl]-propionate Prepared analogously to Example 40 by catalytic hydrogenation of ethyl 2-ethoxy-4-[N-(αphenyl-2-piperidino-benzyl)-aminocarbonylmethyl]-cinnamate and subsequent purification by column chromatography on silica gel (cyclohexane/ethyl acetate/methanol=6/1/0.5).

Melting point: 130° C. (ethanol/water).

Calculated: C 74.97; H 7.63; N 5.30. Found: C 74.65; H 7.61; N 5.15.

EXAMPLE 42

3-[2-Ethoxy-4-[N-(1-(2-piperidino-phenyl)-1-butyl)-aminocarbonylmethyl]-phenyl]-propionic acid Prepared analogously to Example 40 by catalytic hydrogenation of 2-ethoxy-4-[N-(1-(2-piperidinophenyl)-1-butyl)-aminocarbonylmethyl]-cinnamic acid.

Melting point: 112°–114° C.

Calculated: C 72.07; H 8.21; N 6.00. Found: C 72.30; H 8.21; N 6.00.

EXAMPLE 43

3-[2-Ethoxy-4-[N-(1-(2-piperidino-phenyl)-1-butyl)-aminocarbonylmethyl]-phenyl]-propionitrile Prepared analogously to Example 40 by catalytic hydrogenation of 2-ethoxy-4[N-(1-(2-piperidinophenyl)-1-butyl)-aminocarbonylmethyl]-cinnamic acid nitrile.

Melting point: 102°–103° C. (petroleum ether). Calculated: molecular peak m/e=447. Found: molecular peak m/e=447.

EXAMPLE 44

3-[2-Ethoxy-4-[N-(1-(2-piperidino-phenyl)-1-butyl)-aminocarbonylmethyl]-phenyl]-propionic acid Prepared analogously to Example 33 by alkaline saponification of ethyl 3-[2-ethoxy-4-[N-(1-(2-piperidino-phenyl)-1-butyl)-aminocarbonylmethyl]-phenyl]-propionate and subsequent purification by column chromatography (chloroform/methanol=9/1).

Melting point: 112°–115° C. (petroleum ether)

Calculated: C 72.07; H 8.21; N 6.00. Found: C 72.40; H 8.21; N 6.03.

EXAMPLE 45

3-[2-Ethoxy-4-[N-(α-phenyl-2-piperidino-benzyl)-aminocarbonylmethyl]-phenyl]-propionic acid Prepared analogously to Example 33 by alkaline saponification of ethyl 3-[2-ethoxy-4-[N-(α-phenyl-2-piperidino-benzyl)-aminocarbonylmethyl]-propionate.

Melting point: 74° C.

Calculated: C 74.37; H 7.25; N 5.60. Found: C 74.29; H 7.31; N 5.27.

EXAMPLE 46

3-[2-Ethoxy-4-[N-(1-(2-piperidino-phenyl)-1-butyl)-aminocarbonylmethyl]-phenyl]-propionitrile At ambient temperature, p-toluenesulphonic acid chloride (45.8 mg, 0.24 mmol) is added to a mixture of 3-[2-ethoxy-4-[N-(1-(2-piperidino-phenyl)-1-butyl)-aminocarbonylmethyl]-phenyl]-propionic acid amide, (56 mg, 0.12 mmol) melting point 153°–155° C. [prepared from the corresponding propionic acid by reacting with carbonyldiimidazole and then with ammonia in tetrahydrofuran] and absolute pyridine (0.044 ml). The mixture is stirred for 45 minutes at 20° C. and for 2 hours at 50° to 60° C. After cooling, water is added, the mixture is made alkaline with concentrated ammonia and extracted three times with chloroform. The combined chloroform extracts are washed with water, dried over sodium sulphate, filtered and concentrated evaporation in vacuo. The evaporation residue is purified by column chromatography on silica gel (chloroform/ethyl acetate=9/1).

Yield: 11 mg.

Calculated: molecular peak m/e=447. Found: molecular peak m/e=447.

EXAMPLE 47

Ethyl 2-ethoxy-4-[N-(α-cyclohexylmethyl-2-piperidino-benzyl)-aminocarbonylmethyl]-benzoate To a solution of α-cyclohexylmethyl-2-piperidinobenzylamine (1.13 g, 3.96 mmol) in acetonitrile (11 ml) are added, successively, 3-ethoxy-4-ethoxycarbonylphenyl acetic acid (1 g, 3.96 mmol), of triphenylphosphine (1.25 g, 4.76 mmol), triethylamine (1.11 ml, 7.92 mmol) and carbon tetrachloride (0.38 ml, 3.96 mmol) and the mixture is stirred for 15 hours at ambient temperature. It is then concentrated by evaporation in vacuo and partitioned between ethyl acetate and water. The organic extract is dried and filtered and concentrated by evaporation in vacuo. The evaporation residue is purified by column chromatography on silica gel (toluene/acetone=10/1).

Yield: 1.4 g.

Melting point: 95°–97° C. (petroleum ether/cyclohexane=1/1).

Calculated: C 73.81; H 8.52; N 5.38. Found: C 73.98; H 8.49; N 5.61.

EXAMPLE 48

Ethyl 2-ethoxy-4-[N-(α-benzyl-2-piperidino-benzyl)-aminocarbonylmethyl]-benzoate Prepared analogously to Example 47 from α-benzyl-2-piperidino-benzylamine and 3-ethoxy-4-ethoxycarbonyl-phenylacetic acid.

Melting point: 102°–105° C. (petroleum ether).

Calculated: C 74.68; H 7.44; N 5.44. Found: C 74.73; H 7.68; 5.39.

EXAMPLE 49

2-Ethoxy-4-[N-(α-cyclohexylmethyl-2-piperidinobenzyl)-aminocarbonylmethyl]-benzoic acid Ethyl 2-ethoxy-4-[N-(α-cyclohexyl-methyl-2-piperidino-benzyl)-aminocarbonylmethyl]-benzoate (1.15 g, 2.21 mmol) in ethanol (12 ml) are stirred together with 1N sodium hydroxide solution (3.3 ml) for 2 hours at 50° C. Then 1N hydrochloric acid (3.3 ml) is added and the mixture is cooled in ice. The precipitate formed is filtered off, washed with a little ice cold ethanol and dried in vacuo at 100° C.

Yield: 0.9 g.

Melting point: 153°–156° C. Calculated: C 73.14; H 8.18; N 5.69. Found: C 73.30; H 8.17; N 5.66.

EXAMPLE 50

2-Ethoxy-4-[N-(α-benzyl-2-piperidino-benzyl)-aminocarbonylmethyl]-benzoic acid

Prepared analogously to Example 49 by alkaline saponification of ethyl 2-ethoxy-4-[N-(α-benzyl-2-piperidino-benzyl)-aminocarbonylmethyl]-benzoate.

Melting point: 100°–105° C.

Calculated: C 74.05; H 7.04; N 5.76. Found: C 73.77; 7.10; N 5.50.

EXAMPLE 51

Ethyl 2-ethoxy-4-[N-(α-ethoxycarbonyl-2-piperidinobenzyl)-aminocarbonylmethyl]-benzoate To a mixture of (2-piperidino-phenyl)-glycine-ethyl ester-dihydrochloride (2 g, 5.96 mmol) in acetonitrile (12 ml) are added successively 3-ethoxy-4-ethoxycarbonyl-phenyl-acetic acid, (1.52 g, 6.75 mmol), triethylamine (2.45 ml, 17.9 mmol) and carbon tetrachloride (0.57 ml, 5.96 mmol) and the mixture is stirred overnight at ambient temperature. It is then concentrated by evaporation in vacuo and partitioned between chloroform and water. The organic extract is dried and filtered and concentrated by evaporation in vacuo. The evaporation residue is purified by column chromatography on silica gel (toluene/acetone=4/1).

Yield: 1.2 g.

Melting point: 100°–103° C. (ether).

Calculated: C 67.72; H 7.31; N 5.64. Found: C 67.87; H 7.46; N 5.61.

EXAMPLE 52

Benzyl 2-ethoxy-4-[N-(α-ethoxycarbonyl-2-piperidinobenzyl)-aminocarbonylmethyl]-benzoate Prepared analogously to Example 51 from (2-piperidinophenyl)-glycine-ethyl ester-dihydrochloride and 3-ethoxy-4-benzyloxycarbonyl-phenyl acetic acid.

Melting point: 90°–93° C.

Calculated: molecular peak m/e=558.

EXAMPLE 53

Benzyl 2-ethoxy-4-[N-(α-methoxycarbonyl-2-piperidinobenzyl)-aminocarbonylmethyl]-benzoate Prepared analogously to Example 51 from (2-piperidinophenyl)-glycine-methyl ester-dihydrochloride and 3-ethoxy-4-benzyloxycarbonyl-phenyl acetic acid.

Melting point: 100°–102° C. (ether)

Calculated: C 70.57; H 6.66; N 5.14. Found: C 70.46; H 6.67; N 5.14.

EXAMPLE 54

Benzyl 2-ethoxy-4-[N-(α-propoxycarbonyl-2-piperidinobenzyl)-aminocarbonylmethyl]-benzoate Prepared analogously to Example 51 from (2-piperidinophenyl)-glycine-n-propylester-dihydrochloride and 3-ethoxy-4-benzyloxycarbonyl-phenylacetic acid.

Melting point: 100°–102° C. (petroleum ether)

Calculated: C 71.31; H 7.04; N 4.89. Found: C 71.62; H 7.01; N 4.97.

EXAMPLE 55

Benzyl 2-ethoxy-4-[N-(α-isopropoxycarbonyl-2-piperidino-benzyl)-aminocarbonylmethyl]-benzoate Prepared analogously to Example 51 from (2-piperidinophenyl)-glycine-isopropylester-dihydrochloride and 3-ethoxy-4-benzyloxycarbonyl-phenylacetic acid.

Melting point: 85°–88° C. (acetone/petroleum ether)

Calculated: C 71.31; H 7.04; N 4.89. Found: C 71.64; H 7.10; N 4.77.

EXAMPLE 56

Ethyl 4-[N-(α-ethoxycarbonyl-2-piperidino-benzyl)-aminocarbonylmethyl]-2-hydroxy-benzoate Prepared analogously to Example 51 from (2-piperidinophenyl)-glycine-ethylester-dihydrochloride and 4-ethoxycarbonyl-3-hydroxy-phenylacetic acid.

Melting point: 107°–110° C. (petroleum ether)

Calculated: C 66.65; H 6.88; N 5.98. Found: C 66.60; H 6.86; N 6.03.

EXAMPLE 57

Ethyl 2-ethoxy-4-[N-[N-(α-hydroxymethyl-2-piperidinobenzyl)-aminocarbonylmethyl]-benzoate First, 3-ethoxy-4-ethoxycarbonyl-phenylacetic acid (2.52 g, 10 mmol) and N,N'-carbonyldiimidazole (1.62 g, 10 mmol) are heated to 70° C. for 45 minutes in absolute tetrahydrofuran (15 ml). A solution of 2-hydroxy-1-(2-piperidino-phenyl)-1-ethylamine (2.07 g, 9.4 mmol) [prepared by reducing (2-piperidino-phenyl)-glycine-ethylester with lithium aluminium hydride in ether] in absolute tetrahydrofuran (7 ml) is added thereto and the mixture is refluxed for 1 hour. After standing overnight it is diluted with ethyl acetate (50 ml) and shaken twice with water (30 ml). The organic phase is dried and filtered and concentrated by evaporation in vacuo. The evaporation residue is purified by column chromatography on silica gel (chloroform/methanol=19/1).

Yield: 2.4 g.

Melting point: 127°–128° C. (acetone)

Calculated: C 68.70; H 7.54; N 6.16. Found: C 68.80; H 7.58; N 6.15.

EXAMPLE 58

Benzyl 2-ethoxy-4-[N-(α-hydroxymethyl-2-piperidinobenyl)-aminocarbonylmethyl]-benzoate Prepared analogously to Example 57 from 3-ethoxy-4-benzyloxycarbonyl-phenylacetic acid and 2-hydroxy-1-(2-piperidino-phenyl)-1-ethylamine.

Melting point: 89°–91° C. (acetone/ether)

Calculated: C 72.07; H 7.02; N 5.42. Found: C 72.10; H 7.15; N 5.29.

EXAMPLE 59

2-Ethoxy-4-[N-(α-carboxy-2-piperidino-benzyl)-aminocarbonylmethyl]-benzoic acid Ethyl 2-ethoxy-4-[N-(α-ethoxycarbonyl-2-piperidinobenzyl)-aminocarbonylmethyl]-benzoate (0.45 g, 0.9 mmol) in ethanol (5 ml) is stirred together with 1N sodium hydroxide solution (2.7 ml) for 2 hours at 50° C. Then 1N hydrochloric acid (2.7 ml) is added and the mixture is concentrated by evaporation in vacuo. The evaporation residue is partitioned between water and chloroform. The combined chloroform extracts are shaken once with water, then the organic phase is dried, filtered and evaporated down in vacuo. The evaporation residue is crystallized with ether.

Yield: 0.27 g.

Melting point: 222°–225° C. (decomp.).

Calculated: C 65.44; H 6.41; N 6.36. Found: C 65.58; H 6.59; N 6.28.

EXAMPLE 60

4-[N-(α-Carboxy-2-piperidino-benzyl)-aminocarbonylmethyl]-2-hydroxy-benzoic acid Prepared analogously to Example 59 by alkaline saponification of ethyl 4-[N-(α-ethoxycarbonyl-2-piperidino-benzyl)-aminocarbonylmethyl]-2-hydroxybenzoate.

Melting point: 220°–228° C.

Calculated: C 64.07; H 5.87; N 6.79. Found: C 63.84; H 5.95; N 7.13.

EXAMPLE 61

2-Ethoxy-4-[N-(α-hydroxymethyl-2-piperidino-benzyl)-aminocarbonylmethyl]-benzoic acid Prepared analogously to Example 59 by alkaline saponification of ethyl 2-ethoxy-4-[N-(α-hydroxymethyl-2-piperidino-benzyl)-aminocarbonylmethyl]-benzoate and purification by column chromatography on silica gel (chloroform/ethanol=95/5).

Melting point: 80°–81° C. (decomp., sintering from 75° C.)

Calculated: molecular peak m/e=426. Found: molecular peak m/e=426.

EXAMPLE 62

Ethyl 2-ethoxy-4-[N-(α-carboxy-2-piperidinobenzyl)-amino-carbonylmethyl]-benzoate Ethyl 2-ethoxy-4-[N-(α-ethoxycarbonyl-2-piperidinobenzyl)aminocarbonylmethyl]-benzoate (0.45 g, 0.9 mmol) in ethanol (5 ml) is stirred together with 1N sodium hydroxide solution (0.90 ml) for 4 hours at ambient temperature. Then 1N hydrochloric acid (0.90 ml) is added and the mixture is evaporated down in vacuo. The residue is partitioned between water and chloroform, the chloroform solution is dried and filtered and concentrated by evaporation in vacuo. The evaporation residue is purified by column chromatography on silica gel (chloroform/ethanol=5/1).

Yield: 0.23 g.

Melting point: 177°–180° C. (ether).

Calculated: C 66.65; H 6.88; N 5.98. Found: C 66.65; H 7.11; N 5.79.

EXAMPLE 63

Ethyl 4-[N-(α-carboxy-2-piperidino-benzyl)-aminocarbonyl-methyl]-2-hydroxy -benzoate Prepared analogously to Example 62 by alkaline saponification of ethyl 4-[N-(α-ethoxycarbonyl-2-piperidino-benzyl)-aminocarbonylmethyl]-2-hydroxybenzoate.

Melting point: 156°–159° C. (ether).

Calculated: C 65.44; H 6.41; N 6.36. Found: C 65.66; H 6.38; N 6.33.

EXAMPLE 64

Benzyl 2-ethoxy-4-[N-(α-carboxy-2-piperidinobenzyl)-aminocarbonylmethyl]-benzoate Prepared analogously to Example 62 by alkaline saponification of benzyl 2-ethoxy-4-[N-(α-methoxycarbonyl-2-piperidino-benzyl)-aminocarbonyl methyl]-benzoate in dioxan.

Melting point: 140°–142° C.

Calculated: C 70.17; H 6.46; N 5.28. Found: C 70.21; H 6.50; N 5.31.

EXAMPLE 65

Ethyl 2-ethoxy-4-[N-(α-acetoxymethyl-2-piperidinobenzyl)-aminocarbonylmethyl]-benzoate To a solution of ethyl 2-ethoxy-4-[N-(α-hydroxymethyl-2-piperidino-benzyl)-aminocarbonylmethyl]-benzoate (0.227 g, 0.5 mmol) and absolute triethylamine (0.126 ml, 0.9 mmol) in absolute chloroform (3 ml), a solution of acetyl chloride (0.063 ml, 0.9 mmol) in absolute chloroform (1 ml) is added dropwise. After 4 days' stirring at ambient temperature the mixture is diluted with chloroform, washed with dilute aqueous sodium bicarbonate solution, the chloroform solution is dried and filtered and evaporated down in vacuo. The evaporation residue is purified by column chromatography on silica gel (chloroform/acetone=4/1).

Yield: 0.17 g.

Melting point: 107°–109° C. (ether/petroleum ether)

Calculated: C 67.72; H 7.31; N 5.64. Found: C 67.70; H 7.48; N 5.74.

EXAMPLE 66

Benzyl 2-ethoxy-4-[N-(α-acetoxymethyl-2-piperidinobenzyl)-aminocarbonylmethyl]-benzoate Prepared analogously to Example 65 from benzyl 2-ethoxy-4-[N-(α-hydroxymethyl-2-piperidino-benzyl)-aminocarbonylmethyl]-benzoate with acetyl chloride.

Calculated: molecular peak m/e=558. Found: molecular peak m/e=558.

EXAMPLE 67

Benzyl 2-ethoxy-4-[N-(α-propionyloxymethyl-2-piperidino-benzyl)-aminocarbonylmethyl]-benzoate Prepared analogously to Examine 65 from benzyl 2-ethoxy-4-[N-(60-hydroxymethyl-2-piperidino-benzyl)-aminocarbonylmethyl]-benzoate with propionyl chloride.

Melting point: 73°–74° C.

Calculated: C 71.31; H 7.04; N 4.89. Found: C 71.20; H 7.10; N 4.61.

EXAMPLE 68

2-Ethoxy-4-]N-(α-ethoxycarbonyl-2-piperidino-benzyl)-aminocarbonylmethyl]-benzoic acid A solution of benzyl 2-ethoxy-4-[N-(α-ethoxycarbonyl-2-piperidino-benzyl)-aminocarbonylmethyl]-benzoate (0.140 g, 0.25 mmol) in ethanol (1.4 ml) is hydrogenated with 10% palladium/charcoal (0.03 g) for 4.5 hours at 50° C. under 5 bar of hydrogen. The mixture is filtered, evaporated down in vacuo and the evaporation residue is purified by column chromatography on silica gel (chloroform/methanol=10/1).

Yield: 0.041 g.

Melting point: 115°–118° C. (petroleum ether).

Calculated: molecular peak m/e=468. Found: molecular peak m/e=468.

EXAMPLE 69

2-Ethoxy-4-[N-(α-methoxycarbonyl-2-piperidinobenzyl)-aminocarbonylmethyl]-benzoic acid Prepared analogously to Examine 68 by catalytic hydrogenation of benzyl 2-ethoxy-4-[N-(α-methoxycarbonyl-2-piperidino-benzyl)-aminocarbonylmethyl]-benzoate in methanol.

Melting point: 147°–150° C. (decomp.) (ether)

Calculated: C 66.06; H 6.65; N 6.16. Found: C 66.28; H 6.56; N 5.90.

EXAMPLE 70

2-Ethoxy-4-[N-(α-n-propoxycarbonyl-2-piperidinobenzyl)-aminocarbonylmethyl]-benzoic acid Prepared analogously to Example 68 by catalytic hydrogenation of benzyl 2-ethoxy-4-[N-(α-n-propoxycarbonyl-2-piperidino-benzyl)-aminocarbonyl methyl]-benzoate in n-propanol.

Melting point: 122°–125° C. (ether/petroleum ether=1/1).

Calculated: C 67.20; H 7.10; H 5.80. Found: C 67.39; H 7.24; H 5.78.

EXAMPLE 71

2-Ethoxy-4-[N-(α-isopropoxycarbonyl-2-piperidinobenzyl)-aminocarbonylmethyl]-benzoic acid Prepared analogously to Example 68 by catalytic hydrogenation of benzyl 2-ethoxy-4-[N-(α-isopropoxycarbonyl-2-piperidino-benzyl)-aminocarbonylmethyl]-benzoate in isopropanol.

Melting point: 149°–151° C. (acetone/petroleum ether)

Calculated: C 67.20; H 7.10; N 5.80. Found: C 67.50; H 6.99; N 5.78.

EXAMPLE 72

2-Ethoxy-4-[N-(α-acetoxymethyl-2-piperidino-benzyl)-aminocarbonylmethyl]-benzoic acid Prepared analogously to Example 68 by catalytic hydrogenation of benzyl 2-ethoxy-4-[N-(α-acetoxymethyl-2-piperidino-benzyl)-aminocarbonylmethyl]-benzoate in ethanol.

Calculated: molecular peak m/e=468. Found: molecular peak m/e=468.

EXAMPLE 73

2-Ethoxy-4-[N-(α-propionyloxymethyl-2-piperidinobenzyl)-aminocarbonylmethyl]-benzoic acid Prepared analogously to Example 68 by catalytic hydrogenation of benzyl 2-ethoxy-4-[N-(α-propionyloxymethyl-2-piperidino-benzyl)-aminocarbonylmethyl]-benzoate in ethanol.

Melting point: 64°–67° C. (ethanol/water).

Calculated: molecular peak m/e=482. Found: molecular peak m/e=482.

EXAMPLE 74

2-Hydroxy-4-[N-(α-isopropoxycarbonyl-2-piperidino-benzyl)-aminocarbonylmethyl]-benzoic acid Boron tribromide (0.04 ml, 0.414 mmol) is added at −20° C. with the exclusion of moisture to a stirred solution of 2-ethoxy-4-[N-(α-isopropoxycarbonyl-2-piperidino-benzyl)-amino-carbonylmethyl]-benzoic acid (0.20 g, 0.414 mmol) in 1,2-dichloroethane (5 ml). The mixture is allowed to come up to ambient temperature and is then stirred for 2 hours. It is poured into isopropanol, the mixture is concentrated by evaporation in vacuo, water is added and the mixture is extracted with chloroform. The organic extract is dried and filtered and evaporated down in vacuo. The evaporation residue is purified by column chromatography on silica gel (chloroform methanol/glacial acetic acid=5/1/0.01).

Yield: 0.14 g.

Melting point: 190°–200° C. (ether).

Calculated: molecular peak m/e=454. Found: molecular peak m/e=454.

EXAMPLE 75

Ethyl 2-ethoxy-4-[N-(α-ethoxymethyl-2-piperidino-benzyl)-aminocarbonylmethyl]-benzoate Ethyl 2-ethyl-4-[N-(α-hydroxymethyl-2-piperidino-benzyl)-aminocarbonylmethyl]-benzoate (0.64 g, 1.4 mmol)

is added with stirring at ambient temperature to sodium hydride (0.061 g, 1.4 mmol) (55% in oil) in absolute tetrahydrofuran (6.4 ml). The mixture is stirred for 1 hour, then ethyl iodide (0.113 ml, 1.4 mmol) is added and the mixture is stirred for a further 16 hours at ambient temperature. Then ethanol (2 ml) is added and the mixture is evaporated down in vacuo. The evaporation residue is partitioned between chloroform and water. The organic phase is washed twice with water, dried, filtered and concentrated by evaporation in vacuo. The evaporation residue is purified by column chromatography on silica gel (chloroform/acetone=17/3).

Yield: 0.05 g.

Melting point: 85°–87° C. (petroleum ether).

Calculated: molecular peak m/e=482. Found: molecular peak m/e=482.

EXAMPLE 76

2-Ethoxy-4-[N-(α-ethoxymethyl-2-piperidino-benzyl)-aminocarbonylmethyl]-benzoic acid Prepared analogously to Example 31 by alkaline saponification of ethyl 2-ethoxy-4-[N-(α-ethoxymethyl-2-piperidino-benzyl)-aminocarbonylmethyl]-benzoate.

Calculated: molecular peak m/e=454. Found: molecular peak m/e=454.

EXAMPLE 77

4-[N-(α-Carboxy-2-piperidino-benzyl)-aminocarbonylmethyl]-2-hydroxy-benzoic acid Prepared analogously to Example 74 by reacting 2-ethoxy-4-[N-(α-isopropoxycarbonyl-2-piperidinobenzyl)-aminocarbonylmethyl]-benzoic acid with 2.5 equivalents of boron tribromide in methylene chloride.

Melting point: 220°–230° C. (water).

Calculated: C 64.07; H 5.87; N 6.79. Found: C 64.21; H 5.99; N 6.81.

EXAMPLE 78

3-[2-Ethoxy-4-[N-(1-(2-piperidino-phenyl)-1-butyl)-aminocarbonylmethyl]-phenyl]-propionitrile Magnesium chips (0.11 g, 4.5 mmol) are added to 2-ethoxy-4-[N-(1-(2-piperidino-phenyl)-1-butyl)-aminocarbonylmethyl]-cinnamic acid nitrile (0.05 g, 0.11 mmol) in methanol (1.1 ml) and the mixture is stirred for 45 minutes at 25° C. and for 1 hour at 0° C. It is then cooled to 0° C. and mixed with of 1N hydrochloric acid (4.5 ml). It is diluted with water, filtered over kieselguhr and extracted with chloroform. The chloroform extract is washed with aqueous sodium bicarbonate solution, dried and filtered and concentrated by evaporation in vacuo. The evaporation residue is purified by column chromatography on silica gel (chloroform/ethyl acetate=9/1).

Yield: 0.015 g.

Melting point: 102°–104° C. (petroleum ether).

Calculated: molecular peak m/e=447. Found: molecular peak m/e=447.

EXAMPLE 79

[2-Ethoxy-4-[N-(1-(2-piperidino-phenyl)-3-methyl-1-butyl)-aminocarbonylmethyl]-phenyl]-acetonitrile Prepared analogously to Example 29 from 2-ethoxy-4-[N-(1-(2-piperidino-phenyl)-3-methyl-1-butyl)-aminocarbonylmethyl]benzyl chloride with sodium cyanide.

Melting point: 135°–136° C.

Calculated: C 75.13; H 8.33; N 9.39. Found: C 75.12; H 8.18; N 9.18.

EXAMPLE 80

Ethyl 2-ethoxy-4-[N-(α-cyclopropylmethyl-2-piperidino-benzyl)-aminocarbonylmethyl]-benzoate Prepared analogously to Example 47 from α-cyclopropylmethyl-2-piperidino-benzylamine and 3-ethoxy-4-ethoxycarbonyl-phenylacetic acid.

Melting point: 126°–127° C.

Calculated: C 72.77; H 8.00; N 5.85. Found: C 72.85; H 7.74; N 5.84.

EXAMPLE 81

2-Ethoxy-4-[N-(α-cyclopropylmethyl-2-piperidino-benzyl)-aminocarbonylmethyl]-benzoic acid hemihydrate Prepared analogously to Example 49 by alkaline saponification of ethyl 2-ethoxy-4-[N-(α-cyclopropylmethyl-2-piperidino-benzyl)-aminocarbonylmethyl]-benzoate.

Melting point: 103°–104° C.

Calc. (x 0.5 $H_2O$): C 70.55; H 7.68; N 6.10. Found: C 70.67; H 7.67; N 6.37.

EXAMPLE 82

Ethyl 2-ethoxy-4-[N-(α-cyclobutylmethyl-2-piperidino-benzyl)-aminocarbonylmethyl]-benzoate Prepared analogously to Example 47 from α-cyclobutylmethyl-2-piperidino-benzylamine and 3-ethoxy-4-ethoxycarbonyl-phenyl acetic acid.

Melting point: 116°–118° C.

Calculated: C 73.14; H 8.18; N 5.69. Found: C 73.14; H 8.32; N 5.64.

EXAMPLE 83

2-Ethoxy-4-[N-(α-cyclobutylmethyl-2-piperidino-benzyl)-aminocarbonylmethyl]-benzoic acid Prepared analogously to Example 49 by alkaline saponification of ethyl 2-ethoxy-4-[N-(α-cyclobutylmethyl-2-piperidino-benzyl)-aminocarbonyl methyl]-benzoate.

Melting point: 140°–142° C.

Calculated: C 72.39; H 7.81; N 6.03. Found: C 72.15; H 7.79; N 5.97.

EXAMPLE 84

Ethyl 2-ethoxy-4-[N-(α-cyclopenthylmethyl-2-piperidino-benzyl)-aminocarbonylmethyl]-benzoate Prepared analogously to Example 47 from α-cyclopenthylmethyl-2-piperidino-benzylamine and 3-ethoxy-4-ethoxycarbonyl-phenyl-acetic acid.

Melting point: 120°–121° C.

Calculated: C 73.49; H 8.36; N 5.53. Found: C 73.31; H 8.55; N 5.39.

EXAMPLE 85

2-Ethoxy-4-[N-(α-cyclopenthylmethyl-2-piperidino-benzyl)-aminocarbonylmethyl]-benzoic acid Prepared analogously to Example 49 by alkaline saponification of ethyl 2-ethoxy-4-[N-(α-cyclopenthyl-methyl-2-piperidino-benzyl)-aminocarbonylmethyl]-benzoate.

Melting point: 85°–88° C.

Calculated: C 72.77; H 8.00; N 5.85. Found: C 72.50; H 8.02; N 6.03.

EXAMPLE 86

Ethyl 2-ethoxy-4-[N-(2-piperidino-α-(tetrahydrofuran-2-yl-methyl)-benzyl)-aminocarbonylmethyl]-benzoate Prepared analogously to Example 47 from 2-piperidino-α-(tetrahydrofuran-2-yl-methyl)-benzylamine and 3-ethoxy-4-ethoxycarbonyl-phenylacetic acid.

Melting point: 111°–113° C.

Calculated: C 70.84; H 7.93; N 5.51. Found: C 70.76; H 7.73; N 5.51.

EXAMPLE 87

2-Ethoxy-4-[N-(2-piperidino-α-(tetrahydrofuran-2-ylmethyl)-benzyl)-aminocarbonylmethyl]-benzoic acid Prepared analogously to Example 49 by alkaline saponification of ethyl 2-ethoxy-4-[N-(2-piperidino-α-(tetrahydrofuran-2-yl-methyl)-benzyl)-aminocarbonylmethyl]-benzoate.

Melting point: 121°–123° C.

Calculated: C 69.98; H 7.55; N 5.83. Found: C 69.90; H 7.78; N 5.71.

EXAMPLE 88

Ethyl 2-ethoxy-4-[N-(α-cycloheptylmethyl-2-piperidino-benzyl)-aminocarbonylmethyl]-benzoate Prepared analogously to Example 47 from α-cycloheptylmethyl-benzylamine and 3-ethoxy-4-ethoxycarbonyl-phenylacetic acid.

Melting point: 96°–98° C.

Calculated: C 74.12; H 8.67; N 5.24. Found: C 74.40; H 8.87; N 5.39.

EXAMPLE 89

2-Ethoxy-4-[N-(α-cycloheptylmethyl-2-piperidino-benzyl)-aminocarbonylmethyl]-benzoic acid Prepared analogously to Example 49 by alkaline saponification of ethyl 2-ethoxy-4-[N-(α-cycloheptylmethyl-2-piperidino-benzyl)-aminocarbony lmethyl]-benzoate.

Melting point: 127°–130° C.

Calculated: C 73.49; H 8.36; N 5.53. Found: C 73.54; H 8.62; N 5.47.

EXAMPLE 90

Ethyl 2-ethoxy-4-[N-(α-cyclohexylmethyl-2-piperidino-benzyl)-aminocarbonylmethyl]-benzoate a) Ethyl 2-ethoxy-4-[N-(α-(cyclohexyl-methylidene)-2-piperidino-benzyl)-amino carbonylmethyl]-benzoate Prepared analogously to Example 47 from α-cyclohexylmethyl-(2-piperidino-phenyl)-ketimine and 3-ethoxy-4-ethoxycarbonyl-phenylacetic acid.

Melting point: 85°–88° C.

Calculated: C 74.10; H 8.16; N 5.10. Found: C 74.37; H 8.00; N 5.45.

According to the 80 MHz-$^1$H-NMR spectrum ($CDCl_3$) there is a mixture of E/Z=½. [Olefinic H: (E) D 6.26, (Z) 5.42 ppm].

b) Ethyl 2-ethoxy-4-[N-(α-cyclohexylmethyl-2-piperidino-benzyl)-aminocarbonylmethyl]-benzoate Prepared analogously to Example 40 by catalytic hydrogenation of ethyl 2-ethoxy-4-[N-(α-cyclohexylmethylidene)-2-piperidino-benzyl)-aminocarbonylmethyl]-benzoate.

Melting point: 95°–97° C.

Calculated: C 73.81; H 8.52; N 5.38. Found: C 73.92; H 8.74; N 5.29.

EXAMPLE 91

2-Ethoxy-4-[N-(α-cyclohexylmethyl-2-piperidino-benzyl)-aminocarbonylmethyl]-benzoic acid a) 2-Ethoxy-4-[N-(α-cyclohexyl-methylidene)-2-piperidino-benzyl)-aminocarbonylmethyl]-benzoic acid Prepared analogously to Example 49 by alkaline saponification of ethyl 2-ethoxy-4-[N-(α-(cyclohexyl-methylidene)-2-piperidino-benzyl)-aminocarbonylmethyl]-benzoate.

Melting point: 95°–100° C.

Calculated: C 73.44; H 7.81; N 5.71. Found: C 73.38; H 7.73; N 5.75.

b) 2-Ethoxy-4-[N-(α-cyclohexylmethyl-2-piperidino-benzyl)-aminocarbonylmethyl]-benzoic acid Prepared analogously to Example 40 by catalytic hydrogenation of 2-ethoxy-4-[N-(α-cyclohexylmethylidene)-2-piperidino-benzyl)-aminocarbonylmethyl]benzoic acid.

Melting point: 154°–156° C.

Calculated: C 73.14; H 8.18; N 5.69. Found: C 73.31; H 8.25; N 5.71.

EXAMPLE 92

Ethyl 2-ethoxy-4-[N-(1-(2-piperidino-phenyl)-3-buten-1-yl)-aminocarbonylmethyl]-benzoate Prepared analogously to Example 47 from 1-(2-piperidino-phenyl)-3-buten-1-yl-amine and 3-ethoxy-4-ethoxycarbonyl-phenylacetic acid.

Melting point: 110°–112° C.

Calculated: C 72.39; H 7.81; N 6.03. Found: C 72.10; H 7.66; N 5.94.

EXAMPLE 93

Ethoxy-4-[N-(1-(2-piperidino-phenyl)-3-buten-1-yl)-aminocarbonylmethyl]-benzoic acid Prepared analogously to Example 49 by alkaline saponification of ethyl 2-ethoxy-4-[N-(1-(2-piperidino-phenyl)-3-buten-1-yl)-aminocarbonylmethyl]-benzoate.

Melting point: 92°–95° C.

Calculated: C 71.53; H 7.39; N 6.42. Found: C 71.27; H 7.42; N 6.42.

EXAMPLE 94

Ethyl 2-ethoxy-4-[N-(1-(2-piperidino-phenyl)-3-methyl-3-buten-1-yl)-aminocarbonylmethyl]-benzoate Prepared analogously to Example 47 from 3-methyl-1-(2-piperidino-phenyl)-3-buten-1-yl)-amine and 3-ethoxy-4-ethoxycarbonyl-phenylacetic acid.

Melting point: 126°–128° C.

Calculated: C 72.77; H 8.00; N 5.85. Found: C 72.82; H 8.22; N 5.78.

EXAMPLE 95

2-Ethoxy-4-[N-(1-(2-piperidino-phenyl)-3-methyl-3-buten-1-yl)-aminocarbonylmethyl]-benzoic acid Prepared analogously to Example 49 by alkaline saponification of ethyl 2-ethoxy-4-[N-(1-(2-piperidino-phenyl)-3-methyl-3-buten-1-yl)-aminocarbonylmethyl]-benzoate.

Melting point: 64°–66° C.

Calculated: C 71.97; H 7.61; N 6.22. Found: C 71.70; H 7.50; N 5.98.

EXAMPLE 96

Ethyl 2-ethoxy-4-[N-(1-(2-piperidino-phenyl)-3-methyl-2-buten-1-yl)-aminocarbonylmethyl]-benzoate[with 25% of ethyl 2-ethoxy-4-[N-(1-(2-piperidino-phenyl)-3-methyl-1-butyl)-aminocarbonylmethyl]-benzoate]

Prepared analogously to Example 47 from 3-methyl-1-(2-piperidino-phenyl)-2-buten-1-yl-amine [containing 25% of 3-methyl-1-(2-piperidino-phenyl)-1-butylamine] and 3-ethoxy-4-ethoxycarbonylphenylacetic acid.

Melting point: 141°–142° C.

Calculated: C 72.77; H 8.00; N 5.85. Found: C 72.60; H 7.77; N 5.73.

The mixing ratio of 75/25 is obtained from the corresponding ratio of intensities of the particularly characteristics signals in the 400 MHz-$^1$H-NMR spectrum ($CDCl_3$). The position of the signals is: 3-methyl-2-buten-1-yl compound: olefinic H: 5.25 (d), $CH_3$: 1.64 (s) and 1.77 (s), benzylic <CH—6.00 (t), benzylic $CH_2$—; 3.52 ppm (s) 3-methyl-1-butyl compound: $CH_3$: 0.90 (d), benzylic <CH—5.35 (m), benzylic —$CH_2$—; 3.54 ppm (s).

EXAMPLE 97

2-Ethoxy-4-[N-(1-(2-piperidino-phenyl)-3-methyl-2-buten-1-yl)-aminocarbonylmethyl]-benzoic acid [containing 25% of 2-ethoxy-4-[N-(1-(2-piperidino-phenyl)-3-methyl-1-butyl)-aminocarbonylmethyl]-benzoic acid]

Prepared analogously to Example 49 by alkaline saponification of the corresponding ethyl ester mixture from Example 68.

Melting point: 154°–156° C.

Calculated: C 71.97; H 7.61; N 6.22. Found: C 71.80; H 7.57; N 5.98.

EXAMPLE 98

Ethyl 2-ethoxy-4-[N-(1-(2-piperidino-phenyl)-3-butyn-1-yl)-aminocarbonylmethyl]-benzoate Prepared analogously to Example 47 from 1-(2-piperidino-phenyl)-3-butyn-1-yl-amine and 3-ethoxy-4-ethoxycarbonyl-phenylacetic acid.

Melting point: 86°–90° C.

Calculated: C 72.70; H 7.41; N 6.06. Found: C 72.60; H 7.40; N 6.04.

EXAMPLE 99

2-Ethoxy-4-[N-(1-(2-piperidino-phenyl)-3-butyn-1-yl)-aminocarbonylmethyl]-benzoic acid Prepared analogously to Example 21 by alkaline saponification of ethyl 2-ethoxy-4-[N-(1-(2-piperidino-phenyl)-3-butyn-1-yl)-aminocarbonylmethyl]-benzoate.

Melting point: 66°–69° C.

Calculated: C 71.87; H 6.96; N 6.45. Found: C 71.60; H 6.95; N 6.38.

EXAMPLE 100

Ethyl 2-ethoxy-4-[N-(1-(2-piperidino-phenyl)-4-penten-1-yl)-aminocarbonylmethyl]-benzoate Prepared analogously to Example 47 from 1-(2-piperidino-phenyl)-4-penten-1-yl-amine and 3-ethoxy-4-ethoxycarbonyl-phenylacetic acid.

Melting point: 117°–120° C.

Calculated: C 72.77; H 8.00; N 5.85. Found: C 72.73; H 7.97; N 6.07.

EXAMPLE 101

2-Ethoxy-4-[N-(1-(2-piperidino-phenyl)-4-penten-1-yl)-aminocarbonylmethyl]-benzoic acid Prepared analogously to Example 49 by alkaline saponification of ethyl 2-ethyl 2-ethoxy-4-[N-(1-(2-piperidino-phenyl)-4-penten-1-yl)-aminocarbonylmethyl]-benzoate.

Melting point: 82°–85° C.

Calculated: C 71.97; H 7.61; N 6.22. Found: C 71.97; H 7.59; N 5.98.

EXAMPLE 102

Ethyl 2-ethoxy-4-[N-(1-(2-piperidino-α-(tetrahydropyran-2-yl-methyl)-benzyl)-aminocarbonylmethyl]-benzoate Prepared analogously to Example 47 from 2-piperidino-α-(tetrahydropyran-2-yl-methyl)-benzylamine and 3-ethoxy-4-ethoxycarbonyl-phenylacetic acid.

Melting point: 82°–85° C.

Calculated: C 71.24; H 8.10; N 5.36. Found C 71.28; H 7.96; N 5.29.

EXAMPLE 103

2-Ethoxy-4-[N-(1-(2-piperidino-α-(tetrahydropyran-2-yl-methyl)-benzyl)-aminocarbonylmethyl]-benzoic acid Prepared analogously to Example 49 by alkaline saponification of ethyl 2-ethoxy-4-[N-(1-(2-piperidino-α-(tetrahydropyran-2-yl-methyl)-benzyl)-aminocarbonylmethyl]- benzoate.

Melting point: 140°–142° C. (sinters from 70° C., partial softening at 105° C.).

Calculated: C 70.42; H 7.74; N 5.66. Found: H 7.88; N 5.40.

Ethyl 2-ethoxy-4-[N-(α-cyclohexylmethyl-2-piperidino-benzyl)-aminocarbonylmethyl]-benzoate At 23°–25° C., a solution of 2-ethoxy-4-cyanomethyl-benzoate (2.35 g, 10 mmol) and α-cyclohexylmethyl-2-piperidino-benzyl alcohol (2.88 g, 10 mmol) in o-dichlorobenzene (15 ml) is added dropwise to a mixture of concentrated sulphuric acid (15 ml) and o-dichlorobenzene (15 ml). The mixture is stirred for 2 hours at ambient temperature. The o-dichlorobenzene phase is then separated off and the residue is added to ice. After being made alkaline with soda solution, it is extracted with chloroform. The extracts are dried over sodium sulphate and concentrated by evaporation. The residue is purified by column chromatography on silica gel (toluene/acetone=10/1).

Yield: 1.1 g.

Melting point: 95°–97° C.

Calculated: C 73.81; H 8.52; N 5.38. Found: C 73.95; H 8.64; N 5.42.

EXAMPLE 105

Benzyl 2-ethoxy-4-[N-(α-methoxycarbonyl-2-piperidino-benzyl)-aminocarbonylmethyl]-benzoate Potassium carbonate (0.28 g, 2 mmol) is added to a solution of benzyl 2-ethoxy-4-[N-(α-carboxy-2-piperidino-benzyl)-aminocarbonylmethyl]-benzoate (1.06 g, 2 mmol) in anhydrous dimethyl formamide (8 ml). The mixture is stirred for 10 minutes at ambient temperature, then methyl iodide (0.125 ml, 2 mmol) is added and the resulting mixture is stirred overnight at ambient temperature. It is filtered and the filtrate is concentrated by evaporation to dryness in vacuo. The evaporation residue is partitioned between aqueous sodium bicarbonate solution (pH=9) and methylene chloride. The organic phase was poured over sodium sulphate, filtered and concentrated by evaporation in vacuo. The evaporation residue is purified by column chromatography on silica gel (toluene/acetone=4/1) and crystallised from ether/petroleum ether.

Yield: 0.56 g.

Melting point: 100°–102° C.

Calculated: C 70.57; H 6.66; N 5.14. Found C70.69; H 6.71; N 5.29.

EXAMPLE 106

(S) 2-Ethoxy-4-[N-(1-(2-piperidino-phenyl)-3-methyl-1-butyl)-aminocarbonylmethyl]benzoic acid a) (S)-3-Methyl-1-(2-piperidino-phenyl)-1-butylamine Equimolar quantities of racemic 3-methyl-1-(2-piperidino-phenyl)-1-butylamine and of N-acetyl-L-glutamic acid were refluxed in aceton, whereby methanol was added in such an amount to yield a clear solution.

After cooling over night up to 20° C., the obtained crystals were suction filtered and twice washed with aceton cooled to −15° C. The obtained product [M.p.: 163°–166° C. $[\alpha]_D^{20}$=+0,286° (c=1 in methanol)] was recrystallised from aceton under addition of methanol, whereby (S)-3-methyl-1-(2-piperidino-phenyl)-1-butylamine as N-acetyl-L-glutamic acid addition salt was obtained in a yield of 60,4% of theory.

M.p.: 168°–171° C.

$[\alpha]_{20}^{D}$+0,356° (c=1 in methanol).

The free amine was obtained after reacting with sodium hydroxide solution.

b) (S) Ethyl 2-ethoxy-4-[N-(1-(2-piperidino-phenyl)-3-methyl-1-butyl)-aminocarbonylmethyl]benzoate Prepared from (S)-3-Methyl-1-(2-piperidino-phenyl)-1-butylamine and 3-ethoxy-4-ethoxycarbonyl-phenylacetic acid analogously to Example 1.

Yield: 77% of theory.

M.p.: 121°–123° C. (petroleum ether/aceton=7.1).

$[\alpha]_{20}^{D}$+7,82° (c=1 in methanol).

c) (S) 2-Ethoxy-4-[N-(1-(2-piperidino-phenyl)-3-methyl-1-butyl)-aminocarbonylmethyl]benzoic acid Prepared from (S) Ethyl 2-ethoxy-4-[N-(1-(2-piperidino-phenyl)-3-methyl-1-butyl)-aminocarbonylmethyl]benzoate by saponification analogously to Example 4.

Yield: 75.9% of theory.

M.p.: 102°–104° C. (petroleum ether/toluene).

$[\alpha]_{20}^{D}$+7,80° (c=1,025 in methanol).

The compounds of the present invention, that is, those embraced by formula I above, including forms (A), (B) and (C) of 2-ethoxy-4-[N-{1-(2-piperidino-phenyl)-3-methyl-1-butyl}-aminocarbonylmethyl]-benzoic acid, their enantiomers and their non-toxic, pharmacologically acceptable salts formed with inorganic or organic acids or bases, have useful pharmacodynamic properties. More particularly, they have a favorable effect on the intermediate metabolism and exhibit hypoglycemic activity in warm-blooded animals such as rats.

The hypoglycemic activity of the compounds of the instant invention was ascertained by the standard pharmacological test method described below, and the table which follows shows the results of this test for a few representative species of the genus, where A=2-methoxy-4-[N-{1-(2-piperidino-phenyl)-1-ethyl}-aminocarbonylmethyl]-benzoic acid, B=2-ethoxy-4-[N-{1-(2-piperidino-phenyl)-1-butyl}-aminocarbonylmethyl]-benzoic acid, C=2-methoxy-4-[N-(α-phenyl-2-piperidino-benzyl) aminocarbonylmethyl]-benzoic acid, D=2-ethoxy-4-[N-(α-phenyl-2-piperidino-benzyl) aminocarbonylmethyl]-benzoic acid, E=(+)-2-ethoxy-4-[N-{1-(2-piperidino-phenyl)-1-butyl}aminocarbonylmethyl]-benzoic acid, F=2-ethoxy-4-[N-{1-(2-piperidino-phenyl)-1-ethyl}aminocarbonylmethyl]-benzoic acid, G=Sodium 2-ethoxy-4-[N-{1-(2-pyrrolidino-phenyl)-1-butyl}aminocarbonylmethyl]-benzoate, H=2-ethoxy-4-[N-{1-(2-hexamethyleneimino-phenyl)-1-butyl}-aminocarbonylmethyl]-benzoic acid, I=2-methoxy-4-(N-{1-(2-piperidino-phenyl)-1-butyl}aminocarbonylmethyl]-benzoic acid, K=2-n-propoxy-4-[N-{1-(2-piperidino-phenyl)-1-butyl}aminocarbonylmethyl]-benzoic acid, L=2-ethoxy-4-[N-{1-(2-piperidino-phenyl)-1-pentyl}aminocarbonylmethyl]-benzoic acid, M=2-ethoxy-4-[N-(4-methyl-α-phenyl-2-piperidino-benzyl)aminocarbonylmethyl]-benzoic acid, N=form (B) of 2-ethoxy-4-[N-{1-(2-piperidino-phenyl)-3-methyl-1-butyl}-aminocarbonylmethyl]-benzoic acid, O=[2-ethoxy-4-[N-(1-(2-piperidino-phenyl)-1-butyl)-aminocarbonylmethyl]-phenyl]-acetonitrile, P=[2-ethoxy-4-[N-(α-phenyl-2-piperidino-benzyl)-aminocarbonylmethyl]-phenyl]acetonitrile, Q=2-ethoxy-4-[N-(α-cyclohexylmethyl-2-piperidino-benzyl)-aminocarbonylmethyl]-benzoic acid, R=2-ethoxy-4-[N-(α-ethoxycarbonyl-2-piperidino-benzyl) aminocarbonylmethyl]-benzoic acid, S=2-ethoxy-4-[N-(α-methoxycarbonyl-2-piperidino-benzyl)aminocarbonylmethyl]benzoic acid, T=2-ethoxy-4-[N-(α-isopropoxycarbonyl-2-piperidino-benzyl)-aminocarbonylmethyl]benzoic acid, U=2-ethoxy-4-[N-(α-cyclopropylmethyl-2-piperidino-benzyl)-aminocarbonylmethyl]benzoic acid, V=2-ethoxy-4-[N-(α-(tetrahydrofuran-2-yl-methyl)-2-piperidino-benzyl)-aminocarbonylmethyl]benzoic acid, W=2-ethoxy-4-[N-(1-(2-piperidino-phenyl)-3-buten-1-yl) aminocarbonylmethyl]benzoic acid, X=2-ethoxy-4-[N-(1-(2-piperidino-phenyl)-3-methyl-3-buten-1-yl)-aminocarbonylmethyl]benzoic acid and Y=2-ethoxy-4-[N-(1-(2-piperidino-phenyl)-3-butyn-1-yl) aminocarbonylmethyl]benzoic acid,

TEST FOR HYPOGLYCEMIC ACTIVITY the hypoglycemic activity of the test compounds was ascertained on female rats of a particular strain weighing from 180–220 g which had been fasted for 24 hours before the start of the test. The test compounds were suspended in 1.5% methyl cellulose immediately before the start of the test and administered by esophageal tube.

Blood samples were taken immediately before the administration of the test compound and 1, 2, 3 and 4 hours afterwards, in each case from the retroorbital Venous plexus. 50 $\mu$l of each sample were deproteinated with 0.5 ml of 0.33N perchloric acid and centrifuged. The glucose in the supernatant fluid was measured using the hexokinase method with the aid of an analytical photometer. The statistical evaluation was made using the t-test according to Student with p=0.05 as the limit of significance.

The following tables show the changes in glucose content in percent compared with the control:

TABLE I

| | 1 mg/kg | | | | 0.5 mg/kg | | | |
|---|---|---|---|---|---|---|---|---|
| Compound | 1 | 2 | 3 | 4 h | 1 | 2 | 3 | 4 h |
| A | −37 | −46 | −23 | −14 | | | | |
| B | −38 | −49 | −38 | −33 | −43 | −36 | −34 | −35 |
| C | −38 | −41 | −38 | −34 | | | | |
| D | −42 | −54 | −37 | −34 | | | | |
| E | | | | | −40 | −39 | −36 | −36 |
| F | −44 | −44 | −40 | −30 | | | | |
| G | | | | | −40 | −33 | −30 | −17 |
| H | | | | | −42 | −34 | −18 | n.s. |
| I | | | | | −42 | −39 | −37 | −30 |
| K | | | | | −34 | −36 | −24 | n.s. |
| L | | | | | −42 | −45 | −38 | −39 |
| M | −44 | −41 | −35 | −27 | | | | |
| O | −29 | −37 | −35 | −34 | | | | |
| P | −12 | −10 | −14 | −14 | | | | |
| Q | | | | | −22 | −47 | −45 | −45 |
| R | −33 | −17 | n.s. | n.s. | | | | |
| S | −42 | −35 | −28 | −18 | | | | |
| T | −36 | −21 | −18 | n.s. | | | | |
| U | | | | | −45 | −45 | −36 | −36 |
| V | | | | | −46 | −25 | −13 | −10 |
| W | | | | | −42 | −39 | −28 | −35 |
| X | | | | | −44 | −41 | −31 | −28 |
| Y | | | | | −33 | −18 | −11 | n.s. |

n.s. = not statistically significant

TABLE II

| | 0.1 mg/kg | | | |
|---|---|---|---|---|
| Compound | 1 | 2 | 3 | 4 h |
| N | −38 | −44 | −41 | −40 |

In the tests for hypoglycemic activity, no toxic side effects were observed, even at a dosage of 10 mg/kg p.o., with any of these compounds.

The novel compounds are virtually non-toxic; for example, after a single dose of 2,000 mg/kg p.o. (suspension in 1% methyl cellulose) of compounds B and D to 5 male and 5 female mice, only one animal in this group died during the observation period of 14 days.

The toxic effect of a single dose of compound N administered orally (suspended in 1% methyl cellulose) was tested in male and female mice of our own strain weighing from 20–26 g over an observation period of 14 days.

TABLE III

| Compound | Approximate acute toxicity | |
|---|---|---|
| N | >1000 mg/kg p.o. | (0 out of 6 animals died) |

By virtue of their pharmacological properties, the compounds of the present invention are useful for the treatment of diabetes mellitus.

For pharmaceutical purposes the compounds of the present invention are administered to warm-blooded animals perorally or parenterally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups and the like. An effective amount of the compounds of the present invention is from 0.014 to 0.71 mgm/kg body weight, preferably 0.035 to 0.29 mgm/kg body weight, once or twice daily.

The following examples illustrates a few pharmaceutical compositions comprising a compound of the present invention as an active ingredient and represent the best modes contemplated of using the invention. The parts are parts by weight unless otherwise specified.

EXAMPLE 107

Tablets containing 5 mg of 2-ethoxy-4-[N-{1-(2-piperidinophenyl)-3-methyl-1-methyl-1-butyl}-aminocarbonylmethyl]-benzoic acid, form (B)

The tablet composition is compounded from the following ingredients:

| | | |
|---|---|---|
| Active ingredient | (1) | 5.0 parts |
| Corn starch | (2) | 62.0 parts |
| Lactose | (3) | 48.0 parts |
| Polyvinylpyrrolidone | (4) | 4.0 parts |
| Magnesium stearate | (5) | 1.0 parts |
| | | 120.0 parts |

Preparation

Ingredients (1), (2), (3) and (4) are mixed together and moistened with water. The moist mixture is passed through a 1.5 mm mesh screen and dried at about 45° C. The dry granulate is passed through a 1.0 mm mesh screen and mixed with ingredient (5). The finished mixture is compressed into 120 mg-tablets.

EXAMPLE 108

Coated tablets containing 2.5 mg of 2-ethoxy-4-[N-{1-(2-piperidino-phenyl)-3-methyl-1-butyl}-aminocarbonylmethyl]benzoic acid, form (A)

The tablet core composition is compounded from the following ingredients:

| | | |
|---|---|---|
| Active ingredient | (1) | 2.5 parts |
| Potato starch | (2) | 44.0 parts |

-continued

| | | |
|---|---|---|
| Lactose | (3) | 30.0 parts |
| Polyvinylpyrrolidone | (4) | 3.0 parts |
| Magnesium stearate | (5) | 0.5 parts |
| | | 80.0 parts |

Preparation

Ingredients (1), (2), (3) and (4) are thoroughly mixed and moistened with water. The moist mass is passed through a 1 mm-mesh screen, dried at about 45° C., and the granulate is then passed through the same screen. After ingredient (5) has been added, convex 80 mg-tablet cores are compressed in a tablet-making machine. The tablet cores thus produced are covered in known manner with a coating consisting essentially of sugar and talc. The finished tablets are polished with wax. Weight of each coated tablet: 120 mg.

EXAMPLE 109

Tablets containing 10 mg of 2-ethoxy-4-[N-(α-phenyl-2-piperidino-benzyl)-aminocarbonylmethyl]-benzoic acid The tablet composition is compounded from the following ingredients:

| | |
|---|---|
| Active ingredient | 10.0 parts |
| Powdered lactose | 70.0 parts |
| Corn starch | 31.0 parts |
| Polyvinylpyrrolidone | 8.0 parts |
| Magnesium stearate | 1.0 parts |
| | 120.0 parts |

Preparation

The mixture of active ingredient, lactose and corn starch is moistened with a 20% solution of polyvinylpyrrolidone in water. The moist mass is passed through a 1.5 mm mesh screen and dried at 45° C. The dried granulate is passed through a 1 mm mesh screen and is homogeneously mixed with magnesium stearate. The composition is compressed into 120 mg-tablets.

EXAMPLE 110

Coated tablets containing 5 mg of 2-ethoxy-4-[N-{1-(2-piperidino-phenyl)-3-methyl-1-butyl}-aminocarbonylmethyl]benzoic acid The tablet core composition is compound from the following ingredients:

| | |
|---|---|
| Active ingredient | 5.0 parts |
| Secondary calcium phosphate | 70.0 parts |
| Corn starch | 50.0 parts |
| Polyvinylpyrrolidone | 4.0 parts |
| Magnesium stearate | 1.0 parts |
| | 130.0 parts |

Preparation

The mixture of active ingredient, calcium phosphate and corn starch is moistened with a 15% solution of polyvinylpyrrolidone in water. The moist mass is passed through a 1 mm mesh screen, dried at 45° C. and then passed through the same screen. After adding the magnesium stearate, 130 mg-tablet cores are compressed from the mixture.

A coating of sugar and talc is applied in known manner to the cores thus produced. The finished coated tablets are polished with wax.

Weight of coated tablet: 180 mg.

Any one of the other compounds embraced by formula I, including forms (A), (B) and (C) of 2-ethoxy- 4-[N-{1-(2-piperidino-phenyl)-3-methyl-1-butyl}-aminocarbonylmethyl]-benzoic acid, an enantiomer thereof or a non-toxic, pharmacologically acceptable salt thereof may be substituted for the particular active ingredient in Examples 29 through 32. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to otherwise skilled in the art that the invention is not limited to these particular embodiments, and that various changes and modifications may be made without departing from the spirit of the invention of the scope of the appended claims.

We claim:

1. A compound of the formula:

(I)

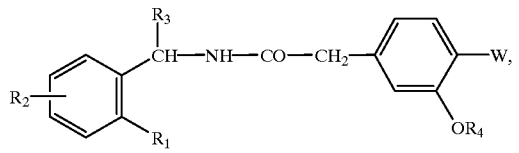

wherein $R_1$ represents an unbranched alkyleneimino group with 4 to 6 carbon atoms optionally mono- or di-(alkyl of 1 to 3 carbon atoms)-substituted;

$R_2$ represents a hydrogen or halogen atom or a methyl or methoxy group;

$R_3$ represents a hydrogen atom, an alkyl group with 1 to 7 carbon atoms, a phenyl group optionally substituted by a halogen atom or a methyl or methoxy group, an alkyl group with 1 or 2 carbon atoms substituted by a hydroxy, alkoxy, alkanoyloxy, tetrahydrofuranyl, tetrahydropyranyl, cyclocalkyl or phenyl group, in which the alkoxy part can contain from 1 to 3 carbon atoms, the alkanoyloxy part can contain 2 or 3 carbon atoms and the cycloalkyl part can contain 3 to 7 carbon atoms, an alkenyl group with 3 to 6 carbon atoms, an alkynyl group with 3 to 5 carbon atoms, a carboxy group or an alkoxycarbonyl group with a total of 2 to 5 carbon atoms;

$R_4$ represents a hydrogen atom, a methyl, ethyl or allyl group; and

W represents a methyl, hydroxymethyl, formyl, carboxyl, alkoxycarbonyl, cyanomethyl, 2-cyanoethyl, 2-carboxyethenyl, alkoxycarbonylmethyl, 2-alkoxycarbonyl-ethyl or 2-alkoxycarbonylethenyl group, in which each alkoxy part can contain from 1 to 4 carbon atoms and can be substituted by a phenyl group; and when $R_3$ is other then hydrogen and/or the radical $R_1$ contains an optically active carbon atom, the enantiomeres and the diastereomeres thereof or their mixtures; when W is carboxyl, a non-toxic salt thereof formed with an inorganic or organic base; or a non-toxic acid addition salt thereof formed by an inorganic or organic acid with the amino function in the $R_1$-position.

2. A compound of claim 1, wherein $R_1$ represents a pyrrolidino, piperidino, 4-methyl-piperidino, 3-methyl-piperidino, 3,3-dimethyl-piperidino, 3,5-dimethyl-piperidino or hexamethylene-imino group;

$R_2$ represents a hydrogen, fluorine or chlorine atom;

$R_3$ represents hydrogen atom, an alkyl group with 1 to 6 carbon atoms, a phenyl, methyl-phenyl, chloro-phenyl, methoxy-phenyl, cyclopropylmethyl, cyclobutylmethyl, cyclopentylmethyl, cyclohexylmethyl, tetrahydrofuran-2-yl-methyl, tetrahydropyran-2-yl-methyl, propargyl, hydroxymethyl, ethoxymethyl, acetoxymethyl, propionyloxymethyl, carboxy, methoxycarbonyl, ethoxycarbonyl or propoxycarbonyl group or an alkenyl group with 3 or 4 carbon atoms;

$R_4$ represents a methyl, ethyl or allyl group; and

W represents a methyl, hydroxymethyl, formyl, carbonyl, benzyloxycarbonyl, carboxymethyl, methoxycarbonylmethyl, ethoxycarbonylmethyl, cyanomethyl, 2-carboxy-ethyl, 2-ethoxycarbonyl-ethyl, 2-cyano-ethyl, 2-carboxy-ethenyl, 2-ethoxycarbonyl-ethenyl or 2-cyano-ethenyl group or an alkoxycarbonyl group with 1 to 4 carbon atoms in the alkoxy part; and when $R_3$ is other then hydrogen and/or $R_1$ represents the 3-methyl-piperidino group, the enantiomeres and the diastereomeres thereof or their mixtures; when W is carboxyl, a non-toxic salt thereof formed with an inorganic or organic base; or a non-toxic acid addition salt thereof formed by an inorganic or organic acid with the amino function in the $R_1$-position.

3. A compound of claim 1, wherein $R_1$ represents a piperidino group;

$R_2$ represents a hydrogen atom;

$R_3$ represents an alkyl group with 1 to 6 carbon atoms, an alkenyl group with 3 or 4 carbon atoms, a phenyl, tetrahydropyran-2-yl-methyl, cyclopropylmethyl or cyclohexylmethyl group;

$R_4$ represents a methyl, ethyl or allyl group; and

W represents a carboxyl, methoxycarbonyl, ethoxycarbonyl or cyanomethyl group; and the enantiomeres thereof or their mixtures; when W is carboxyl, a non-toxic salt thereof formed with an inorganic or organic base; or a non-toxic acid addition salt thereof formed by an inorganic or organic acid with the piperidino function.

4. A compound of claim 1, wherein $R_1$ represents a piperidino group;

$R_2$ represents a hydrogen atom;

$R_3$ represents an alkyl group with 3 to 6 carbon atoms, an alkenyl group with 3 or 4 carbon atoms, a phenyl, cyclopropylmethyl or cyclohexylmethyl group;

$R_4$ represents a methyl or ethyl group; and

W represents a carboxyl group; and the enantiomeres thereof or their mixtures; a non-toxic salt thereof formed with an inorganic or organic base; or a non-toxic acid addition salt thereof formed by an inorganic or organic acid with the piperidino function.

5. A compound of claim 1, wherein $R_1$ represents a piperidino group;

$R_2$ represents a hydrogen atom;

$R_3$ represents an alkyl group with 3 to 6 carbon atoms, a 2-methyl-1-propen-1-yl, cyclomethylpropyl or cyclohexylmethyl group;

$R_4$ represents a methyl or ethyl group; and

W represents a carboxyl group; and the enantiomeres thereof or their mixtures; a non-toxic salt thereof formed with an inorganic or organic base; or a non-toxic acid addition salt thereof formed by an inorganic or organic acid with the piperidino function.

6. A compound of claim 5, wherein $R_3$ represents a n-propyl, n-butyl, isobutyl, sec.butyl, n-pentyl, 2-methyl-1-propen-1-yl, cyclomethylpropyl or cyclohexylmethyl group;

the enantiomeres thereof or their mixtures; a non-toxic salt thereof formed with an inorganic or organic base; or a non-toxic acid addition salt thereof formed by an inorganic or organic acid with the piperidino function.

7. A compound of claim 5, wherein $R_3$ represents a n-propyl, n-butyl, isobutyl, sec.butyl or n-pentyl group; and the enantiomeres thereof or their mixtures; a non-toxic salt thereof formed with an inorganic or organic base; or a non-toxic acid addition salt thereof salt thereof formed by an inorganic or organic acid with the piperidino function.

8. The compound of claim 5, which is 2-ethoxy-4-[N-(1-(2-piperidino-phenyl)-1-butyl)-aminocarbonylmethyl]-benzoic acid; the enantiomeres thereof or their mixtures; a non-toxic salt thereof formed with an inorganic or organic base; or a non-toxic acid addition salt formed by an inorganic or organic acid with the piperidino function.

9. The compound of claim 5, which is 2-ethoxy-4-[N-(1-(2-piperidino-phenyl)-3-methyl-1-butyl)-aminocarbonylmethyl]benzoic acid; the enantiomeres thereof or their mixtures; a non-toxic salt thereof formed with an inorganic or organic base; or a non-toxic acid addition salt formed by an inorganic or organic acid with the piperidino function.

10. The compound of claim 5, which is form (A) of 2-ethoxy-4-[N-(1-(2-piperidino-phenyl)-3-methyl-1-butyl)-aminocarbonylmethyl]-benzoic acid, recrystallized from acetone/petroleum ether, having a melting point of 90°–92° C.

11. The compound of claim 5, which is form (B) of 2-ethoxy-4-[N-(1-(2-piperidino-phenyl)-3-methyl-1-butyl)-aminocarbonylmethyl]-benzoic acid, recrystallized from ethanol/water, having a melting point of 140°–142° C.

12. The compound of claim 5, which is form (C) of 2-ethoxy-4-[N-(1-(2-piperidino-phenyl)-3-methyl-1-butyl)-aminocarbonylmethyl]-benzoic acid, recrystallized from methanol, having a melting point of 74°–85° C.

13. The compound of claim 5, which is 2-ethoxy-4-[N-(α-cyclohexylmethyl-2-piperidino-benzyl)-aminocarbonylmethyl]-benzoic acid; the enantiomeres thereof or their mixtures; a non-toxic salt thereof formed with an inorganic or organic base; or a non-toxic acid addition salt formed by an inorganic or organic acid with the piperidino function.

14. The (S)-enantiomer of a compound as claimed in anyone of the claims 1 to 13; when W is carboxy, a non-toxic salt thereof formed with an inorganic or organic base; or a non-toxic acid addition salt formed by an inorganic or organic acid with the amino function in the $R_1$-position.

15. A hypoglycemic pharmaceutical composition consisting essentially of an inert pharmaceutical carrier and an effective hypoglycemic amount of a compound of claim 1.

* * * * *

UNITED STATES PATENT AND TRADEMARK OFFICE

CERTIFICATE EXTENDING PATENT TERM
UNDER 35 U.S.C. § 156

| | | |
|---|---|---|
| REISSUE PATENT NO. | : | RE 37,035 |
| ISSUED | : | January 30, 2001 |
| REISSUE OF U.S. PATENT NO. | : | 5,216,167 |
| ISSUED | : | June 1, 1993 |
| INVENTORS | : | Wolfgang Grell et al. |
| PATENT OWNER | : | Dr. Karl Thomae GmbH |
| PRODUCT | : | PRANDIN™ (repaglinide) |

This is to certify that an application under 35 U.S.C. § 156 has been filed in the United States Patent and Trademark Office, requesting extension of the term of U.S. Patent No. 5,216,167, now U.S. Reissue Patent No. RE 37,035, based upon the regulatory review of the product PRANDIN™ (repaglinide) by the Food and Drug Administration. Since it appears that the requirements of the law have been met, this certificate extends the term of the patent for the period of 921 days from September 5, 2006, the original expiration date of the reissue patent, subject to the provisions of 35 U.S.C. § 41(b), with all rights pertaining thereto as provided by 35 U.S.C. § 156(b).

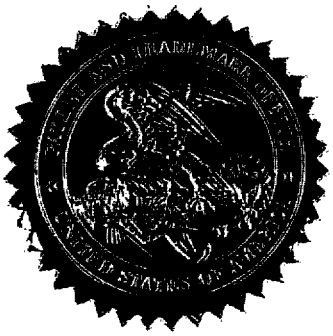

I have caused the seal of the United States Patent and Trademark Office to be affixed this 8th day of February 2001.

Nicholas P. Godici

Nicholas P. Godici
Acting Under Secretary of Commerce for Intellectual Property and
Acting Director of the United States Patent and Trademark Office

UNITED STATES PATENT AND TRADEMARK OFFICE

CERTIFICATE OF CORRECTION

PATENT NO. : RE 37,035 E
DATED : January 30, 2001
INVENTOR(S) : Wolfgang Grell et al.

It is certified that error appears in the above-identified patent and that said Letters Patent is hereby corrected as shown below:

Title page,
Item [73], Assignee, delete "Boehringer Ingelheim KG, Ingelheim (DE)" and insert in its place -- Dr. Karl Thomae GmbH, Biberach an der Riss, Fed. Rep. of Germany --

Signed and Sealed this

Ninth Day of August, 2005

JON W. DUDAS
*Director of the United States Patent and Trademark Office*